US005651972A

United States Patent [19]
Moyer et al.

[11] Patent Number: 5,651,972
[45] Date of Patent: Jul. 29, 1997

[54] USE OF RECOMBINANT SWINE POXVIRUS AS A LIVE VACCINE VECTOR

[75] Inventors: Richard W. Moyer, Gainesville, Fla.; Eladio Viñuela, Madrid, Spain; E. P. J. Gibbs, Gainesville, Fla.

[73] Assignee: University of Florida Research Foundation, Inc., Alachua, Fla.

[21] Appl. No.: 307,499

[22] Filed: Sep. 14, 1994

Related U.S. Application Data

[63] Continuation of Ser. No. 908,241, Jul. 1, 1992, abandoned, which is a continuation-in-part of Ser. No. 908,630, Jun. 29, 1992, abandoned, which is a continuation of Ser. No. 342,212, Apr. 21, 1989, abandoned.

[51] Int. Cl.$^6$ .................. A61K 39/275; A61K 39/245; C12N 7/01; C12N 15/86
[52] U.S. Cl. .................. 424/199.1; 435/320.1; 435/235.1; 424/229.1; 424/232.1; 424/93.2; 536/23.72; 935/65
[58] Field of Search .................. 435/320.1, 235.1, 435/172.3; 424/199.1, 229.1, 232.1, 93.2; 935/65; 536/23.72

[56] References Cited

U.S. PATENT DOCUMENTS

| | | | |
|---|---|---|---|
| 4,722,848 | 2/1988 | Paoletti et al. | 424/199.1 |
| 5,069,901 | 12/1991 | Jones et al. | 424/199.1 |
| 5,174,993 | 12/1992 | Paoletti | 424/199.1 |
| 5,273,876 | 12/1993 | Hock et al. | 435/235.1 |
| 5,310,668 | 5/1994 | Ellis et al. | 424/199.1 |
| 5,382,425 | 1/1995 | Cochran et al. | 435/69.1 |

FOREIGN PATENT DOCUMENTS

| | | |
|---|---|---|
| 0447303 | 9/1991 | European Pat. Off. . |
| 8802022 | 3/1988 | WIPO .................. C12N 15/00 |
| 9214489 | 9/1992 | WIPO . |

OTHER PUBLICATIONS

Piccini, Antonia, and Enzo Paoletti (1986) "The Use of Vaccinia Virus for the Construction of Recombinant Vaccines" BioEssays 5(6):248–252.

Kasza, Louis, E.H. Bohl, D.O. Jones (1960) "Isolation and Cultivation of Swine Pox Virus in Primary Cell cultures of Swine Orgin" Am. J. Vet. Res. pp. 269–273.

Gustafson, D.P. (1986) "Pseudorabies" in Diseases of Swine pp. 274–289.

Mackett, Michael, Geoffrey L. Smith, and Bernard Moss (1985) "The Construction and Characterisation of Vaccinia Virus Recombinants Expressing Foreign Genes" DNA Cloning 2:191–211.

Yuen, Leonard, Julie Dionne, Basil Arif, and Christopher Richardson (1990) "Indentification and Sequencing of the Spheroidin Gene of *Choristoneura biennis* Entomopoxvirus" Virology 175:427–433.

Feller, J.A., R.F. Massung, P.C. Turner, E.P.J. Gibbs, E.O. Backamp, A. Beloso, A. Talavera, E. Viñuela, and R.W. Moyer (1991) "Isolation and Molecular Characterization of the Swinepox Virus Thymidine Kinase Gene" Virology 183:578–585.

Paoletti, Enzo, Bernard R. Lipinskas, Carol Samsonoff, Susan Mercer, and Dennis Panicali (1984) "Construction of live vaccines using genetically engineered poxviruses: Biological activity of vaccinia virus recombinants expressing the hepititis B virus surface antigen and the herpes simplex virus glycoprotein D" Proc. Natl. Acad. Sci. USA 81:193–197.

(List continued on next page.)

*Primary Examiner*—Mary E. Mosher
*Attorney, Agent, or Firm*—Saliwanchik, Lloyd & Saliwanchik

[57] ABSTRACT

The present invention provides a recombinant swinepox virus vector containing a heterologous nucleotide sequence encoding a protein from a selected pathogen inserted into, or replacing, all or a portion of a swinepox virus gene, which gene is not essential to replication of the virus in a host cell. Also provided is a recombinant SPV vector into which a pseudorabies antigen is inserted within the TK gene, which is useful in diagnostic, therapeutic, and prophylactic compositions.

17 Claims, 3 Drawing Sheets

OTHER PUBLICATIONS

Panicali, Dennis, Stephen W. Davis, Randall L. Weinberg, and Enzo Paoletti (1983) "Construction of live vaccines by using genetically engineered poxviruses: Biological activity of recombinant vaccinia virus expressing influenza virus hemagglutinin" Proc. Natl. Acad. Sci. USA 80:5364–5368.

Robinson, A.J., D.J. Lyttle (1992) "Recombinant Parapoxviruses (D) Insertion of Foreign Genes" in Recombinant Poxviruses, pp. 310, 323,324.

Van Der Leek, M.L. et al. (1994) "Evaluation of swinepox virus as a vaccine vector in pigs using an Aujeszky's disease (pseudorabies) virus gene insert coding for glycoproteins gp50 and gp63" The Veterinary Record –Jan. 1, 1994, pp. 13–18.

Bello, L.J. et al. (1987) "Map Location of the Thymidine Kinase Gene of Bovine Herpesvirus 1" Journal of Virology 61(12):4023–4025.

Schnitzlein, W.M. et al. 1991. Virology, vol. 181, pp. 727–732.

Schnitzlein, W.M. et al. 1988. Journal of Virological Methods, vol. 20, pp. 341–352.

Garg, S.K. et al. 1972. Applied Microbiology vol. 23 pp. 180–182.

Marchioli, C.C. et al. 1987. Journal of Virology vol. 61 pp. 3977–3982.

Boyle, D.B. et al. 1987. Virology vol. 156 pp. 355–365.

Taylor, J. et al. 1988. *Vaccine* vol. 6 pp. 466–467, 497–503.

Mayr, A. et al. 1989. J. Vet. Med. B. vol. 36 pp. 81–99.

Foley, P.L. et al. 1991. Ann. N.Y. Acad. Sci. vol. 646 pp. 220–222.

Taylor, J. et al. 1988. *Vaccine* vol. 6 pp. 466–468, 497–503.

Meulemans, G. et al. 1988. *Avian Pathol.* vol. 17 pp. 821–827.

USE OF RECOMBINANT SWINE POXVIRUS AS A LIVE VACCINE VECTOR

CROSS-REFERENCE TO RELATED APPLICATION

This application is a continuation of application Ser. No. 07/908,241, filed Jul. 1, 1992, now abandoned, which is a continuation-in-part of U.S. patent application Ser. No. 07/908,630, filed Jun. 29, 1992, now abandoned, which is a continuation of U.S. patent application Ser. No. 07/342,212, filed Apr. 21, 1989, now abandoned.

FIELD OF THE INVENTION

This invention relates generally to the field of recombinantly-produced proteins and vector systems, and specifically to novel, recombinant Swinepox sequences useful in vector molecules capable of expressing heterologous genes in transformed hosts and in making specialized vectors.

BACKGROUND OF THE INVENTION

Various attempts have been made to construct vaccine vectors from viruses. The use of viruses and virus proteins in eukaryotic host-vector systems has been the subject of a considerable amount of investigation and speculation. Many existing viral vector systems suffer from significant disadvantages and limitations which diminish their utility. For example, a number of eukaryotic viral vectors are either tumorigenic or oncogenic in mammalian systems, creating the potential for serious health and safety problems associated with resultant gene products and accidental infections. Further, in some eukaryotic host-viral vector systems, the gene product itself exhibits antiviral activity, thereby decreasing the yield of that protein.

In the case of simple viruses, the amount of exogenous DNA which can be packaged into a simple virus is limited. This limitation becomes a particularly acute problem when the genes used are eukaryotic. Because eukaryotic genes usually contain intervening sequences, they are too large to fit into simple viruses. In the case of complex viruses, size of exogenous DNA to be inserted is not a limiting factor. However, because they have many restriction sites, it is more difficult to insert exogenous DNA into complex viruses at specific locations.

Studies with vaccinia virus have demonstrated that poxviruses in general have several advantageous features as vaccine vectors. Poxviruses are taxonomically classified into the family Chordopoxvirinae, whose members infect vertebrate hosts, e.g., the Orthopoxvirus vaccinia. Vaccinia virus has recently been developed as a eukaryotic cloning and expression vector (Mackett, M. et al., [1985] *DNA Cloning*, Vol. II, ed. D. M. Glover, pp. 191–212, Oxford: IRL Press; Panicali, D. et al. [1982] *Proc. Natl. Acad. Sci. USA* 88:5364–5368). Numerous viral antigens have been expressed using vaccinia virus vectors (Paoletti, E. et al. [1986] *Proc. Natl. Acad. Sci. USA* 81:193–197; Pictinc, A. et al. [1986] *BioEssays* 5:248–252) including, among others, HBsAg, rabies G protein and the gp120/gp41 of human immunodeficiency virus (HIV). Regulatory sequences from the spruce budworm EPV have been used previously with vaccinia (Yuen, L. et al. [1990] *Virology* 175:427–433).

The advantages of poxviruses as vaccine vectors include the ability of poxvirus-based vaccines to stimulate both cell-mediated and humoral immunity, minimal cost to mass produce vaccine and the stability of the lyophilized vaccine without refrigeration, ease of administration under non-sterile conditions, and the ability to insert at least 25,000 base pairs of foreign DNA into an infectious recombinant, thereby permitting the simultaneous expression of many antigens from one recombinant.

However, although recombinant vaccinia viruses have demonstrated great potential as vaccines, vaccinia has several drawbacks that have prevented its widespread use in both human and veterinary medicine. First, vaccinia virus has a wide host range that includes man and many domestic animals. This could permit the spread of a recombinant vaccinia vaccine to other animal populations not intended for vaccination. Secondly, although the vaccinia virus recombinants are attenuated by inactivation of the thymidine kinase gene, this virus still has the ability to cause potentially serious generalized vaccinal infections in immunocompromised individuals (i.e., patients with AIDS).

Another poxvirus, swinepox virus, the only known member of the genus Suipoxvirus, is naturally restricted to swine and occurs widely throughout the world. Swinepox virus produces a mild, self-limiting disease in swine. (Kasza et al. [1960] *Am. J. Vet. Res.* 21:269–272; Shope [1940] *Arch. Gesamte. Virustorsch* 1:457–467). This virus is characterized by a genome 175 kb in size which includes a thymidine kinase (TK) gene closely resembling the TK genes of other poxviruses (Feller et al. [1991] *Virol.* 183:578–585).

Pseudorabies is one of the most important diseases affecting the swine industries of the USA and several countries within Europe. Losses due to disease in the USA each year run into several million dollars. This disease is characterized in its reservoir host, swine, by central nervous system disorders in suckling pigs, respiratory disease in growing pigs, and fever and inappetence in adult swine. Cattle, dogs, cats, and other species are atypical hosts of pseudorabies, but develop an invariably fatal neurological disease similar to rabies. Highly pathogenic strains of pseudorabies have been detected in the USA and later in Europe since the 1960's (Gustafson, D. P. [1986] "Pseudorabies," in *Diseases of Swine*, pp. 274–289, 6th Edition, eds. Leman, A. D., Straw, B., Glock, R. D., Mengeling, W. I., Penny, R. H. C., and Scholl, E., Publ. ISU press, Ames, Iowa).

The control and the eradication of pseudorabies in the USA has proven to be difficult due to the existence of a large population of feral swine in the southern states which is known to be infected with pseudorabies virus.

There remains a need for a safer and effective vector system to create vaccines directed to diseases of humans and animals, including e.g., pseudorabies infections of swine.

BRIEF SUMMARY OF THE INVENTION

In one aspect, the present invention provides a recombinant swinepox virus vector which contains a heterologous gene or genes encoding a selected pathogenic immunogenic or antigenic protein under the control of a suitable regulatory sequence capable of directing the expression of said protein in a selected host cell. Preferably, the heterologous gene is inserted into the swinepox virus vector, either replacing or disrupting a naturally-occurring swinepox virus sequence or gene which is not essential to the replication of the recombinant swinepox virus vector in a selected host cell.

In one embodiment of such a vector, the heterologous gene is inserted into the thymidine kinase (TK) gene region of swinepox virus. TK is one of the proteins [SEQ ID NO: 58] encoded by a nucleic acid sequence [SEQ ID NO: 57] of the HindIII H fragment or a portion thereof, of the swinepox virus. In an illustrated embodiment, the foreign gene is a pseudorabies gene, most preferably the gp50 and/or gp63 gene. Additionally, other pseudorabies and non-pseudorabies genes are expected to be useful.

In a further aspect, the present invention provides the DNA sequences of the sense strand [SEQ ID NO: 1] and the anti-sense strand [SEQ ID NO: 14] of the approximately 14 kb HindIII C fragment of the swinepox virus. This DNA sequence contains fragments which encode about 27 swine-pox virus proteins.

In a related aspect, the present invention provides the DNA sequences [SEQ ID NOS: 8–13 and 36–56], and putative amino acid sequences [SEQ ID NOS: 2–7 and 15–35] of the 27 proteins encoded by fragments from the 14 kb HindIII C fragment. Certain of these sequences from the fragment, like the TK gene, are expected to be non-essential and thus useful as locations for the insertion of, or replacement by, foreign genes for expression thereof.

In another aspect, the present invention provides the DNA sequence [SEQ ID NO: 57] of the SPV TK gene and the putative amino acid sequence [SEQ ID NO: 58] of TK.

In yet another aspect, the present invention provides a plasmid, p19SPB1, containing the full length SPV TK gene [SEQ ID NO: 57].

In a still further aspect, the present invention provides a therapeutic composition useful in treating a selected disease, which composition contains a swinepox virus vector capable of expressing a heterologous protein capable of alleviating the clinical symptoms of the selected disease.

Another aspect of the invention provides a method for treating an animal, which involves the step of administering to the animal an effective mount of a therapeutic composition as described above.

In yet a further aspect, the present invention provides a vaccine composition comprising a recombinant swinepox vector of this invention capable of expressing an antigen capable of eliciting a protective immune response to the causative agent of the disease for which prophylaxis is desired.

Another aspect of the invention provides a method of vaccinating an animal comprising administering to the animal an effective amount of a vaccine composition of the invention.

In yet another aspect, the present invention provides diagnostic reagents and methods useful for distinguishing between vaccinated and non-vaccinated animals by the use of a swinepox marker gene.

Other aspects and advantages of the present invention are described further in the following detailed description of the preferred embodiments thereof.

BRIEF DESCRIPTION OF THE FIGURES

FIG. 4 provides the DNA sequence [SEQ ID NO: 14] of the reverse complement strand (5' to 3') of the 14,176 bp from the HindIII C fragment of SPV and the amino acid sequences [SEQ ID NOS: 15, 20–22, 27, 32, 35] encoded by reading frame 2.

FIG. 5 provides the DNA sequence [SEQ ID NO: 14] of the reverse complement strand (5' to 3') of the 14,176 bp from the HindIII C fragment of SPV and the amino acid sequences [SEQ ID NOS: 16, 19, 24, 25, 29] encoded by reading frame 3.

FIG. 6 is a map of the TK region of SPV DNA, corresponding to the G fragment of FIG. 1. Restriction endonuclease enzymes are indicated by letters: R for EcoRI, H for HindIII, B for BamHI, X for XbaI, and K for KpnI. Restriction fragment lengths in parentheses are inferred lengths. Lengths of the restriction fragments underlined are experimental results.

FIG. 7 provides the DNA sequence [SEQ ID NO: 57], and putative amino acid sequence [SEQ ID NO: 58], of the SPV TK gene.

FIG. 8 is a restriction map of clone p19SPB1. Restriction enzymes are indicated by letters as described in FIG. 6 and also including S for SalI, P for PstI, Xm for XmaI and Sp for SphI. The symbol (a) indicates an alternate restriction enzyme position. The thick solid line indicates the smallest fragment hybridizing with $TK_1$ or $TK_2$. The XbaI site in this region was not seen before sequencing.

DETAILED DESCRIPTION OF THE INVENTION

Figure 1:
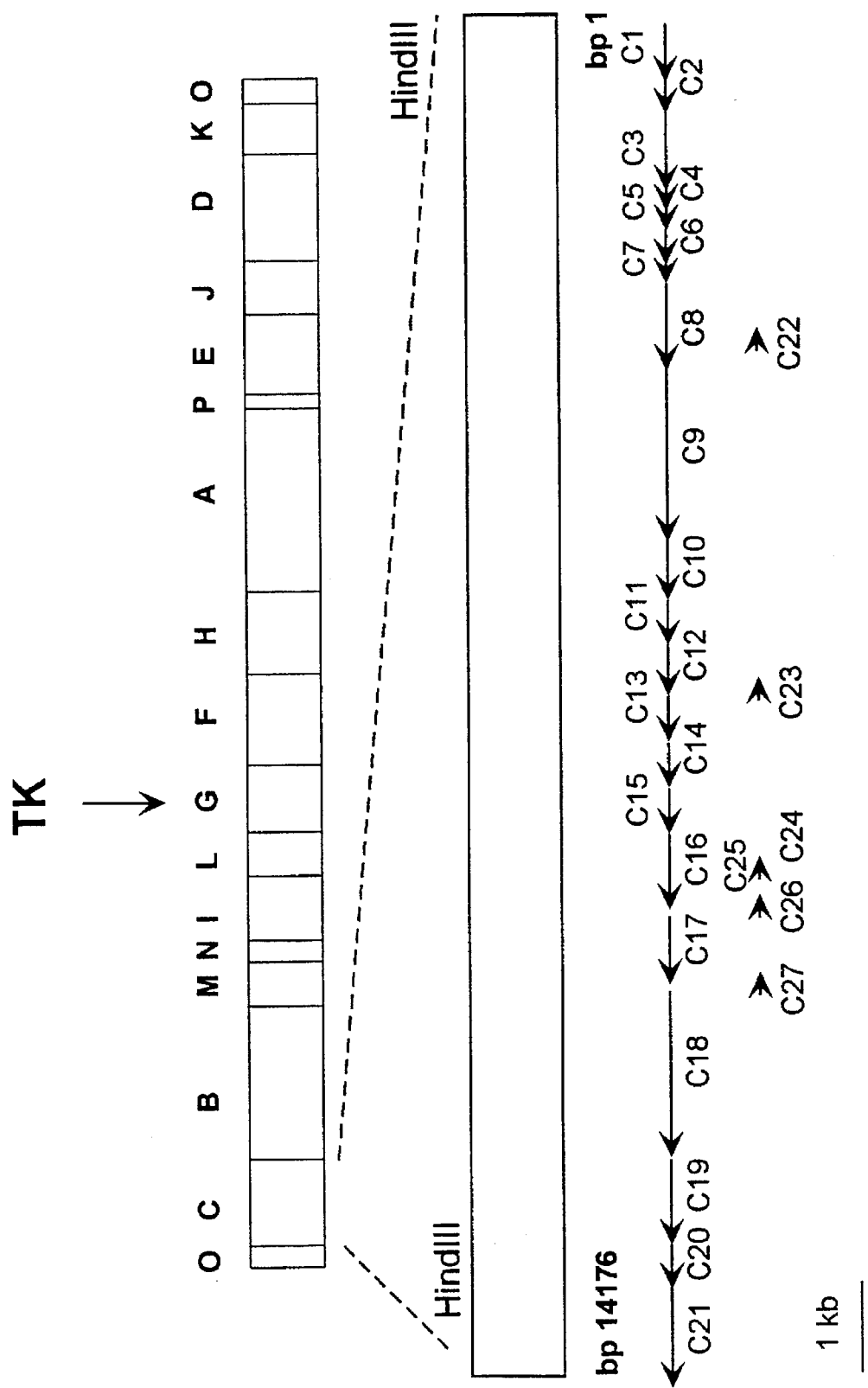
FIG. 1 is a DNA map showing the localized map of SPV DNA based upon probe hybridizations to SPV DNA after restriction enzyme digestion. The approximately 14 kb HindIII C fragment is expanded in the lower portion of the figure to indicate the relative locations and reading frame directions of identified genes, which are labeled by C followed by a number.

The subject invention concerns a novel, efficient and safer means for vaccinating humans, swine, or other animals against various diseases. This procedure is carried out by the use of a modified recombinant swine poxvirus (SPV) as a vector into which heterologous antigenic sequences may be inserted. Because SPV is host-restricted to swine, the use of modified recombinant SPV as a live vaccine vector eliminates the risk of spreading infection with the virus to other animal populations not intended for vaccination.

The present invention thus provides novel swine poxvirus nucleotide sequences, which may be employed in the construction of the recombinant SPV vector useful for expressing heterologous proteins, preferably antigenic or immunogenic proteins, both in vivo as a vaccine, and in vitro for production of the selected protein. Such recombinant vectors are useful in therapeutic and vaccinal compositions. Such infectious agents of swine include pseudorabies virus, TGEV, African Swine Fever Virus, porcine parvovirus, swine influenza, hog cholera, and several bacterial pathogens.

Modification of the SPV involves the replacement of one or more SPV genes which are not essential to replication of the SPV, or portions thereof, with a foreign gene. Additionally, the foreign gene may be inserted within the selected SPV gene, thus disrupting the translation thereof into the SPV protein.

The SPV vector of this invention may be most desirably employed to express antigenic or immunogenic proteins from a variety of infectious agents which cause disease in animals and humans. It is anticipated that genes from any pathogen may be expressed in the SPV vector. For example, suitable genes include swine influenza hemagglutinin, the S gene from canine, bovine, feline, or porcine coronavirus, bovine herpesvirus glycoproteins, porcine parvivirus capsid gene, rabies G, HIV capsids gp120 and gag-pol, Lyme disease antigens, *Bordetella pertussis*, mycoplasma pneumonia, *Treponema hydystentry*, and human influenza genes. However, for purposes of illustration in this application, the foreign gene is selected from pseudorabies virus. Suitable pseudorabies genes include, for example, gII, gIII, and gp50.

The SPV gene selected as a target site for insertion of, or replacement by, a foreign gene sequence depends upon its function as being non-essential to the replication of the SPV. Currently, the preferred target gene is the TK gene of SPV. The present invention provides the polynucleotide [SEQ ID NO: 57] and amino sequence [SEQ ID NO: 58] of the SPV TK gene. The isolation of this gene from the HindIII G fragment of SPV is described in Example 1, and its sequences are provided in FIG. 6. Because a drug resistance marker for TK is known, e.g., bromodeoxyuridine (BUdR) (selects for TK⁻; methotrexate (Aminopterin) selects for TK+), the insertion of a foreign gene which replaces or disrupts the TK gene may be detected in a successful recombinant SPV by conventional procedures.

It is expected that other SPV genes or portions thereof, will provide other non-essential gene sites as targets for insertion of the foreign gene in the recombinant vector. For example, C8L encodes the host range protein and C4L encodes the IFN-γ receptor. Expression or interruption of these gene sequences may impact upon the immunogenicity of the recombinant virus. The present invention provides the polynucleotide sequences, both sense [SEQ ID NO: 1] and anti-sense [SEQ ID NO: 14], of the HindIII C fragment of SPV, which is described in more detail in Example 2 below (FIG. 2 [SEQ ID NO: 1], FIG. 3 [SEQ ID NO: 14], FIG. 4 [SEQ ID NO: 14], and FIG. 5 [SEQ ID NO: 14]). Also provided are the putative amino acid sequences of 27 proteins encoded by these sequences (FIG. 2 [SEQ ID NOS: 2–7], FIG. 3 [SEQ ID NOS: 17, 18, 23, 26, 28, 30, 31, 33, 34], FIG. 4 [SEQ ID NOS: 15, 20–22, 27, 32, 35], and FIG. 5 [SEQ ID NOS: 16, 19, 24, 25, 29]).

In addition to the use of the amino acid sequences and corresponding nucleotide sequences of the specifically-recited embodiments of SPV proteins and genes of this invention which are described herein and in the Figures, the invention also encompasses the use of other DNA and amino acid sequences of the SPV proteins of this invention. For example, allelic variations (naturally-occurring base changes in the species population which may or may not result in an amino acid change) of the illustrated SPV DNA sequences encoding the various amino acid sequences are also included in the present invention, as well as analogs or derivatives thereof. Similarly, DNA sequences which code for protein sequences of the invention but which differ in codon sequence due to the degeneracies of the genetic code or variations in the DNA sequence encoding these proteins which are caused by point mutations or by induced modifications to enhance the activity, half-life or production of the peptide encoded thereby are also encompassed in the invention.

Variations in the amino acid sequences of the SPV proteins of this invention may typically include analogs that differ by only 1 to about 4 codon changes. Other examples of analogs include polypeptides with minor amino acid variations from the natural amino acid sequence of SPV gene proteins and/or the fusion partner; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a significant effect on its activity, especially if the replacement does not involve an amino acid at an epitope of the polypeptides of this invention.

To construct modified recombinant SPV vectors of this invention, the modification technique of Turner and Moyer (1992) *J. Virol.* 66(4):2076–2085, incorporated herein by reference, may be used to insert the foreign gene or genes, whether they be markers, antigens, or another protein, to specific selected sequences of SPV. This method requires knowledge of the DNA sequence of the target gene, rather than the availability of a cloned copy.

Briefly, this method is performed as follows. The Ecogpt gene from *Escherichia coli* encodes a xanthine guanine phosphoribosyl transferase. When expressed in swinepox with the vaccinia $P_{7.5}$ promoter (Cochran, M. A., et al. [1985] *J. Virol.* 54:30–37), Ecogpt confers resistance to mycophenolic acid (MPA) in the presence of guanine and hypoxanthine, allowing the formation of virus plaques. By flanking $P_{7.5}$-Ecogpt (the gpt cassette) with the left and right arms of the target SPV gene, this selectable marker gene can be inserted into the desired protein by recombination following transfection.

The strategy described here involves the generation of these components by polymerase chain reaction (PCR) (Saiki, R. K. et al. [1988] *Science* 239:487–491), and their assembly by means of recombinant PCR (Higuchi, R. [1990] "Recombinant PCR," In *PCR Protocols: A Guide to Methods and Applications*, eds. M. A. Innis et al., Academic Press, Inc., New York, p. 177–183). PCR reactions are performed using standard parameters: 30 cycles of 94° C. for 1 minute, 45° C. for 1 minute, 72° C. for 2 minutes, followed by 72° C. for 8 minutes to complete extensions. Unrelated PCR products can be joined by this process following annealing, provided that the inside primers have an overlap. The resulting linear PCR products can be transferred directly into cells infected with wild-type virus, and $MPA^R$ virus recombinants selected. As an alternatively to this PCR technique, the heterologous gene may be cloned into a plasmid for recombination.

Thereafter the selected heterologous gene encoding an immunogenic or antigenic protein of interest from a selected pathogen is then inserted into the modified SPV by employing similar recombination processes. Briefly, a recombination plasmid, preferably an *E. coli* plasmid, is constructed in which the selected foreign gene, such as the pseudorabies gp50 and/or gp63 gene, is provided with a selected regulatory sequences, e.g., promoter regions. Preferably, when utilized in the vaccinia and fowlpox expression systems, the promoter is a vaccinia virus promoter. The construct formed by the foreign gene and the selected promoter or regulatory sequence may be inserted into the plasmid or assembled therein, to create a recombination vector.

However, other suitable plasmids and regulatory sequences capable of directing the replication and expression of the foreign gene product in a selected host cell are well known to those of skill in the art. Such promoters, for use in poxvirus, are poxvirus promoters including 7.5 k, 11 k, and ATI. Preferably, the plasmid is purified, using conventional techniques.

The recombination plasmid is then transfected by conventional techniques [See, e.g., Sambrook et al. [1989] *Molecular Cloning: A Laboratory Manual*, Cold Spring Harbor Laboratory, New York) into a suitable host and recombination occurs, placing the foreign gene and promoter system into the target gene region of SPV which contains the marker gene, thus destroying the functionality of that marker. In this manner, successful recombinants containing the foreign gene may be identified by the absence of the marker gene function. Alternatively, depending upon the gene inserted, one can select for a particular, rather than against, as described immediately above. Suitable markers for this include, for example, ecogpt+ and β-gal exp+.

Alternatively, as illustrated in Example 3, when the target gene is the SPV TK gene [SEQ I12) NO: 57], conventional technologies for insertion of the foreign gene may be used. For example, following the construction of the recombination plasmid containing the desired foreign gene DNA as described above, the plasmid is transfected into cells infected with wild type SPV (TK$^+$). Within the infected cell the vector undergoes a homologous recombination event with the TK sequences of the wild type SPV DNA resulting in the generation of recombinant SPV with a TK negative (TK$^-$) genotype. The TK$^-$ progeny can then be selected by their ability to replicate in TK$^-$ swine host cells in the presence of 5-bromo-2-deoxyuridine (5-BUdr).

Recombinant SPV can be further selected by plaque hybridization using a probe derived from or complementary to the inserted foreign gene. The SPV recombinants can then be grown up in mass culture and analyzed for expression of the gene of interest. Alternatively, hybridization can be used to identify recombinant viruses when no marker exists.

Suitable hosts for use in production of the recombination plasmids include, for example, *E. coli*, Bacillus, Streptomyces, Saccharomyces, mammalian, such as Chinese Hamster ovary cells (CHO) or COS-1 cells, yeast, and insect cells. Suitable vectors therefor, which would be useful as recombination plasmids, are known and available from private and public laboratories and depositories and from commercial vendors. Currently, the most preferred host is *E. coli*. The selection of other suitable host cells and methods for transformation, culture, amplification, screening and product production and purification can be performed by one of skill in the art by reference to known techniques. See, e.g., Gething and Sambrook (1981) *Nature* 293:620–625).

The plasmid p19SPB1, which is currently being maintained in the laboratory of Dr. Richard Moyer of the University of Florida, contains a 1.8 kb HindIII to BamHI fragment containing the entire SPV TK gene. The plasmid can be obtained as described in Example 1 below and isolated and purified by use of standard procedures, for example, using cleared lysate-isopycnic density gradient procedures, and the like. This plasmid, which contains the SPV TK gene, thus provides a source of probes and selection for use in the methods described above.

Desirably, the recombinant SPV vectors of the invention can be formulated into therapeutic and vaccinal compositions, for use in treatment and prophylaxis of a desired disease. These formulations may contain appropriate, conventional, carriers or diluents, preservatives, pH adjusters or stabilizers.

For example, suitable carriers and diluents include sterile saline, lactose, sucrose, calcium phosphate, gelatin, dextrin, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

A therapeutic composition or vaccine composition of the invention may contain between about $10^1$ to about $10^8$ of the rSPV of the invention. These compositions of the invention contain suitable amounts of the active ingredient, the recombinant SPV vector containing the foreign gene, which can be determined by one of skill in the art based upon the level of immune response desired. In general, however, the therapeutic or vaccine composition contains between about $1\times10^5$ to about $1\times10^7$ plaque forming units (PFU) per mL, and more preferably between $1\times10^6$ and $3\times10^6$ PFU/mL.

The therapeutic or vaccine composition of the invention may contain one or more rSPV of the invention, each of which may contain different antigens directed to the same or different pathogens.

Such a therapeutic composition may be administered 1–2 times per day over about a 6 week period. However, suitable dosage adjustments may be made by the attending veterinarian depending upon the age, sex, weight and general health of the patient or animal.

Optionally, this composition may also contain therapeutic agents useful in treating pseudorabies, or other conditions related to the infection being treated. For example, the recombinant SPV vector may be useful in delivery of a growth hormone, growth hormone releasing factor, or cytokine, such as IL-2, IL-5 and IL-3.

A vaccine composition of the invention may also contain a suitable adjuvant. The adjuvant is used as a non-specific irritant to attract leukocytes or enhance an immune response. Such adjuvants include, among others, mineral oil and water, aluminum hydroxide, Amphigen, Avridine, L121/ squalene, D-lactide-polylactide/glycoside, pluronic plyois, muramyl dipeptide, killed Bordetella, saponins, as Quil A.

Suitable doses of the vaccine composition of the invention can be readily determined by one of skill in the art. Generally, a suitable dose is between 1 to 5 ml, of the vaccine composition. Further, the quantity to be administered depends on the size of the host to be treated, the capacity of the host's immune system to synthesize antibodies, the degree of protection desired, and may be adjusted by one of skill in the art. However, suitable dose ranges are of the order of about several hundred micrograms of active ingredient per host.

The therapeutic or vaccine compositions are administered in a manner compatible with the dosage formulation, and such amount as will be therapeutically effective and immunogenic. Typically, the composition can be administered by intradermal scarification using a bifurcated needle analogous to that used for smallpox vaccines in humans. However, any suitable route is acceptable. Preferably, this route is intradermal, intramuscular, subcutaneously or oral. It is anticipated that a suitable regime for administration is a single treatment.

Further, the present recombinant swinepox vectors of the invention are useful as diagnostic reagents and in methods for diagnosing or distinguishing between vaccinated and non-vaccinated animals. As with any antigenic protein or peptide, antibodies may be developed against a selected protein of the invention using conventional techniques. These antibodies may be polyclonal, recombinant, or, preferably monoclonal, and may optionally be associated with a detectable label. Further, using known techniques, probes may be developed from the swinepox proteins of the invention and used to detect antibodies directed thereto in a fluid sample, preferably serum. Alternatively, known sandwich assay techniques may be used, and may, preferably, be adapted into a kit for use by clinical or veterinary laboratories.

The examples below, specifically Examples 5 through 7, illustrate the utility of SPV as a vaccine vector using the pseudorabies gene coding for the gp50 and gp63 glycoproteins as an indicator gene. Such recombinant viruses avoid the possibility and consequences of reversion to virulence or recombination (Buffer, R. M. et al. [1985] *Nature* 317:813–815; Joklik, W. K. et al. [1988] *Vaccine* 6:123–128), can easily be differentiated from natural infection, and allow the simultaneous inclusion of other gene inserts or the use of a "cocktail" of recombinants for vaccination against additional diseases.

In Examples 5 through 7 below, following demonstration of pseudorabies virus (PRV) serum neutralizing antibodies in pigs vaccinated with a swinepox-pseudorabies gp50/63 recombinant virus (SP-PRV) by scarification or intramuscular (IM) injection, two efficacy trials were conducted. In the first efficacy trial, which was designed to investigate parenteral vaccination, 30 pigs were challenged with virulent PRV three weeks after the administration of SP-PRV by scarification (n=10) of IM injection (n=10). The recombinant virus conferred partial protection by either route when the response to challenge in vaccinates was compared to that in unvaccinated controls (n=10). Pigs vaccinated by IM injection developed the highest PRV serum neutralizing (SN) antibody titers, exhibited less severe clinical signs, maintained positive weight gains and shed PRV for fewer days after challenge.

In the second efficacy trial, which was designed to investigate oral vaccination, 34 pigs were challenged with virulent PRV three weeks after the oral administration of swinepox virus (SPV) with an intact thymidine kinase (TK) gene (SPV $TK^+$) (n=6), SPV negative for the TK gene (SPV $TK^-$) (n=6) or SP-PRV (n=10). Although there was no evidence of a PRV SN antibody response in pigs vaccinated with SP-PRV, they exhibited less severe clinical signs, maintained their weight and shed PRV for fewer days after challenge when compared to the response in unvaccinated controls (n=10). When evaluating the same parameters, SPV $TK^+$ vaccinates responded almost as well, suggesting the presence of non-specific immunity. The SPV $TK^-$ vaccinates and controls, in turn, responded poorly to challenge.

No transmission of recombinant virus to in-contact controls was detected during the 3-week observation after vaccination in either efficacy trial. The antibody response elicited in pigs vaccinated with SP-PRV by scarification or IM injection, and the evidence of subsequent protection upon challenge with virulent PRV, demonstrates that SPV may be a potential vaccine vector. Since SPV is host restricted and there appears to be no transmission of SP-PRV to in-contact controls, this virus is an ideal vaccine vector candidate when used parenterally. Although SP-PRV failed to induce a PRV SN antibody response by the oral route, the data suggests the presence of some immunity (cell-mediated immunity was not evaluated).

The following examples illustrate the preferred methods for preparing the vector and compositions of the invention, as well as the trials described above. These examples are illustrative only and do not limit the scope of the invention.

EXAMPLE 1

Obtaining SPV TK Gene

SPV DNA is large and similar in size to the 180 kb genome of vaccinia. Many strains of SPV are available from conventional depositories, such as the American Type Culture Collection or from the Centers for Disease Control. SPV DNA was digested with the restriction enzymes HindIII, BamHI, EcoRI, SalI, and doubly digested with the following combinations of enzymes: HindIII+EcoRI, BamHi+EcoRI, and SalI+EcoRI. The restriction enzymes disclosed can be purchased from Bethesda Research Laboratories, Gaithersburg, Md., or New England Biolabs, Beverly, Mass. The enzymes are used according to the instructions provided by the supplier.

The digestion products were separated by agarose gel electrophoresis, the resolved fragments transferred to either nitrocellulose or nylon membranes and hybridized at 45° C. with a radiolabeled oligonucleotide probe of the following sequence:

T(TCA)GA(TC)GA(AG)GGXCA(AG)TT(TC)TT [SEQ ID NO: 59].

The oligonucleotide probes are degenerate, i.e., the probes are really mixtures of oligos with a selected set of sequences. In the above sequence, X=N=any nucleotide (A, C, T, or G) at that position. The ( ) indicate that at that position, only those nucleotides indicated within the parentheses were used during synthesis. The probes were synthesized using conventional phosphoramidite methodology and an Applied Biosystems machine.

Hybridization to DNA fragments of the following molecular weights, depending on the particular digest, was observed: HindIII=9.1 kb; EcoRI=9.2 kb; SalI and EcoRI=8.2 kb (i.e., no SalI site within the EcoRI fragment); BamHI=4.9 kb; HindIII and EcoRI=5.9 kb; BamHI and EcoRI=4.1 kb. Construction of a map based on this data correctly predicted that upon HindIII and EcoRI digestion, the probe should hybridize with a 1.8 kb fragment (see FIGS. 1 and 7).

In order to clone the gene, SPV DNA was digested with BamHI, and the total mixture of fragments was cloned into pUC19 (available from United States Biochemical Corporation, Cleveland, Ohio 44122). Transformant bacterial colonies were replica lifted onto nitrocellulose filters and hybridized to the radiolabeled oligonucleotide probe described above.

From one of the positive colonies, a plasmid was isolated which contained a BamHI fragment of the expected size which upon rehybridization to the probe remained positive. The likelihood that the fragment of a cloned SPV contained the TK gene was confirmed by hybridization with a second degenerate oligonucleotide probe prepared from conserved sequences derived from a different conserved region of previously sequenced TK genes. The sequence of this second probe was as follows with the X and ( ) as described above:

GGXCCXATGTF(CT)AG(CT)GGX [SEQ ID NO: 60].

Restriction mapping of this plasmid, designated p19SPB1, separation of the resulting fragments and hybridization of the resulting fragments with the probes described thus far allowed preparation of the map shown in FIG. 8 and further localization of the TK gene to a 1.8 kb HindIII/BamHI fragment bordering the cloning site of the plasmid. Sequencing of 1.8 kb HindIII/BamHI fragment yielded an open reading frame of 543 nucleotides with an upstream sequence typical of early vaccinia promoters. The sequence of the TK gene [SEQ ID NO: 57] is shown in FIG. 7, wherein the coding portion is shown by the designation of amino acids [SEQ ID NO: 58].

EXAMPLE 2

Analysis of SPV HindIII C Fragment Sequence

Digestion of SPV with HindIII, as described above in Example 1, resulted in the identification of 17 fragments, designated A to O, in order of decreasing size. The map of these HindIII fragments is illustrated in FIG. 1 above. As described above, the TK gene is found in the HindIII G fragment.

Figure 2:
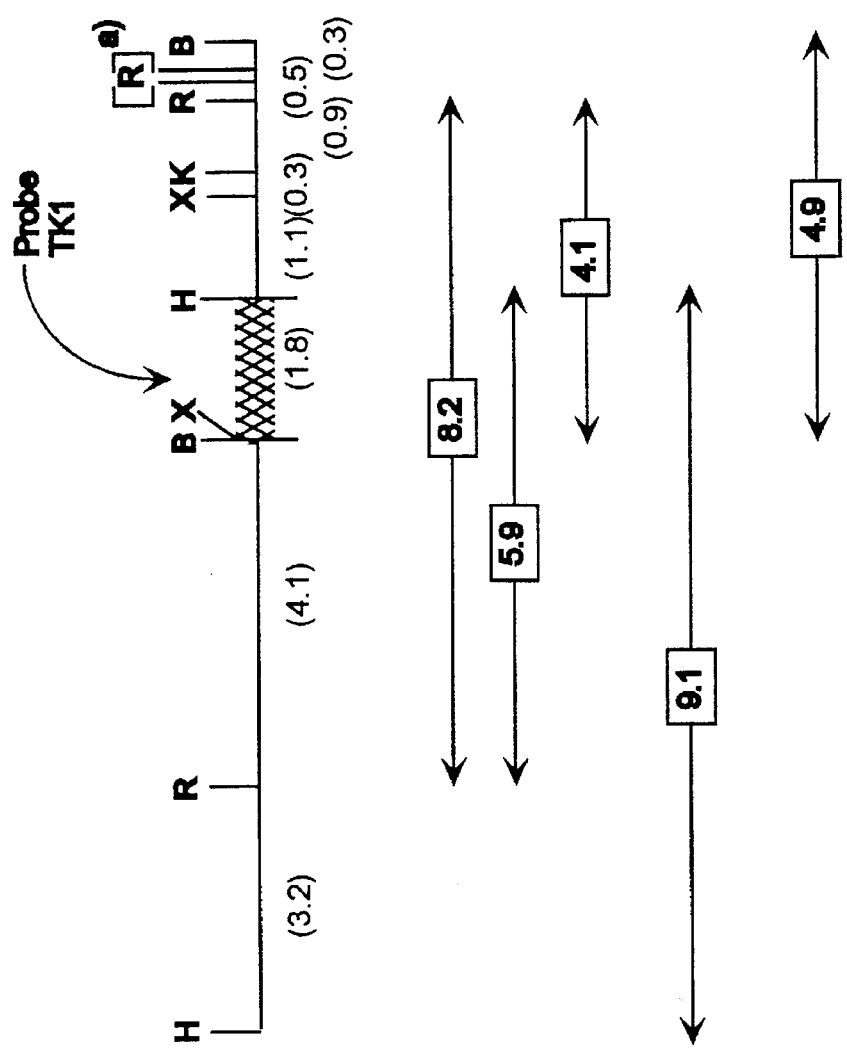
FIG. 2 provides the DNA sequence [SEQ ID NO: 1] of the sense strand (5'to 3') of the HindIII C fragment of SPV and the putative amino acid sequences [SEQ ID NOS: 2–7] encoded thereby. Reading frame 1 encodes C24R and C23R. Reading frame 2 encodes C27R. Reading frame 3 encodes C26R, C25R and C22R.
Figure 3:
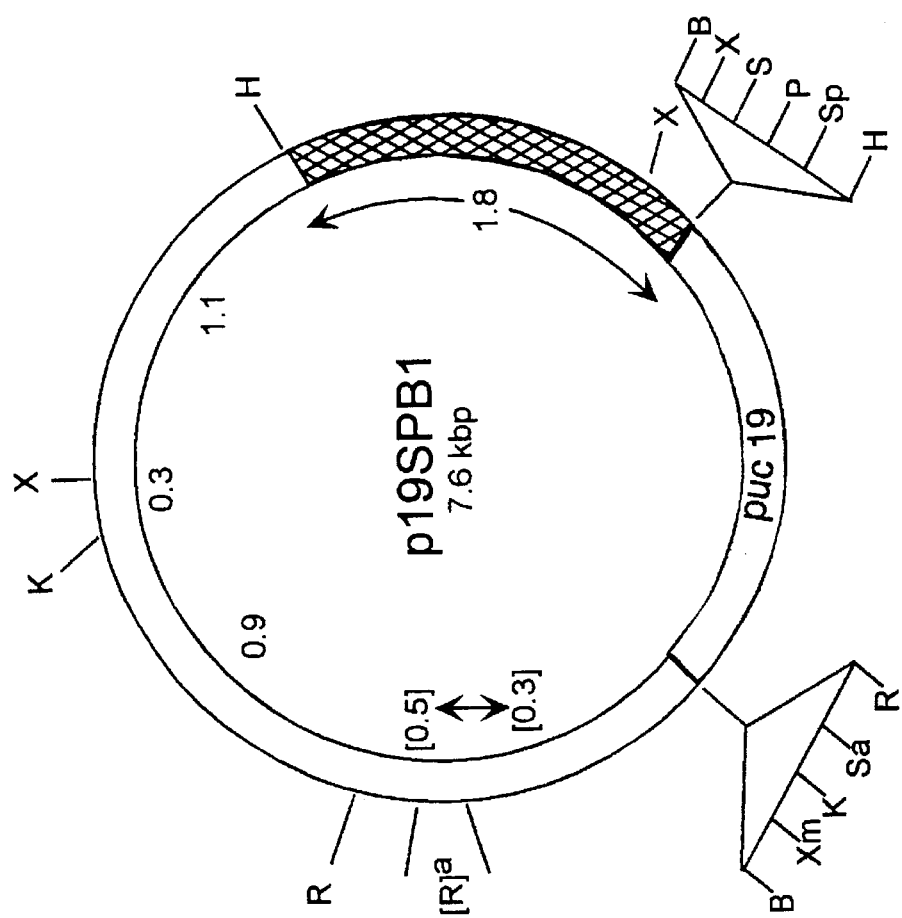
FIG. 3 provides the DNA sequence [SEQ ID NO: 14] of the reverse complement strand (5°14 3') of the 14,176 bp from the HindIII C fragment of SPV and the putative amino acid sequences [SEQ ID NOS: 17, 18, 23, 26, 28, 30, 31, 33, 34] encoded by reading frame 1.

Analysis of the HindIII C fragment, revealed 27 open reading frames, 6 on the sense strand [SEQ ID NO: 1] and 21 on the reverse complementary strand [SEQ ID NO: 14] (FIG. 3, 4, and 5). FIG. 3 illustrates the DNA sequence [SEQ ID NO: 14] of the reverse complementary strand, 5'–3', and the proteins encoded by reading frame 1 of that strand. These proteins are designated C20L [SEQ ID NO: 31], C19L [SEQ ID NO: 30], C17L [SEQ ID NO: 28], C15L [SEQ ID NO: 26], C12L [SEQ ID NO: 23], C7L [SEQ ID NO: 18], C6L [SEQ ID NO: 17], C3L [SEQ ID NO: 34] and C2L [SEQ ID NO: 33] because in the virus genome, the nucleotides encoding these proteins are translated from right to left. FIG. 4 also illustrates the DNA sequence [SEQ ID NO: 14] of the reverse complementary strand, 5' to 3', and the proteins encoded by reading frame 2 (C21L [SEQ ID NO: 32], C16L [SEQ ID NO: 27], C11L [SEQ ID NO: 22], C10L [SEQ ID NO: 21], C9L [SEQ ID NO: 20], C5L [SEQ ID NO: 35] and C1L [SEQ ID NO: 15]). FIG. 5 illustrates the DNA sequence [SEQ ID NO: 14] of this same strand, and the proteins encoded by reading frame 3 (C18L [SEQ ID NO: 29], C14L [SEQ ID NO: 25], C13L [SEQ ID NO: 24], C8L [SEQ ID NO: 19] and C4L [SEQ ID NO: 16]). FIG. 2 illustrates the DNA sequence of the sense strand [SEQ ID NO: 1] of the HindIII C fragment, and the proteins encoded thereby. These proteins, designated C27R to C22R [SEQ ID NOS: 2–7], are encoded on nucleotides which are translated from left to right. Proteins C26R [SEQ ID NO: 3] and C25R [SEQ ID NO: 4] are on reading frame 1; protein C22R [SEQ ID NO: 7] is on reading frame 2; and proteins C27R [SEQ ID NO: 2], C24R [SEQ ID NO: 5] and C23R [SEQ ID NO: 6] are on reading frame 3.

Table 1 below provides a tabular summary of characteristics of these deduced proteins of the open reading frames (ORF).

TABLE 1

| Protein | Amino Acid Length | Molecular Weight[a] | N-glycosylation sites[b] | Charge[c] | Homology |
|---|---|---|---|---|---|
| C2L [SEQ ID NO:33] | 340 | 39.6 | 4 | −4 | Yes |
| C1L [SEQ ID NO:15] | 92 | 10.8 | 1 | +8 | None |
| C3L [SEQ ID NO:34] | 269 | 31.5 | 1 | +20 | Yes |
| C4L [SEQ ID NO:16] | 530 | 62.6 | 3 | −10 | Yes |
| C5L [SEQ ID NO:33] | 236 | 28.5 | 4 | −4 | Yes |
| C6L [SEQ ID NO:33] | 274 | 32.2 | 4 | −4 | Yes |
| C7L [SEQ ID NO:33] | 155 | 18.5 | 4 | −4 | Yes |
| C8L [SEQ ID NO:33] | 86 | 9.8 | 4 | −4 | Yes |
| C9L [SEQ ID NO:33] | 134 | 15.8 | 4 | −4 | Yes |
| C10L [SEQ ID NO:33] | 167 | 19.9 | 4 | −4 | Yes |
| C11L [SEQ ID NO:33] | 142 | 15.7 | 4 | −4 | Yes |
| C12L [SEQ ID NO:33] | 75 | 9.2 | 4 | −4 | Yes |
| C13L [SEQ ID NO:33] | 500 | 57.5 | 4 | −4 | Yes |
| C14L [SEQ ID NO:33] | 274 | 31.8 | 4 | −4 | Yes |
| C15L [SEQ ID NO:33] | 86 | 10.1 | 4 | −4 | Yes |
| C16L [SEQ ID NO:33] | 73 | 8.9 | 4 | −4 | Yes |
| C17L | 70 | 8.1 | 4 | −4 | Yes |

TABLE 1-continued

| Protein | Amino Acid Length | Molecular Weight[a] | N-glycosylation sites[b] | Charge[c] | Homology |
|---|---|---|---|---|---|
| [SEQ ID NO:33] | | | | | |
| C18L | 67 | 8.3 | 4 | −4 | Yes |
| [SEQ ID NO:33] | | | | | |
| C19L | 215 | 24.6 | 4 | −4 | Yes |
| [SEQ ID NO:33] | | | | | |
| C20L | 440 | 52.9 | 4 | −4 | Yes |
| [SEQ ID NO:33] | | | | | |
| C21L | 67 | 8.1 | 4 | −4 | Yes |
| [SEQ ID NO:33] | | | | | |
| C22L | 124 | 14.8 | 4 | −4 | Yes |
| [SEQ ID NO:33] | | | | | |
| C23L | 100 | 11.5 | 4 | −4 | Yes |
| [SEQ ID NO:33] | | | | | |
| C24L | 59 | 6.6 | 4 | −4 | Yes |
| [SEQ ID NO:33] | | | | | |
| C25L | 50 | 6.0 | 4 | −4 | Yes |
| [SEQ ID NO:33] | | | | | |
| C26L | 114 | 13.0 | 4 | −4 | Yes |
| [SEQ ID NO:33] | | | | | |
| C27L | 121 | 13.2 | 4 | −4 | Yes |
| [SEQ ID NO:33] | | | | | |

[a]Expressed in kD; calculated by GCG PeptideSort.
[b]Potential sites predicted by GCG PeptideStructure.
[c]Charge of polypeptide at pH 7.0; calculated by GCG PeptideSort. Charges >0 represent basic proteins while charges <0 would be acidic proteins.

Using the GCG programs, the complete nucleotide sequence of the HindIII C fragment was searched for homology against the GertBank and EMBL databases. The sequence was also searched for any open reading frames. An arbitrary designation of proteins of >50 amino acids was chosen for consideration. The individual polypeptides of the ORFs were searched for homolog against the SwissProt (Release 20.0) database using the Fasta program (Devereux et al. 1984).

As can be seen in the table above, several of the proteins were found to have homology to known sequences. Sequences were considered to be homologous under the arbitrarily defined parameters of either a 20% or greater homology or an amino acid overlap greater than approximately 50 aa. C2L [SEQ D NO: 33] has a 20% identity with mouse Ig epsilon chain (75 amino acid overlap) and an 18% identity with Berne virus peplomer glycoprotein (162 amino acid overlap). C3L [SEQ D NO: 34] has a 26% identity with rabbit RMLP receptor (217 amino acid overlap), 23% identity with dog RDCL receptor (263 amino acid overlap), 25% identity with human C5A receptor (246 amino acid overlap), and 22% identity with human FMLP receptor (250 amino acid overlap). C4L [SEQ D NO: 16] has a 30% identity with myxomal virus MT-9 protein (440 amino acid overlap), 33% identity with myxoma virus MT-8 protein (250 amino acid overlap), 29% identity with vaccinia A55 protein (532 amino acid overlap), and a 22% identity with vaccinia C2 protein (467 amino acid overlap). C5L [SEQ ID NO: 35] has a 35% identity with vaccinia K7 protein (79 amino acid overlap) and a 20% identity with fowlpox DNA polymerase (247 amino acid overlap). C6L [SEQ ID NO: 17] has a 25% identity with the human γ interferon receptor (206 amino acid overlap). C8L [SEQ ID NO: 19] has a 44% identity with vaccinia K4 protein (79 amino acid overlap), a 30% identity with cowpox host range protein, (27 amino acid overlap), and a 26% identity with vaccinia host range protein (27 amino acid overlap). C10L [SEQ ID NO: 21] has a 20% identity with yeast SEC 59 membrane protein (161 amino acid overlap). C11L [SEQ D NO: 22] has 56% identity with vaccinia protease-like protein (146 amino acid overlap), 53% identity with ORF virus pseudoprotease (137 amino acid overlap), and 34% identity with FIV protease (133 amino acid overlap). C13L [SEQ ID NO: 24] has a 25% identity with vaccinia F3 protein (490 amino acid overlap), 21% identity with vaccinia C2 protein (250 amino acid overlap), 24% identity with vaccinia A55 protein (95 amino acid overlap), and 26% identity with myxoma virus MT-9 protein (203 amino acid overlap). C14L [SEQ ID NO: 25] has 78% identity with vaccinia ribonucleoside diphosphate reductase small chain protein (270 amino acid overlap), and with the same gene in Spisula solidissma 74% identity (247 amino acid overlap), yeast 58% identity (285 amino acid overlap), mouse 74% identity (270 amino acid overlap), varicella zoster virus 26% identity (271 amino acid overlap), HSV 26% identity (260 amino acid overlap), E. coli 27% identity (123 amino acid overlap), and epstein barr 29% identity (239 amino acid overlap). C19L [SEQ ID NO: 30] has 46% identity with vaccinia F9 protein (215 amino acid overlap), 25% identity with fowlpox FP2 protein (169 amino acid overlap), and 43% identity with cowpox ATI inclusion protein (21 amino acid overlap). C20L [SEQ ID NO: 31] has 72% identity with a vaccinia possible protein kinase gene (432 amino acid overlap) and 20% identity with yeast clathrin heavy chain protein (54 amino acid overlap). C21L [SEQ ID NO: 32] has a 35% identity with Dicstylstelium D5 protein (51 amino acid overlap). C26R [SEQ ID NO: 3] has 20% identity with EBV GP85 precursor protein (104 amino acid overlap). C27R [SEQ ID NO: 2] has 74% identity with vaccinia 8.3 kD protein (F ORF B) (73 amino acid overlap) and 22% identity with rhinovirus coat proteins (88 amino acid overlap).

Only C2L [SEQ ID NO: 33], C7L [SEQ ID NO: 18], C9L [SEQ ID NO: 20], C12L [SEQ ID NO: 23], C15L [SEQ ID NO: 26], C16L [SEQ ID NO: 27], C17L [SEQ ID NO: 28], C18L [SEQ ID NO: 29], C22R [SEQ ID NO: 7], C23R [SEQ ID NO: 6], C24R [SEQ ID NO: 5], and C25R [SEQ ID NO: 4] were found to have no apparent homologies under the given search parameters.

EXAMPLE 3

Construction of Recombinant Virus

A PRV gp50/63 gene was isolated from Indiana-Funkhauser strain of PRV and was cloned into the Moss vector pGS20 (Dr. Bernard Moss, NIH) behind the 7.5 k vaccinia promoter as described in detail in Kost, T. A. et al. (1989) Virol. 171:365–376. The gene and promoter fragment was then recombined back into the TK region of SPV (strain Kasza; ATCC #VR-363) by transfection, destroying the functionality of the SPV TK gene. Transfection was performed using Lipofectin reagent (Gibco BRL) according to manufacturer's directions (see, Feller, J. A. et al. [1991] Virol. 183:578–585). Thyroidine kinase negative strains of SPV were selected for by growth in a TK⁻ pig kidney cell line (PK-15 cells; ATCC CCL 33) using selective media containing 100 µg/ml 5-bromodeoxyuridine (BUdR) (Boyle et al. [1985] Gene 65:123–128; Weir, J. P. et al. [1982] Proc. Natl. Acad. Sci. USA 79:1210–1214; Wigler, M. et al. [1977] Cell 11:223–232).

The insertion and orientation of the inserted gene was confirmed and expression was evaluated/n vitro using standard methods. Following confirmation of adequate expression and gp50/63 synthesis in vitro the recombinant swinepox-pseudorabies virus (SP-PRV) was expanded, concentrated and titered in PK-15 TK⁻ cells. All trials were conducted within 3 passages of a SP-PRV stock (SP-PRV #10) prepared in PK-15 cells using basal medium Eagle's (BME) supplemented with 0.1 M L-glutamine and 10 per cent fetal bovine serum.

EXAMPLE 4

Virus Isolation

In the following examples, virus isolation was performed as follows. Shedding of SP-PRV in feces were assayed 12 well plates seed with $2 \times 10^5$ PK-15 cells per well using plates using BME supplemented with 5 per cent fetal bovine serum, 0.1M L-glutamine, 300,000 IU penicillin G sodium, 300,000 µg streptomycin sulphate and 750 µg amphotericin B (Gibco). Fetal swabs were thawed at 37° C., vortexed and spun at 3,600 revolutions per minute for 30 minutes before inoculating serial ten-fold dilutions of the supernatant into the wells. After 6 days incubation at 37° C. in a humid, 5% $CO_2$ incubator the media were discarded, plates were washed and fixed in 80% cold acetone. One ml (1:1000 dilution) of a monoclonal antibody specific to PRV gp50 (Mellencamp, M. W. et al. [1989] J. Clin. Microbiol. 27(10):2208–2213) was added to each well and the plates were incubated at 37° C. for 30 minutes. Substrate was discarded and plates were washed. One ml FITC-labeled goat anti-mouse conjugate (Kirkegaard and Perry Laboratories, Gaithersburg, Md. 20879) diluted 1:200 in phosphate buffered saline was added to each well and plates were again incubated at 37° C. for 30 minutes. Excess conjugate was discarded, plates were washed and examined for fluorescence.

Shedding for SP-PRV in pharyngeal swabs was evaluated by the method as described for fecal swabs except that samples were not centrifuged, and 96 well plates containing $3 \times 10^4$ cells per well were used. Serum (1:50 dilution) from a pig that had been hyperimmunized with swinepox virus was used in place of the monoclonal antibody. Following incubation with the SPV hyperimmune serum, the plates were incubated with FITC-labeled goat anti-swine IgG conjugate at 1:200 (Kirkegaard and Perry Laboratories).

Levels of SP-PRV present in the scarification site lesions were assayed as follows. Serial 10-fold dilutions of the nasal swab media (0.1 mL in tissue culture media) were inoculated into 96 well plates containing $3 \times 10^4$ PK-15 cells (ATCC) per well. The plates were incubated at 37° C. in 5% $CO_2$ for 7 days and then examined for cytopathic effect.

Nasal shedding of PRV was assayed from nasal swabs as follows. Serial 10-fold dilutions of the nasal swab media (0.1 mL in tissue culture media) were inoculated into 96 well plates containing $3 \times 10^4$ ST-56 cells (SmithKline Beecham) per well. The plates were incubated at 37° C. in 5% $CO_2$, and examined for cytopathic effect at 72 and 96 hours. Tonsil tissue suspensions, prepared using 2 ml DMEM, were assayed for PRV by inoculation of 2 mL of the tissue suspension in 6 well plates seeded $9 \times 10^5$ ST-56 cells per well. Plates were incubated at 37° C. in a humid, 5% $CO_2$ incubator and were observed daily for cytopathic effect. At the first sign of cytopathic effect or after 5 days incubation the monolayer was scraped off; the cell suspension was frozen at −70° C. The presence of PRV was subsequently confirmed by inoculation of the suspension onto 2-well chamber slides seeded with $3 \times 10^5$ PK-15 cells per chamber. Slides were incubated at 37° C. in a humid, 5% $CO_2$ incubator and were observed daily for cytopathic effect. At the first sign of cytopathic effect or after 5 days the media were discarded, slides were rinsed and fixed in 80 percent cold acetone. One ml of FITC-labeled anti-PRV swine sera (1:100 dilution) was added to each well and incubated at 37° C. for 30 minutes. Conjugate was discarded, slides were washed and examined for fluorescence.

The data were analyzed by analysis of variance of Fisher's Exact test using a proprietary software program (SAS); significance level was set at $p \leq 0.05$.

EXAMPLE 5

Seroconversion and Response to Revaccination
(Trial 1)

Ten 4-week-old pigs (8 males and 2 females) from a PRV negative source were used. Two were purebred Durocs, whereas the others were out of a Duroc x Hampshire x Yorkshire dam sired by a Hampshire boar. One Duroc and 2 crossbreeds (1 with a Hampshire-like phenotype and 1 with a Yorkshire-like phenotype) were assigned to each of groups 1 and 2 (all males). Two crossbreeds (1 male and 1 female) were assigned to each of groups 3 and 4.

Groups 1 and 2 were housed in one room to facilitate containment of the recombinant virus, and groups 3 and 4 in another. Each room was subdivided into 2 pens by a solid wall two feet high and one foot wide. Pigs were fed a commercial ration and had ad lib access to water.

Group 1 pigs were scarified at 2 sites in the inguinal area with 0.2 ml of SP-PRV per site ($1.2 \times 10^6$ PFU per pig).

Group 2 pigs were injected intramuscularly (IM) with 0.8 ml of PS-PRV in the left ham ($2.5 \times 10^6$ PFU per pig). Group 3 pigs were scarified at two sites with 0.2 ml of SPV TK⁻ per site ($2.0 \times 10^6$ PFU per pig) and group 4 pigs were scarified at two sites with 0.2 ml of BME per site. Groups 3 and 4 were removed from the study and groups 1 and 2 were transferred to separate rooms at 29 days post vaccination (dpv). Group 1 and 2 pigs were revaccinated by the original route used at 150 dpv. Groups 1 pigs were scarified in the relatively hairless area behind the left ear with 0.2 ml ($10^{5.4}$ PFU per pig) and group 2 pigs were injected IM in the ham with 1.0 ml ($10^{6.1}$ PFU per pig).

Pigs were observed daily. Body temperatures were recorded daily for 10 days post-vaccination. The scarification sites were almost healed at 6 dpv (groups 1, 3 and 4) when localized lesions typical of swinepox appeared at the sites of scarification in groups 1 and 3. The nature of these lesions was confirmed by histopathology. No swinepox lesions were evident in groups 2 (Sp-PRV IM) or 4 (BME scarified) at this time. At 15 dpv it was noted that pig #403 in group 1 (SP-PRV scarified) had developed lesions extending beyond the sites of scarification. In group 2 (SP-PRV IM), pig #406 had developed several abdominal lesions. All lesions healed spontaneously by 30 dpv. There was no evidence of lesions following revaccination in either group.

Blood samples were collected at approximately weekly intervals starting at −1 days post-vaccination and continuing through 150 days post-vaccination. After revaccination, blood samples were collected at 16 and 36 days when the trial was terminated. Sera were stored at −20° C.

Sera were assayed by serum neutralization (SN) and latex agglutination for the presence of PRV-specific antibodies after the first vaccination. After revaccination (trial 1) and for the subsequent trials sera were assayed by SN only. Pseudorabies virus SN antibody titers were determined in 96-well ST-56 cell-coated plates using standard methods (Hill et al. [1977] *American Assoc. Vet. Lab. Diagnosticians, 20th Annual Proceedings*, pp. 375–377). The Bucharest PRV strain (SmithKline Beecham Animal Health) was used as test virus at a range of 50 to 300 TCID$_{50}$. Multiple dilutions (two-fold or four-fold) were assayed and results were read after 3 to 5 days incubation at 37° C. in a humid, 5% CO$_2$ incubator. Neutralization titers were calculated as fifty per cent endpoints using the Spearman-Karber formula (Schmidt and Emmons [1989] *In Diagnostic Procedures for Viral, Rickettsial, and Chlamydial Infections*, 6th ed., American Public Health Association, Inc., Washington, DC, pp. 18–21). Titers ≥ 1:2 were regarded as positive.

Latex agglutination (LA) was performed on samples diluted 1:4 (Viral Antigens, Inc.). Wells were examined for agglutination at 5, 10 and 15 minutes. Positive and negative controls were assayed.

The following table illustrates the effect of breed and phenotype on pseudorabies virus serum neutralizing antibody titers after initial vaccination with a recombinant swinepox-pseudorabies virus.

TABLE 2

| Group | Pig | Breed | Phenotype | Route of Vaccine | SN titer at 35 days post-vaccine |
|---|---|---|---|---|---|
| 1 | 401 | Duroc | Duroc | Scarified | 1:8 |
| | 402 | Crossbreed | Hampshire | Scarified | 1:8 |
| | 403 | Crossbreed | Yorkshire | Scarified | 1:16 |
| 2 | 404 | Duroc | Duroc | Intramuscular | 1:6 |
| | 405 | Crossbreed | Hampshire | Intramuscular | 1:45 |
| | 406 | Crossbreed | Yorkshire | Intramuscular | 1:128 |

All pigs vaccinated with SP-PRV were positive by PRV SN as of 15 dpv and remained positive for the duration of the trial. Pig #403 (with secondary abdominal lesions) and pig #406 (with primary abdominal lesions) had the highest peak SN titers in groups 1 (SP-PRV scarified) and 2 (SP-PRV IM), respectively (Table 2). The Durocs maintained the lowest SN titers over the course of the first 71 days. Pigs scarified with SP-PRV generally had lower SN titers than IM injected pigs. Control pigs remained negative by SN through 29 dpv when they were removed from the trial. Following revaccination, both groups responded with an anamnestic response.

All crossbreds vaccinated with SP-PRV were positive to LA from 15 dpv. The Durocs, however, remained negative for the duration of the trial. Latex agglutination test results were generally assessed as weak positives with agglutination taking up to 15 min to develop. Samples with SN titers ≥ 1:64 agglutinated rapidly. Control pigs remained negative by LA through 29 dpv.

EXAMPLE 6

Efficacy Following Vaccination by Scarification or Intramuscular Injection (Trial 2)

Thirty-four 4-week-old crossbred pigs were supplied by a PRV negative source, the pigs were out of Duroc sows sired by York x Landrace boars. Breeding stock were vaccinated against leptospirosis and parvovirus only. Pigs were grouped after weaning, ear-tagged at random and assigned as scarified vaccinates (group 1, n=10), intramuscular vaccinated (n=10), controls (group 3, n=10) or in-contact controls (n=4). The pigs were randomized across the two treatment groups by weight, sex and phenotype.

Vaccinates and in-contact controls were housed in plastic bins (Polydome) in a single room. Controls, previously kept separated, were introduced on the day of challenge. Each group was housed in 2 plastic bins; groups 1 and 2 had 6 pigs per bin (5 vaccinates plus 1 in-contact control), whereas group 3 had 5 pigs per bin. Pigs were fed a commercial ration containing 100 grams per ton of chlortetracycline, 0.011 per cent of sulfamethazine and 50 grams per ton of procaine penicillin and had ad libitum access to water.

Group 1 pigs were scarified in the relatively hairless area immediately behind the left ear with 0.25 ml of SP-PRV ($10^{5.4}$ PFU per pig), group 2 pigs were injected IM in the neck on the left-hand side with 1.0 ml SP-PRV ($10^{6.1}$ PFU per pig), whereas controls (group 3) and in-contact controls remained untreated.

All pigs were challenged 21 days post-vaccination by the intranasal administration of virulent pseudorabies virus (PRV) (strain ISU 4892–5) (National Veterinary Services Laboratories, Ames, Iowa). Each pig received 1 ml per nostril of 2 ml total ($10^{7.3}$ TCID$_{50}$ per pig), the administration being timed to coincide with inspiration.

Body temperatures were measured daily (vaccinates) or weekly (controls) before challenge and daily thereafter. Blood samples were collected prior to vaccination and weekly thereafter. Sera were stored at −20° C. Body weights were measured weekly, at the time of death or at termination of the trial. The clinical signs after vaccination were as follows. There were no obvious adverse effects noted after vaccination. Several group 1 and 2 pigs experienced an episode of diarrhea between 3 and 8 dpv which is commonly seen after weaning and is associated with dietary changes. Scarification site lesions typical of swinepox appeared at 5 dpv in group 1 pigs. These were most evident at 7 dpv and healed spontaneously by 13 dpv. There was no extension of scarification site lesions and no lesions developed in IM vaccinated pigs.

A comparison of mean body temperatures by group showed mildly elevated mean body temperatures from 12 through 15 dpv with the group 2 (IM) mean being consistently higher over this period. The group 3 (control) mean body temperature could not be used for comparison since they were housed under different environmental conditions before challenge.

From 7 to 14 dpv, group 2 (IM) pigs had the lowest mean body weight gain. Gains from 1 to 7 dpv and from 14 to 21 dpv in this group and gains from 0 to 21 dpv in the other groups were unremarkable.

Following challenge, several pigs showed clinical signs typical of pseudorabies, characterized by central nervous system (CNS) signs (ataxia, circling, posterior paresis, convulsions) and/or respiratory signs (sneezing, coughing, dyspnea). The incidence of clinical disease for the 10-day period after challenge is shown in Table 3.

TABLE 3

|  | CNS system signs | Resp. signs | CNS system and/or resp. signs | Survival rate |
| --- | --- | --- | --- | --- |
| Scarified | 33 | 33 | 40 | 90 |
| Intramuscular | 20 | 20 | 33 | 90 |
| Control | 70 | 50 | 90 | 80 |

Slightly fewer group 2 (IM) pigs showed clinical signs than group 1 (scarified) pigs (33 versus 40 per cent). In contrast, 90 per cent of the controls showed clinical signs typical of pseudorabies. One group 2 (IM) pig died of respiratory disease 5 days post challenge (dpc). At 5 dpc a group 1 (scarified) and a control pig with severe CNS signs were euthanized and a control pig died after showing CNS signs; there were no further deaths. Pigs that developed clinical disease generally showed the same extent and severity of clinical signs irrespective of their group.

After challenge, the mean body temperature of groups 1 (scarified) and 2 (IM) peaked at 3 dpc after which it steadily decreased to reach approximately normal levels of 7 dpc. The mean body temperature of group 3 (control) plateaued at a similar temperature from 3 through 5 dpc when it decreased; the mean body temperature of this group remained consistently highest after challenge.

The effect of challenge on mean body weight by group is illustrated in Table 4. Specifically, the following table provides data representing the growth performance of pigs vaccinated with a recombinant swinepox-pseudorabies virus by scarification or intramuscular injection for the seven day period after challenge with virulent pseudorabies virus.

TABLE 4

| Parameter | Scarified | I.M. | Control |
| --- | --- | --- | --- |
| Gain[1] | −0.05 | 0.32 | −0.68 |
| Average daily gain[2] | −0.01 | 0.04 | −0.10 |
| Percentage gain[3] | 0.39 | 3.31 | −5.55 |
| Percentage average daily gain[4] | 0.00 | 0.41 | −0.84 |
| % of pigs that maintained or lost weight | 40 | 20 | 100 |

[1](weight at end of period − weight at beginning of period)
[2](weight at end of period − weight at beginning of period)/number days in period
[3](weight at end of period − weight at beginning of period)/weight at beginning of period*100
[4](weight at end of period − weight at beginning of period)/weight at beginning of period*100/number of days in period During the first 7 dpc group 1 (scarified) maintained its mean body weight, the group 2 (IM) mean increased, whereas the group 3 (control) mean decreased. During this period, 40, 20 and 100 percent, respectively of pigs in groups 1 (scarified), 2 (IM) and 3 (controls) lost or maintained their body weight (Table 4). During the second 7-day period after challenge all surviving pigs showed similar weight gains. Controls, however, never made up for the weight loss during the first 7-day period after challenge.

After vaccination, the serology tests showed a PRV SN antibody response in 70 and 90 percent of group 1 (scarified) pigs at 14 dpv (range—1:2 to 1:8) and 21 dpv (range—1:2 to 1:16), respectively and in 90 and 100 percent of group 2 (IM) pigs at 14 dpv (range—1:2 to 1:8) and 21 dpv (range—1:2 to 1:128), respectively. Group 2 (IM) pigs had the higher geometric mean liter at either sampling (Table 4). All pigs were negative before vaccination; group 3 (control) pigs and in-contact controls remained negative through 21 dpv.

TABLE 5

| | Days post vaccination | | | | | |
| --- | --- | --- | --- | --- | --- | --- |
| Group | 0 | 7 | 14 | 21[1] | 28 | 35 |
| Scarified (10) | <1:2 | <1:2 | 1:2 | 1:5 | ≧1:1756(9) | ≧1:5161(9) |
| IM (10) | <1:2 | <1:2 | 1:4 | 1:18 | ≧1:2048(9) | ≧1:5161(9) |
| Control (10) | <1:2 | <1:2 | <1:2 | <1:2 | 1:7(8) | ≧1:152(8) |

[1]Day of challenge
Sample size in parentheses.

After challenge Group 1 (scarified) and 2 (1M) pigs responded by 7 dpc with a marked increase in the geometric mean PRV SN titer (anamnestic response) (Table 6). Controls showed a response typically seen in naive pigs. None of the in-contact controls showed evidence of an anamnestic response.

Fetal swabs were collected for SP-PRV isolation in 2 ml Dulbecco's MEM (DMEM) from all vaccinates at 0, 3, 6, 9 and 12 dpv and stored at −70° C. The DMEM was supplemented with 0.1M L-glutamine, 300,000 IU penicillin G sodium, 300,000 μg streptomycin sulphate and 750 μg amphotericin B. Skin scrapings were collected for SP-PRV isolation in 2 ml supplemented DMEM from 4 scarified pigs on the day that scarification site lesions appeared and every 3 days thereafter until 21 dpv and stored at −70° C. Nasal swabs were collected for PRV isolation in 2 ml supplemented DMEM on the day of challenge and daily thereafter; both nostrils were probed with a single cotton-tipped swab. Tonsil tissue samples were collected from all pigs that died, and from two pigs per group at termination of the trial, and stored at −70° C.

TABLE 6

Isolation of recombinant swinepox-pseudorabies virus from skin scrapings taken at the site of scarification.

| Pig | Phenotype | Days post vaccination | | | |
|-----|-----------|-----|------|------|------|
|     |           | 5   | 7[1] | 10   | 13   |
| 58  | White     | 2.8 | ≦1.8 | <1.5 | <1.5 |
| 59  | Red/white | 3.5 | ≦1.8 | <1.5 | <1.5 |
| 75  | White     | 3.5 | 2.8  | <1.5 | <1.5 |
| 80  | Red       | 4.0 | 3.3  | ≦1.8 | <1.5 |

[1]Swinepox-like lesions most evident (prior to scab formation).

Titer of SP-PRV at the site of scarification was highest when lesions become noticeable at 5 dpv. SP-PRV was not detected in skin scrapings taken at 13 DPV (Table 6). There was no detectable fecal shedding of SP-PRV in group 1 (IM) pigs. Although toxicity was experienced during the evaluation of faecal swabs, 50 per cent of the swabs collected from group 2 (IM) pigs at 3 dpv could be evaluated for cytopathic effect; all were negative. Further evaluation of fecal swabs were not pursued.

TABLE 7

Isolation rates of pseudorabies virus from pigs vaccinated with a recombinant swinepox-pseudorabies virus by scarification or intramuscular injection and challenged 21 days later with virulent pseudorabies virus.

| Group | Days post challenge | | | | | | | | | | | | Mean |
|-------|---|---|---|---|---|---|---|---|---|---|----|----|----|
|       | 0 | 1 | 2 | 3 | 4 | 5 | 6 | 7 | 8 | 9 | 10 | 11 | 12 days[1] |
| IM       | 0 | 60  | 100 | 100 | 80  | 67  | 0   | 0  | 0  | 0  | 0  | 0  | 0  | 4.0 |
| Scarified| 0 | 80  | 100 | 100 | 100 | 80  | 0   | 0  | 0  | 0  | 0  | 0  | 0  | 4.6 |
| Control  | 0 | 100 | 100 | 100 | 100 | 100 | 100 | 63 | 50 | 38 | 25 | 25 | 13 | 8.5 |

[1]Mean number of days that pseudorabies virus was shed by pigs surviving challenge.

Following challenge, the geometric mean virus titer of PRV shed in nasal swabs collected daily was determined. Group 1 (scarified) and 2 (IM) pigs showed a similar pattern, shedding lower levels of PRV over a shorter period of time compared to controls. Group 1 (scarified), 2 (IM) and 3 (controls) shed PRV for an average of 4.6, 4.0 and 8.5 days, respectively (Table 7). Although groups 1 and 2 showed a similar shedding pattern, isolation rates show that fewer group 2 (IM) pigs were shedding PRV than group 1 (scarified) pigs.

Pseudorabies virus was isolated from the tonsil tissue of all pigs, vaccinated with a recombinant swinepox-pseudorabies virus by scarification or intramuscular injection and challenged 21 days later with virulent pseudorabies virus, that died or were euthanized due to pseudorabies and from the two controls sampled at termination of the trial (Table 8). None of the vaccinates sampled at termination of the trial (two pigs per group) were positive.

TABLE 8

| Group     | Pig | Cause of death           | Result |
|-----------|-----|--------------------------|--------|
| Scarified | 65  | Euthanized due to disease | +      |
|           | 60  | Euthanized at termination | −      |
|           | 77  | Euthanized at termination | −      |
| IM        | 68  | Died due to disease       | +      |
|           | 57  | Euthanized at termination | −      |
|           | 71  | Euthanized at termination | −      |
| Control   | 88  | Euthanized due to disease | +      |
|           | 91  | Died due to disease       | +      |
|           | 84  | Euthanized at termination | +      |
|           | 92  | Euthanized at temrination | +      |

Table 9 below provides results of the isolation of pseudorabies virus from tonsil tissue of pigs vaccinated with a recombinant swinepox-pseudorabies virus by scarification or intramuscular injection and challenged 21 days later with virulent pseudorabies virus.

TABLE 9

| Group   | Pig    | Cause of death            | Result |
|---------|--------|---------------------------|--------|
| SPV TK+ | No tag | Died due to disease       | +      |
|         | 89     | Euthanized at termination | −      |
|         | 107    | Euthanized at termination | +      |
| SPV TK− | 85     | Euthanized due to disease | +      |
|         | 95     | Euthanized due to disease | +      |
|         | 118    | Euthanized due to disease | +      |
|         | 102    | Euthanized at termination | +      |

TABLE 9-continued

| Group | Pig | Cause of death | Result |
|---|---|---|---|
| | 107 | Euthanized at termination | + |
| SP-PRV | 93 | Euthanized at termination | + |
| | 101 | Euthanized at termination | + |
| Control | 81 | Died due to disease | + |
| | 83 | Died due to disease | + |
| | 100 | Euthanized due to disease | + |
| | 116 | Died due to disease | + |
| | 90 | Euthanized at termination | − |
| | 99 | Euthanized at termination | − |

EXAMPLE 7

Efficacy Following Oral Vaccination (Trial 3)

Thirty-nine 3-week-old crossbred pigs were supplied by the same as for trial (Example 6). Pigs were assigned as SPV TK$^+$ vaccinated (group 1, n=6), SPV TK$^-$ vaccinates (group 2, n=6), SP-PRV vaccinated (group 3, n=10), controls (group 4, n=10) or in-contact controls (n=2). Grappa pigs were randomized across the three treatment groups by weight, sex and phenotype.

Pigs were housed in plastic bins (Polydome) in a single room. The control group was introduced on the day of challenge. Groups 1 and 2 were housed in separate bins (6 pigs per bin). Groups 3 and 4 were each housed in two bins. Group 3 had 5 vaccinates plus 1 in-contact control per bin before challenge. The in-contact controls were removed immediately before challenge. Group 4 (control) had 6 pigs per bin before challenge and 5 pigs per bin post challenge. Pigs were fed a commercial pig ration containing 100 grams per ton of chlortetracycline, 0.011 per cent of sulfamethazine and 50 grams per ton of procaine penicillin and had ad lib access to water.

Group 1 pigs received one ml of SPV TK$^+$ ($10^{6.7}$ PFU per pig), group 2 pigs received one ml of SPV TK$^-$ ($10^{6.3}$ PFU per pig) and group 3 pigs received one ml of SP-PRV ($10^{6.1}$ PFU per pig) squirted into the oral cavity with a syringe. Controls and in-contact controls remained untreated. Three pigs housed in a separate bin were scarified behind the left ear on the day of vaccination; each pig received one of the three inocula.

All pigs were challenged 21 dpv by the intranasal administration of virulent PRV (strain ISU 4892-5) [National Veterinary Services Laboratories, Ames, Iowa]. Each pig received 1 ml per nostril or 2 ml total ($10^{7.1}$ TCID$_{50}$ per pig), the administration being timed to coincide with inspiration.

Body temperatures were measured daily (vaccinates) or weekly (controls) before challenge and daily thereafter. There were no obvious adverse effects noted after vaccination. Pigs in all groups experienced episodes of diarrhea between 1 and 3 dpv, which is commonly seen post-weaning and is associated with dietary changes, and again between 10 and 17 dpv. Group 1 (SPV TK$^+$) pigs were most affected between 10 and 17 dpv. Since several pigs had weeping lesions on the ears from fighting, and were still fighting at the time of oral vaccination, there was a concern that pigs could effectively scarify one another. However, no lesions developed on the ears, or elsewhere on the body, of pigs in any of the vaccinated groups.

Mildly elevated mean body temperatures were observed from 8 through 21 dpv for the vaccinated groups. The group 3 (control) pigs were housed under similar environmental conditions, but were only monitored weekly before challenge.

From 7 to 21 dpv, group 1 (SPV TK$^+$) pigs had the lowest mean body weight gain. Mean body weight gain for this group from 0 to 7 dpv and for the other groups from 0 to 21 were unremarkable.

Following challenge, several pigs showed clinical signs typical of pseudorabies, characterized by central nervous system (CNS) signs (ataxia, circling, posterior paresis, convulsions) and/or respiratory signs (sneezing, coughing, dyspnea). The incidence of clinical disease for the 10-day period after challenge is shown in Table 10. Table 10 shows the results of pseudorabies disease incidence and survival rates of pigs vaccinated orally with a recombinant swinepox-pseudorabies virus and challenged 21 days later with virulent pseudorabies virus.

TABLE 10

| Group | CNS system signs | Respiratory signs | CNS system and/or resp. signs | Survival rate |
|---|---|---|---|---|
| SPV TK$^+$ | 67 | 33 | 67 | 83 |
| SPV TK$^-$ | 100 | 33 | 100 | 33 |
| SP-PRV | 50 | 50 | 60 | 100 |
| Control | 100 | 30 | 100 | 50 |

Slightly fewer group 2 (SP-PRV) pigs shows clinical signs than group 1 (SPV TK$^+$) pigs (60 versus 67 per cent). In contract, 100 per cent of group 2 (SPV TK$^-$) pigs and controls showed clinical signs typical of pseudorabies. Three group 4 (control) pigs showing severe CNS signs died at 6 dpc, two group 2 (SPV TK$^-$) pigs showing severe CNS signs were euthanized as well as a group 4 pig showing both severe respiratory and CNS signs. At 7 dpc a group 1 (SPV TK$^+$) and group 4 (control) pig died after both showed severe respiratory and CNS signs, a group 2 (SPV TK$^-$) pig died after showing CNS signs and another was euthanized after showing severe CNS signs; there were no further deaths. Pigs that developed clinical disease in groups 2 (SPV TK$^-$) and 4 (control) soon after challenge showed more severe clinical signs. However, although all group 3 (SP-PRV) pigs survived and only one group 1 (SPV TK$^+$) pig died, pigs with clinical signs in either of these groups still showed clinical signs after the majority of surviving pigs in groups 2 (SPV TK$^-$) and 4 (control) pigs had recovered. In addition, 2 pigs in group 3 (SP-PRV) developed severe ocular lesions (one pig was blind, the other semi-blind). Similar, but milder, lesions which healed were observed in one pig in each of groups (SPV TK+), 2 (SPV TK$^-$) and 4 (control). Pseudorabies virus was isolated from ocular swabs taken from one of the group 3 (SP-PRV) pigs at termination of the trial (titer=3.8 log$_{10}$ TCID$_{50}$).

The mean body temperatures of groups 1 (SPV TK$^+$) and 3 (SP-PRV) plateaued from 2 through 6 dpc after which they gradually decreased to reach approximately normal levels at 12 dpc. The mean body temperatures of groups 2 (SPV TK$^-$) and 4 (controls) peaked at a higher temperature at 2 dpc after which they steadily decreased to approximately normal levels at 7 dpc. Prior to 5 dpc groups 2 (SPV TK⁻) and 4 (control) had the highest mean body temperature, from 5 through 12 dpc groups 1 (SPV TK⁺) and 3 (SP-PRV) generally had the highest mean body temperatures. Table 11 shows the results of growth performance of pigs vaccinated orally with a recombinant swinepox-pseudorabies virus for the seven day period after challenge with virulent pseudorabies virus.

TABLE 11

| Parameter | SPV TK⁺ | SPV TK⁻ | SP-PRV | Control | Unchall.[5] |
|---|---|---|---|---|---|
| Gain[1] | 0.11 | −1.17 | −0.36 | −1.80 | 4.66 |
| Avg daily gain[2] | 0.02 | −0.18 | −0.05 | −0.27 | 0.67 |
| % gain[3] | 2.04 | −9.73 | −2.35 | −11.48 | 31.25 |
| % average daily gain[4] | 0.29 | −1.49 | −0.36 | −1.74 | 4.46 |
| % or pigs that maintained or lost weight | 50 | 83 | 70 | 90 | 0 |

[1](weight at end of period − weight at beginning of period)
[2](weight at end of period − weight at beginning of period)/number days in period
[3](weight at end of period − weight at beginning of period)/weight at beginning of period*100
[4](weight at end of period − weight at beginning of period)/weight at beginning of period*100/number of days in period
[5]Two pigs from the same farrowing group were housed with the control group prior to challenge with pseudorabies virus; these were not transferred to the room containing the vaccinates and were not challenged with pseudorabies virus.

During the first 7 dpc group 1 (SPV TK⁺) maintained its weight, the group 3 (SP-PRV) mean showed a slight decrease, whereas the groups 2 (SPV TK⁻) and 3 (control) means decreased sharply. During this period, 50, 83, 70 and 90 per cent respectively, of pigs in groups 1 (SPV TK+), 2 (SPV TK⁻), 3 (SP-PRV) and 4 (controls) lost or maintained their body weight (Table 11). During the second 7-day period post challenge all surviving pigs showed similar weight gains, except for the 2 remaining pigs in group 2 (SPV TK⁻) which barely gained weight.

Blood samples were collected prior to vaccination and weekly thereafter; sera were stored at −20° C. Body weights were measured weekly, at the time of death or at termination of the trial. A PRV SN antibody response was not evident in group 3 (SP-PRV) pigs at 14 or 21 dpv. All pigs were negative prior to vaccination; group 1 (SPV TK⁺), 2 (SPV TK⁻), 4 (control) pigs and in-contact controls remained negative through 21 dpv.

All groups responded to challenge showing a response typically associated with naive pigs (Table 12). None of the in-contact controls showed evidence of an anamnestic response. Table 12 shows the results of pseudorabies virus serum neutralizing antibody titers (geometric means) of pigs vaccinated orally with a recombinant swinepox-pseudorabies virus and challenged 21 days later with virulent pseudorabies virus.

TABLE 12

| Group | Days post vaccination | | | | | |
|---|---|---|---|---|---|---|
|  | 0 | 7 | 14 | 21[1] | 28 | 35 |
| SPV TK⁺ (6) | <1:2 | — | — | <1:2 | 1:7(5) | 1:111(5) |
| SPV TK⁻ (6) | <1:2 | — | — | <1:2 | 1:11(2) | 1:181(2) |
| SP-PRV (10) | <1:2 | <1:2 | <1:2 | <1:2 | 1:13(10) | 1:128(10) |
| Control (10) | <1:2 | — | — | −1:2 | 1:9(5) | 1:128(5) |

[1]Day of challenge.
Sample size in parenthesis.
— Not tested

Fecal swabs for SP-PRV isolation and pharyngeal swabs for SP-PRV and SPV isolation were collected in 2 ml supplemented DMEM from all vaccinates at 0, 3, 6, 9 and 12 dpv and frozen at −70° C. Since the toxicity associated with the fecal samples as described in trial 2 could not be resolved, the group 3 (SP-PRV) fecal samples were not assayed for the presence of SP-PRV. Nasal swabs and tonsillar tissue samples were collected as described for trial 2. Evaluation of pharyngeal swabs showed only one SPV TK⁺ vaccinate with a positive swab at 3 dpv. No virus was detected in any other pigs at this or later samplings.

After challenge, all groups showed a similar pattern of shedding although groups 1 (SPV TK⁺) and 3 (SP-PRV) peaked at a lower level. Group 1 (SPV TK⁺), 2 (SPV TK⁻), 3 (SP-PRV) and 4 (control) shed PRV for an average of 8.4, 9.0, 6.9 and 7.2 days, respectively (Table 13). From the isolation rates it appears that shedding was delayed in group 3 (SP-PRV). This group also consistently had the lowest geometric mean titer as of 5 dpc.

TABLE 13

Isolation rates of pseudorabies virus from pigs vaccinated orally with a recombinant swinepox-pseudorabies virus and challenged 21 days later with virulent pseudorabies virus.

| Group | Days post challenge | | | | | | | | | | | | Mean |
|---|---|---|---|---|---|---|---|---|---|---|---|---|---|
|  | 0 | 1 | 2 | 3 | 4 | 5 | 6 | 7 | 8 | 9 | 10 | 11 | 12 days[1] |
| SP-PRV | 0 | 50 | 70 | 100 | 100 | 100 | 100 | 80 | 40 | 30 | 10 | 10 | 0 | 6.9 |
| SPV TK⁺ | 0 | 20 | 100 | 100 | 100 | 100 | 100 | 80 | 60 | 80 | 40 | 20 | 20 | 8.4 |
| SPV TK⁻ | 0 | 80 | 100 | 100 | 100 | 100 | 100 | 100 | 100 | 100 | 50 | 0 | 0 | 9.0 |
| Control | 0 | 70 | 100 | 100 | 100 | 100 | 100 | 80 | 40 | 40 | 20 | 0 | 0 | 7.2 |

[1]Mean number of days that pseudorabies virus was shed by pigs surviving challenge.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 14176 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 3852..4226

( i x ) FEATURE:
        ( A ) NAME/KEY: CDS
        ( B ) LOCATION: 4585..4887

( i x ) FEATURE:
        ( A ) NAME/KEY: CDS
        ( B ) LOCATION: 5131..5310

( i x ) FEATURE:
        ( A ) NAME/KEY: CDS
        ( B ) LOCATION: 5760..5912

( i x ) FEATURE:
        ( A ) NAME/KEY: CDS
        ( B ) LOCATION: 6786..7130

( i x ) FEATURE:
        ( A ) NAME/KEY: CDS
        ( B ) LOCATION: 10148..10513

( x i ) SEQUENCE DESCRIPTION: SEQ ID NO:1:

```
AAGCTTTAAT  CCTCCTCATC  CTCCAAGTCA  TTCCTTCTAT  CTCCCTGGTA  TTGTAAAACA        60
GGCTCAGGTC  CCGAGCAGTT  TACACATCTA  TATATGCTTG  GTTCTAACGT  ACTATGAAAT       120
CCAACACATG  CTATTCTATT  AGACATGATA  GTTGGTACCA  TAACCCTAGG  TGATGATGTA       180
AATAAATATT  TATCACCTAA  TCTCCTAGTT  ATAGTCGGAT  ATCCTGGTTC  ACCCGGTAGA       240
TAGTCCGTAT  CAGGAAGCAA  TTCATTTACG  TACGGATCAT  AACGATAGTC  CGGAGCAAAG       300
TCCTCGATGT  TATACCATTT  AACAGCGACC  GACGACGGAT  AATGATTATC  AAATGTGCAT       360
ATCAATGTAG  TATTATCTCC  TCTTTCAATT  CCTGTAACTG  TAACAGTAGG  CTTAACTGGC       420
TTATCTATAT  ATCCCTTAGA  AATTTTATAA  TAATCATCCG  CTGTAAACGG  ACATGTTAAT       480
GTTACCATTG  ATCCAAGATG  TTCCATAACA  CGTTCCCAGT  GTTGTGATTT  AACAGTTAAC       540
ATTCCTACCT  TTGGAAATGT  ACGTGATCTA  ACTTACTAA   AGCGTTTATT  CTTGGGGTCG       600
AATCGTGTCC  ATATATTACC  ACCTACAGTA  ACATAACCGA  AATTTACTTG  AAGTTGTCTT       660
AGATCAGTAC  ATCCAATTGT  CAAGGACATA  GTCTTGTAAG  GATTACTCGT  TTCTGGAAGT       720
TTATTTATCT  CATCTAGCGT  TTCACTCATT  CTATTTAGCC  AGAACATAAA  ATTATAATTA       780
TTTTTCGGAT  AAATATCTAAT  CTTAGTCTCA  TTAAACCATG  TTGGTGGTTC  ATTTCTTAAT      840
```

```
TCTGGTCTTC CTGTCTCGCT ATTTAGTTTT AAACGTTTTA TTAGTATATC ATTAAAATAA    900
TCGGTGACTT CGAAGTCATA TCGATGATTA TCATCTTGTA AAGTATATGT ATAATTGTAT    960
ACTAAGAATG CGGAAGCATC TACATATGCT GTAATAATAG ACAATATCAC AATCGCTTTA   1020
GTAATCATTA TGATTTATTT TTGGAATATT ATTTCAATTA TAAAGAGAT TATCCGAACC    1080
AACCAGAAAA GAAACCTTCT TTTTCTTTG TTTCCTCTTT TCTAAACGGA TTTAGACTAG    1140
ATAGAAAAGA CTCCCTACGC TTTTCCTTTT TAAAGGGATT TATACTATCC AGCGACAGCC   1200
AACCTCTGTT AGATATCAGA GAGTATGGAT TCACCGCACG AAGTAAAAAA ATCATTATTT   1260
TCATAAGTAT ATATGTAAGC AGCTTAGATA CATTTCCTAA TATAAAGTAT ACAATACTTA   1320
GCAAAGGATT AATAATATAC GATAGCATGA TTACGTAATG ATTATTTATA ACTTGTGTTT   1380
TGTAAGAAAA TAACAACTAA ATAATATTGC TACTGCTAGA AGATTTTCGT GAAAAGAGTT   1440
TTTTCCTAAT CCTATTGTCT CTATATATAC ACGAACATAT GCTAGATATA CGAGATCGAA   1500
CATGTTCACC TATCAGTGTA TATATTATTG GATTATACA CAACGCGCT AACGAGATAG    1560
TCTCCGAAAA GGTGATCGCA TAGGCCAGGT TTAGATAGAG GCACAGATGT CTAAATATAT   1620
TAGATGTATA TAAGCTAACA ATCGTCGCTA TCATTAGAAC GATATAGAGC GGAATCCAAC   1680
ATATTAGAGA ACATACAACA ATCATTAATA CAATTTTTAT AGATTTATAC TTTCGTCTAT   1740
TTCTTAATCT AACCACTGTA GAAAAAATTC TATAATAGCA ATATACGAAT ATGATTATAG   1800
GTATCAGGAA TCCCAATATA GTGATCTCTA TTTGCATCAG TCTTTTATG AATGCGATTA    1860
TGGAGTCATT CTCGTTCGTC AGAGTACATT GGTATATATC TTTAGACATA TGAGGAATAT   1920
TCTCGTATAG TTTAGATACG GGACTAGATA ATATCAAGGA TAATAACCAA GCGGAACAGC   1980
ACATAAGGAT ACCTATACGT TTCGTCCTAT ACGGTTGTCG CTTTATAGGA TGAACGATCG   2040
CAAAATATCT ATCTATACTC ATAAGTGTTA TTATAAACAT ATTACTAAAG AATCCTACGT   2100
AGTATAATAC GGACATTATT TTACATAGTA TATTCCCAAA AATCCATTGA TCGAGTTTAC   2160
TATACACAAT GAACGGAATC TGAAATACGA ATATACAATC TGACATAGAT AGATTAAGAA   2220
TATAGATGTC TGTTATGGAT TTGTTTCTTT TGAACGCTAT AAGGGATACT ACAAATATAT   2280
TGCCGATGCT TCATTAACAC ATTCTTCAAA CTTAGGAATA TCGTTTAAAC GCTTCCATGT   2340
ATTTTTTAAT TTATTGTACT TTTCTACACT GTTTGTATTA TATCCACCTA TTATATATAA   2400
TTCATTATTA AAAACACACG ATAGACAAAA TGATCTTTTT ACATTTGTAT TTGATAAATA   2460
TTTCCAACAA TCATCTCTTG AAGAATATAT ATAAACATCG TTAGTGTGTT CTATACTTAT   2520
ATGTGGTGTA TCTATACGAC CACCTATACA GTATATAAAA TCGTTATATA CTATGGATGA   2580
TATACCACTC TTTGCTATGG GAAATTGTTT TAACTTCATC CATGAATGAT CGGTCAGTTT   2640
CTCTACGGCA TCGTCTGATA CAATCATTTC TATATTAAAT TCATCCGTTA TTGATGTTTT   2700
TAATCCACCT ATTGTATATA CTTCATTATT ATAGTCTACC AACGACATAT AACATCTAGG   2760
ATAACACAAA TGTTGACCAT CATACCATGA TTTCCATTCA GGTTTCCAAA ATTCTACGAT   2820
GTTTGTCATA TATCCATTTG TATCTTTTCC ACCAATTGAA TATATCATCC CATTTGATAC   2880
ACATACAGAT GTATCGTATC TAAAATAATT TAATTCTGGT TCGTAACACC ATAATTTGTT   2940
TTTTATATTA TATGACAACA CCTCTTTAGT GAAATATCCT CGTTCTTTC CACCGATAAT    3000
ATATAGTATA CTATTTAAGT ATACAACACT AAAATGAGTT TTACAACCAA ACATATCATC   3060
GTATCTGTCT ATAATATGTT TTTTATTCGA TAACGGATTG AATGCGGTTA TATTAAATAT   3120
CTTTTTTCCT CCTACCATTA TTATAAAGTT ATGTGATATA TCTACATCGT GTTCTTTGTT   3180
ATCATATATT CGTTCCCGTA TATTATTGTA CAATTCAATA TCCGATAAGG ATGTATAATG   3240
```

```
GTCTTGATCA TTGATATGTT TCATTAATTT TTTAGTATAA ATAATTCGTT CATCTTTATG    3300

AACGATCCAA TTTAATATTA TTTTTTTAAC TATATATTCA CATGCAATGT ATTTAATTTC   3360

TTTTATAATT AATATCATAT CATCTATATC TAATTCTACT ACCAGTTTGT TATTATTTAT   3420

TATTTTTGGT AAATACCATT TTGACATTTC ACGTAATCGT TGTAGATTGT AAGTATCTGA   3480

AAAGTTTAAG AGATGTATAC AATTTGTTTC ATCTATTATA CCGCATATAT ATTCTTCACA   3540

TATTTTTATT AAAGAATCTA TACATAGATA ATCACAGACT TGTATTACTA ATTCTATATT   3600

ATCCTTTGTT AGTACTATAT TACCGGTGTA CATAAATTCC AATATAATAT ACAATATATC   3660

ATAATCGGCG CATATATAGA TTTCATCATT ATTTTTATCA ATAAAATCTG AATTAAATAT   3720

ATTATAAAAG TACTTAGAGT ACATAGATAA TATTAACCTA TGTGCGCTAA TGGTTTTATT   3780

ATTCTCTATG GATACTATTT TTATATCACA CATAATTCCA TGTTTAAAAA AATCATGTAA   3840

TCGTAATAAT A ATG AAT TCA TGT TAT GAT AGA TTT AGG ATT ATT TTT CAA    3890
             Met Asn Ser Cys Tyr Asp Arg Phe Arg Ile Ile Phe Gln
              1               5                  10

AAA AAA AAC AAT TAT TAT TGT AAG TAT AAT GAT TGT ATG AGA TAT TTT          3938
Lys Lys Asn Asn Tyr Tyr Cys Lys Tyr Asn Asp Cys Met Arg Tyr Phe
         15              20              25

TTG AAT ATT AGT CTA TAT CTT ATA CTT ATT TGT GAA AAG AAT ATA ACA          3986
Leu Asn Ile Ser Leu Tyr Leu Ile Leu Ile Cys Glu Lys Asn Ile Thr
 30              35              40                      45

TCA AAA TCT ACG TCG ATT ATT TTC GAT GAT AAT ATA GCA AAC ATA CCT          4034
Ser Lys Ser Thr Ser Ile Ile Phe Asp Asp Asn Ile Ala Asn Ile Pro
             50              55                      60

ATA GAA GAC TTA CAA TGT TTA ATT ATA TCA TCT TTA CAT TTT AAA CGT          4082
Ile Glu Asp Leu Gln Cys Leu Ile Ile Ser Ser Leu His Phe Lys Arg
         65              70              75

ATG TTA ATG GAT ATA GTA TCT CCC TCT TTG TAT GTA TTT ATA ATA TCA          4130
Met Leu Met Asp Ile Val Ser Pro Ser Leu Tyr Val Phe Ile Ile Ser
         80              85              90

TTA TAT ATA TAT TTT GTA GCT AAT ATA TCA TAT TTC ATG AGT TCC TTA AAT      4181
Leu Tyr Ile Tyr Phe Val Ala Asn Ile Ser Tyr Phe Met Ser Ser Leu Asn
         95              100             105                 110

AAC TTA CCA CAT GCG CAT GTG TTG TTA TAT TTT TTT CTC CAA TGAAGATACA       4233
Asn Leu Pro His Ala His Val Leu Leu Tyr Phe Phe Leu Gln
             115             120                 125

TAAATATAAT ATCATCTATA CTATGATATT TATTAATCTT ATCTAATATA GTATAATTTA   4293

TCTTCTTATT TTTATAATTT GATTTTTTA AAAGATATTC GTATTCGCTA TAAATAATAG    4353

ATGCCACATT CATATGATTA GGTACAACGG TCATGATATC ATAAAATAGT CTAAGATCAC   4413

AAAAATTGAA TTCCTCATCT ATTATTCTTA TTACTTCTTT TCTAGATGGA TTTTTATCAT   4473

CTTGAGAAAA ATCTACATTT AATCTAAATA CAGCACAAAA ATGCTTATAC TCATCCTTAT   4533

TTAATTTTCT TATGTATTTT CTTATAATTC TTCCAGATCT ATAATCACGT A ATG AAT     4590
                                                          Met Asn
                                                           1

TTT TTA TTA CAA TAT ACG AAT TCA TTC CTT TAT CTT TAT AAA CGT ATT          4638
Phe Leu Leu Gln Tyr Thr Asn Ser Phe Leu Tyr Leu Tyr Lys Arg Ile
         5               10              15

TAC TGT TCA GTA TTT ACC ATA AGT TCT TGC AAT ATT AGT TTA AAC GAA          4686
Tyr Cys Ser Val Phe Thr Ile Ser Ser Cys Asn Ile Ser Leu Asn Glu
     20              25              30

GAT AAT ATA TTA TTA TAT AAG TGC ATA AAC TTT GAC GAT ATA TTG GAT          4734
Asp Asn Ile Leu Leu Tyr Lys Cys Ile Asn Phe Asp Asp Ile Leu Asp
 35              40              45                      50
```

| | | | | | | | | | | | | | | | | |
|---|---|---|---|---|---|---|---|---|---|---|---|---|---|---|---|---|
| TCA | TAT | TTA | TCA | CTT | ACA | ACT | CTA | TAT | AAT | CTG | TTA | TTA | ACT | CTA | TCT | 4782 |
| Ser | Tyr | Leu | Ser | Leu | Thr | Thr | Leu | Tyr | Asn | Leu | Leu | Leu | Thr | Leu | Ser | |
| | | | | 55 | | | | 60 | | | | | | 65 | | |
| ATA | TCA | TCG | AAA | TCT | TTA | ATA | AAA | TAT | GTA | TCG | ATT | TTT | CTT | GGA | ATT | 4830 |
| Ile | Ser | Ser | Lys | Ser | Leu | Ile | Lys | Tyr | Val | Ser | Ile | Phe | Leu | Gly | Ile | |
| | | | 70 | | | | | 75 | | | | | 80 | | | |
| AAT | CCA | TCT | ACA | CAC | ACT | CTA | GTA | CTA | TTA | TCT | GTT | TTT | TTT | GGA | CCA | 4878 |
| Asn | Pro | Ser | Thr | His | Thr | Leu | Val | Leu | Leu | Ser | Val | Phe | Phe | Gly | Pro | |
| | | | 85 | | | | | 90 | | | | | 95 | | | |

| | | | | | |
|---|---|---|---|---|---|
| AAT | TCA | TAATATTGTT | CCATACCCAT | TACATACACA | CAAACGGGTT | CTTGTGATAT | 4934 |
| Asn | Ser | | | | | |
| | 100 | | | | | |

| | | | | | |
|---|---|---|---|---|---|
| AAAGTAAAAT | AAACAATGAA | CATCATCACA | ATATTGATTG | TCTATACTAT | ATGGTATAAT | 4994 |
| TGTATCATTA | ATAATAAATG | TAGCTTCGTA | AATAAATTCA | AATCCACATA | ATGTTATATT | 5054 |
| ATTATATATA | TAATACTGAT | TATCGTATGT | CATTGGATGA | TGTATATCTA | ATAGTATAAT | 5114 |

| | | | | | | | | | | | | | |
|---|---|---|---|---|---|---|---|---|---|---|---|---|---|
| TGAACCATCT | CTTGTC | ATG | TTA | ACA | ATA | GGT | GAA | GTT | ATT | TGT | ACA | ATC | 5163 |
| | | Met | Leu | Thr | Ile | Gly | Glu | Val | Ile | Cys | Thr | Ile | |
| | | 1 | | | | 5 | | | | | 10 | | |
| TCA | CAT | ACT | CTG | CCA | ATA | TTA | TGT | TCA | TTA | GAT | GTC | TTA | TTT | TCA | TAT | 5211 |
| Ser | His | Thr | Leu | Pro | Ile | Leu | Cys | Ser | Leu | Asp | Val | Leu | Phe | Ser | Tyr | |
| | | | 15 | | | | 20 | | | | | 25 | | | | |
| TTA | AAC | CTC | ACC | CAT | GTT | TCA | TCA | TCA | TTG | TCG | ATA | TCA | GAA | TTT | GTT | 5259 |
| Leu | Asn | Leu | Thr | His | Val | Ser | Ser | Ser | Leu | Ser | Ile | Ser | Glu | Phe | Val | |
| | | | 30 | | | | 35 | | | | | 40 | | | | |
| AAA | TTA | CAG | TAT | CCT | AAA | GAA | TTA | GTA | CAA | ACG | GTT | CTC | CAT | TCG | TCA | 5307 |
| Lys | Leu | Gln | Tyr | Pro | Lys | Glu | Leu | Val | Gln | Thr | Val | Leu | His | Ser | Ser | |
| | | 45 | | | | 50 | | | | | 55 | | | | | |

| | | | | | |
|---|---|---|---|---|---|
| TGACTGTACT | GCATTAATTC | TACATCGTAT | GATATTACAT | TATTATCCCA | TTAATTATT | 5367 |
| GTATCAAAAT | CATTAGATGA | TAAAGTAACC | GACGATGGAA | ATACATCGGC | ATTTACTACA | 5427 |
| AATGATAGTG | ATAATATAAT | GAATATGAAA | TGCATGTTTT | ATTATAAAAA | TAGATTAAAT | 5487 |
| TTTCACTTTA | AAGTTCATAA | ATCGTATCGT | ATGTGTTGTT | TTTAGCGGAA | ATCTTACAAT | 5547 |
| ATTTATATAG | ATAAACTATC | AGCGTTATGA | ACGATATACA | AGTTATGACA | AATGGTAATA | 5607 |
| AGTAGAATAT | CATCGTAACC | AGCTTAAATG | AAACATCATT | TTTTGATGTA | TCTATTATTT | 5667 |
| TTGTTATATT | AATTCTAGTT | AAAACAAGCG | ATATAATAAA | CGTACATAAG | AATAGAGTAG | 5727 |

| | | | | | | | | | | | |
|---|---|---|---|---|---|---|---|---|---|---|---|
| CGTACAAAAT | TGCTGACTTT | TTGCAATCTT | TA | ATG | GAG | AAT | ACC | CAC | TGT | GAG | 5780 |
| | | | | Met | Glu | Asn | Thr | His | Cys | Glu | |
| | | | | 1 | | | | 5 | | | |
| AAT | GGT | TTT | CTA | ACA | CTA | ATG | ATG | TTA | TAT | TCT | TTA | TTA | CAT | AAT | TTA | 5828 |
| Asn | Gly | Phe | Leu | Thr | Leu | Met | Met | Leu | Tyr | Ser | Leu | Leu | His | Asn | Leu | |
| | | 10 | | | | | 15 | | | | | 20 | | | | |
| CAA | GAT | CGT | TCC | CTT | GAG | TAT | TGT | ATC | CAC | TTT | TTC | ATA | CAT | TCA | TCG | 5876 |
| Gln | Asp | Arg | Ser | Leu | Glu | Tyr | Cys | Ile | His | Phe | Phe | Ile | His | Ser | Ser | |
| | | 25 | | | | 30 | | | | | 35 | | | | | |
| TGT | ACA | ACT | TTA | TAC | TCG | TTT | TTA | CAG | TTA | CAA | TAATTCTTTT | CAATACTGTA | 5929 |
| Cys | Thr | Thr | Leu | Tyr | Ser | Phe | Leu | Gln | Leu | Gln | | | |
| 40 | | | | | 45 | | | | | 50 | | | |

| | | | | | |
|---|---|---|---|---|---|
| GTCATCTTTA | CATATCCAAC | AAACAGGATC | CATTTTATAT | GGTACAAAAT | ATCTTCTAAG | 5989 |
| GTCTAGATTA | TACTTCAGTT | TTGATAAAAA | AATTATACAA | TTGAAACATC | TATATATCCT | 6049 |
| TTTAATACAT | CAACTCTAAT | AACTCTCACG | CTAATAGTTT | TTCCAACTAA | TGATTTCTTT | 6109 |
| AGATCTTCTA | TTTTATCGGC | TCTAATATTT | ATATAATTCA | ATATACACGC | TTCCATTGCA | 6169 |
| TAATCTGTTA | AATATGAGTA | AAATATGTTA | TTTCTAACAA | AAATTATACC | TTGCGTGATA | 6229 |

| | | |
|---|---|---|
| TCATTTATGT TAGGTAATCC ATAACAAAAT GCCAACGTAT TCATAGTTGA CATTATTGTT | 6289 |
| ATTTATTTGA ATACTTTATA TTTCATATTT CATACTTGTG TAGTATTTAA ACAACTCCAT | 6349 |
| AAATTATTTA ATATTATAGA TGCCTTGATA GGTGTGTATA TATCTGATAA TACACATGTT | 6409 |
| AGTTTGTCA TCTCCATTTC TGACGTAATA TTATATATAA TAAGATCGGT ACGTAACTTA | 6469 |
| TACATATGCT CATTTTTTC AGTACTATTG TATTCTTCT CTTTATAATG ATCGCTATTT | 6529 |
| AGTTGTTCTA CGAATGTATT GTTGTTACCT ACCATCCAAT ATAAGATACT ATACGTAGAA | 6589 |
| TTAGTATATC CGTTACATTT TACTATAACC TTATTTGTTT TCTTATGTGG TGGATATAAC | 6649 |
| AATACATCTC GTCCGTTACA TATATAAATC ATATATAATA CACACGATAA CACTATCCAC | 6709 |
| ATATTACGGT TCATTTTTAA AAAAAAAGAT TTATTTTTAT ATTTTTAATA CATACCGTAA | 6769 |

```
ACAGTAGTAA GTTACA ATG CTC GCT ATC ATC ATA CTT AAT CCA CGG CGC         6818
              Met Leu Ala Ile Ile Ile Leu Asn Pro Arg Arg
                1              5                       10

CTA CAT CGG GTA TCG GTA TAT TTA TCA AAT TCA TCT AAA AAT AAT ATA        6866
Leu His Arg Val Ser Val Tyr Leu Ser Asn Ser Ser Lys Asn Asn Ile
            15              20                      25

ATA TAT ATA CCG TCT TCT GAT ATA ATA TTT ATT ATA TCA TCA ATT ATA        6914
Ile Tyr Ile Pro Ser Ser Asp Ile Ile Phe Ile Ile Ser Ser Ile Ile
            30              35                      40

TAT TTA GCT ATA CGA ATA TTT CTA CAT ATT AGT TTA TCT ATT ATT ATA        6962
Tyr Leu Ala Ile Arg Ile Phe Leu His Ile Ser Leu Ser Ile Ile Ile
            45              50                      55

GAT AAT AAC GAA ATA GCA GCT AAT TTG ATA CTA GGT CGC GAA TCT GAT        7010
Asp Asn Asn Glu Ile Ala Ala Asn Leu Ile Leu Gly Arg Glu Ser Asp
60              65              70                      75

AAC AAT ATA CTA ATA ACT TCT TTA TGC ACG TTA TCT ATA TAC TTA TTT        7058
Asn Asn Ile Leu Ile Thr Ser Leu Cys Thr Leu Ser Ile Tyr Leu Phe
            80              85                      90

TCA TCG TAT TCT AAA ATA CAT GTA ACA GAA TTA AAA TCA TTA CAA TAT        7106
Ser Ser Tyr Ser Lys Ile His Val Thr Glu Leu Lys Ser Leu Gln Tyr
            95              100                     105

CTG TAT TTT ATC GCT TCA CAT TGATTTTTTA TCTTTGTGTA TATCATCCGT           7157
Leu Tyr Phe Ile Ala Ser His
110                 115
```

| | | |
|---|---|---|
| TCATATCTAC TAAGTTTATT TATAGTATTA TATTTAGAT ATACATATAA TACATTCCTA | 7217 |
| ATGCATACGT TAGAGTTATA TTTCTTGTAC ATATTGATAA TAATGGATAT AATACAGATG | 7277 |
| AATTATTTTT TCATTTATTA TACTTTACAT ACCACTTGAC CCAAAACCAC TATTTCCACG | 7337 |
| TTCTGTATCT TCCAAACATT TTACTTCTTC CATTATAGGA TATTCTACTC TTTCAAATAT | 7397 |
| TATTTGTGCT ATCCTATCAC CTACCTTTAT GTTAAAATCA CTACATCCAT TATTTATAAA | 7457 |
| CACGATACCT ATTTCCCCTC TGTAATCACT ATCAATAACG CCTCCTCCTA TATCTATATT | 7517 |
| ATAATTTAAC GATAATCCCG ATCTAGGCGA TATGCGTCCA TAACATTTAT CTGGTATCAT | 7577 |
| TAAACAAATA TCTGTTCTAA CTAAAATTCT ATTATACGGC TTAACTGTAT AACTATATGC | 7637 |
| ACTATACAGA TCATATCCAG CGGATCCGCT CATTGATCTA TTTGGTATAA TAGCATTATT | 7697 |
| AGATAACTTA ACACATTTAA CATATAGTGA CATGTCTAGA AAATATTATT TTTTTTTAA | 7757 |
| TTTTATAATA TTACTCACTA ACTAAAAAAG TTTTCTACGC ATTTTACTAC CCATAGCTTT | 7817 |
| AAGGATTTCC GTATCTCTAA ATCTATGTCT GCGTCTTTTT GAATTATCAC AATACGTATA | 7877 |
| TGATGATGTT GTAGGTGTTA TATTCTGTAT AGATCTTTGT AGTGTTCCAC TTATATATTC | 7937 |
| TGTATTATGT ATTCGTAATA TGACTTTATA GAGAAAATAA ATTGCTCTAT AATTATTATA | 7997 |
| TTTATTCATT ATTTTAATAG CTAGATCGAC TCTATCTAAT ACATTAATAT CATCGTTAGA | 8057 |

-continued

| | | | | | | |
|---|---|---|---|---|---|---|
| TATATTAATG | TCATCCTGTA | TCAAGAATAA | TAACGTTTTA | AACTGATACG | GTGTCAACCT | 8117 |
| TTCAAGCACA | GACAGATATG | ATCGTATAAC | GTAGTTCCAT | TGTCGTAACA | AGAAAAAATG | 8177 |
| TAGATTATTT | TTTCATTTCT | TGAAAGAATG | ACTCTATATC | GATAGACCCT | ACAATACCCC | 8237 |
| ATTCATCTAG | CTCCGTTATA | TATTTCTATT | TGACTAATAT | ATTTGTTAAT | AATATATCCA | 8297 |
| GCCTATTATA | GCGATAGAGT | CTTCTATAAT | ACAAAGCGAT | GAATTAAATC | GAGGAAAGGG | 8357 |
| TAGAGACTTT | TCTACAGTCC | ATTTATTCGA | ATGAGGGTTA | TACTTCTCAA | CCATAGTAAA | 8417 |
| TACATGAATA | TTATCTATAA | AAGATAAACC | ACCAATCATA | TATATATAAC | CATGGTGATA | 8477 |
| TGCTATACAT | CCACCAAAAT | GTGAATAATT | CATCGCATTA | CCAATAGACC | AAGTGTTTTC | 8537 |
| TTCATAAGAA | TAGATTTCAA | TAGTTTTATC | ATCTTCAGAA | ATACCACCAA | CAACATATAA | 8597 |
| ATCATTATCT | GTTCCAATTA | TGCAAGGATT | AAATCTGGGT | TGTAATAATG | GTACTTCTTC | 8657 |
| TCTCCATTGT | TGTTCTCCAG | GTGACCAACT | TTCTACTGTT | TTTAATGGTC | CATCGTATCC | 8717 |
| TATACCACCT | ACCACATAAA | TTCTATTTTT | AAAAATAGCA | ACACCCGGAC | ACTTTCTAGG | 8777 |
| ATGTAATAAT | GGTGGTGTAT | GCAACTCTAT | AAATGATCTA | GTGTCTACGC | TAGTTATATC | 8837 |
| ACTAACAGGA | TCCAATGATT | TATTTATACC | ACCTATAAGA | TATAATATAT | CATTCATAAG | 8897 |
| TACAGATCCA | CAGTAAGGAT | TATGATTCTC | AGCTATACTA | TTGATTATAC | TAAGTTCATT | 8957 |
| CTAACAGAT | ACATTACCTA | GCATATTTAT | ACTAATGAA | GATGGTGTAA | CCATCGTATA | 9017 |
| TCTTCTGTTT | GTAAATCTAT | GTTGATAACT | TATTCTAGGT | AATTCATTTT | CATTTAACTC | 9077 |
| TACATTATTA | TTTTTTCCGA | ATCGTGCCAA | CCATTTGTT | AATTTATACT | TACCATATAT | 9137 |
| GGATAGATAA | TTATATCTTA | GTACCTCTGT | TACTAGTGTA | AACGATTTTC | GTCTGTTGGA | 9197 |
| TTTTTTATGT | CTAGACCATT | TTATTATAAA | TAATAATACA | TCATCTTCTG | ATGATACATC | 9257 |
| TAATTCTCCA | CTTTTTAGAA | TTATTCTCAA | ATCAAATAAG | GATAACGATA | GTAATATATC | 9317 |
| TGTTTCTATT | TTTGTGAATC | TTTTCCTTAT | ATATGCTATA | GCATCATTAT | ATACCGCAAA | 9377 |
| ACATCCATTC | GAGAAACCTA | TTTTGTAAAT | CTTAACACAT | GTAGAATCCG | TTATATGTTT | 9437 |
| TGACATAAAA | TCAATACATG | AATTTTTTAA | AAAATCTATG | GCTTTACTAC | AAGATATGGA | 9497 |
| AAAAATATTT | TCTACATTGT | CTAAATCGAT | AGTAACGATT | CCAGTTTCTA | TATATTTAT | 9557 |
| TATATCAAGA | AAAGATTCAT | ACTGGAATGA | AACCGTTATT | TCATTACTCT | GATTCTTTGT | 9617 |
| AATAAGTTTA | AAGTAATTAG | ATACAGATAC | AAGTAATTCT | TTTTTACTT | TAACAACACC | 9677 |
| ACCAACGGTC | ATAATAAATA | CTATCTCTTC | ATCATAACTT | CTGTTAGAT | TCACAGCATT | 9737 |
| TAACCTTTCT | ATATAGTTAT | AATCAATGTA | AGTTCTTGT | TTAGACATTT | TTCACTATCT | 9797 |
| ATTTGCAAAC | CAAAGCAAAT | TACTATTATT | AAATTATTTA | TTCAACTTTA | TAAAAATTAT | 9857 |
| TAATTAAAAA | TCTATATCCG | TAGAAAATAT | ATTCTCTTCT | TTATTTGTAA | ACACCCCCAT | 9917 |
| CTTTTGATAT | TCACTAACTC | GTCGTTCGAA | AAAATTAGTC | TTACCTTCTA | GTGATATATA | 9977 |
| CTCCATAAAG | CTAAAGGAT | TATATACATT | GAGACTTTC | ACAACCTAAC | TCTGTTAATA | 10037 |
| ATCTATCTGC | GACGAATTCT | ATATACTGAG | ACATTAAACA | ACAATTCATA | CCTATAAGAT | 10097 |
| CCACCGGAAT | AGCAACTGTC | AAAAACTCCT | TTTCTATATT | AACCGCATCA | ATG ATT | 10153 |

```
                                                                Met Ile
                                                                 1
ATC GAC GTT ATA ACT TCC TTA GAT GGT GGA TGT AAT AAA TGT TTA AAC           10201
Ile Asp Val Ile Thr Ser Leu Asp Gly Gly Cys Asn Lys Cys Leu Asn
         5              10                  15

ATT AAA CAC GCA AAA TCA CAA TGT AAA CCT TCG TCT CTA CTT ATT AGT          10249
Ile Lys His Ala Lys Ser Gln Cys Lys Pro Ser Ser Leu Leu Ile Ser
```

|   |   |   |   |   |   |   |   |   |   |   |   |   |   |   |   |
|---|---|---|---|---|---|---|---|---|---|---|---|---|---|---|---|
|   |   | 20 |   |   |   | 25 |   |   |   | 30 |   |   |   |   |   |
| TCA | TTA | GAA | AAT | GTT | AAT | CCG | GGC | ATC | AAT | CCT | CGT | TTT | TTT | ATC | CAA | 10297 |
| Ser | Leu | Glu | Asn | Val | Asn | Pro | Gly | Ile | Asn | Pro | Arg | Phe | Phe | Ile | Gln |   |
|   | 35 |   |   |   | 40 |   |   |   | 45 |   |   |   |   |   | 50 |   |
| AAT | ATA | GCA | GCA | AAT | GAA | CCA | GAA | AAG | AAT | ATT | CCC | TCC | ACA | GCT | GCA | 10345 |
| Asn | Ile | Ala | Ala | Asn | Glu | Pro | Glu | Lys | Asn | Ile | Pro | Ser | Thr | Ala | Ala |   |
|   |   |   |   | 55 |   |   |   |   | 60 |   |   |   |   | 65 |   |   |
| AAT | GCT | ACT | ACT | CTT | TCT | CCA | TAT | ACC | TTG | TTG | CTA | GAT | ATC | CAT | TTT | 10393 |
| Asn | Ala | Thr | Thr | Leu | Ser | Pro | Tyr | Thr | Leu | Leu | Leu | Asp | Ile | His | Phe |   |
|   |   |   | 70 |   |   |   |   | 75 |   |   |   |   | 80 |   |   |   |
| CTG | GCC | CAA | TCA | GCT | TTC | TTT | TTT | ACG | CAT | TCC | ATT | GTT | TCT | ATA | GCG | 10441 |
| Leu | Ala | Gln | Ser | Ala | Phe | Phe | Phe | Thr | His | Ser | Ile | Val | Ser | Ile | Ala |   |
|   |   | 85 |   |   |   |   | 90 |   |   |   |   | 95 |   |   |   |   |
| TTA | AAT | AAA | TGC | ATT | TTT | TCT | ATA | TTA | TCT | CTT | ACA | TAT | GTA | TCT | ATT | 10489 |
| Leu | Asn | Lys | Cys | Ile | Phe | Ser | Ile | Leu | Ser | Leu | Thr | Tyr | Val | Ser | Ile |   |
|   | 100 |   |   |   |   | 105 |   |   |   |   | 110 |   |   |   |   |   |
| AAT | AAA | CTA | TAC | ATT | TCT | GAA | TGAATATTTT | CCATAGCTAT | TTGAAATCCA |   |   |   |   |   |   | 10540 |
| Asn | Lys | Leu | Tyr | Ile | Ser | Glu |   |   |   |   |   |   |   |   |   |   |
| 115 |   |   |   |   | 120 |   |   |   |   |   |   |   |   |   |   |   |

| | | | | |
|---|---|---|---|---|
| TAGAAACATC | GTGCCTCTGA | ACACTGTACA | TCCACATAAA | ATCTTTCCGC | TAAATTCTCA | 10600 |
| TTTACAATAC | CATCACTAGA | TGCAAAAAAT | GCTAGTATAT | GTTTATAAA | GTATTTTCG | 10660 |
| TCTTTAGTTA | ATTTATCCCA | ATCATCTAAA | TCTTTTGATA | AATCTACTTC | TTCAACGGTC | 10720 |
| CAAAAACTTG | CCACTGATTG | TTTATACATT | TTCCAGATAT | CATGATACTT | AATAGGGAAA | 10780 |
| ATAACGAACC | TAGAATCAGA | CTCTTGAAGA | ATAGGCTCCA | TTCGTGTATA | AAAATCATTT | 10840 |
| TTCAATTTAT | TCGGTATTAA | CACCAACGCT | GCTATCGTTC | GTATAATACA | TATTATCTAA | 10900 |
| TTGTAAAAAT | TCTCTTCTCG | ATGTCCATTG | TAAACATCTA | GTTCTTATTT | GTCTAAATAT | 10960 |
| ATCTACTATA | AACGACCATC | TTACTAATTG | TAGTAGTAAA | TAACACGTTA | TCACGATAGT | 11020 |
| AACTAAACAT | AATGTAATTA | CCATTATTGT | TCCAACTTCA | TTAGACATAT | CATTATCTAT | 11080 |
| AATTATTTGT | GAAGTTGTTG | TATTCATTGT | CTGAATGTTT | AATTATTATT | TTTTTGTTT | 11140 |
| TTTTTACTAA | ATAAAAACAT | CATCATCGCT | ACTACTACAA | CGTTCCTTA | TAACTTTTAC | 11200 |
| TTTATAAGGT | ATTTTGATGT | TATTTTTATG | TATCAACTTT | TCATTCTCCT | GGTAATAGTC | 11260 |
| GGTATTAGAT | TTTATCCTAT | AAGTTGATTT | CTTTCTTAAA | AATGTAGTAA | ATTTCTTTCG | 11320 |
| TAAATATGAC | ATAAAACCAT | TATTTATTGA | ATACTTACGA | TTATTCATTA | TTATTTATTT | 11380 |
| AGAAATATAC | TGATTTAATA | CTATATGTGG | AATATCTCGA | TTCTAGACTA | TATGTAGAAT | 11440 |
| ATCTCGATTC | TAGTGTACTA | CTACAACTAT | TTTTCTTCT | TACATATATT | GGCTTATTTT | 11500 |
| TTATATTATA | ATAATATTCA | TCGTCTATAG | AAGATATTGA | CACTGTATCC | ATACTTATAC | 11560 |
| TTATTGATTT | TACAGATACA | CAACTGCCCA | TAGTTCGTAT | ATATTGGCTT | TGTATGTTGC | 11620 |
| AATATTTTT | CAATATAAAA | AAAATAACAA | AAAGACGAGT | ATAATAAAAT | ACATAAAGTA | 11680 |
| AAAACAAACA | TATTATTATT | TACTTCATTT | TTAAGGTGCA | TGCATTTTCC | TTTTGAAATG | 11740 |
| AAATGAAATG | AAATGAAATG | TAGTGCTCTA | AAACAAACTT | AACCTTACTT | ATAAATATCC | 11800 |
| TCCATATTTA | CCCATTATAA | TAGAATTGTG | TGGACCTAGT | AGTTATAATC | ATAGGATAAT | 11860 |
| CATTATGTAA | ATACGATTCT | CTTTTATAT | GTTGATTAGG | TTTAATATTT | AGACAATATC | 11920 |
| CATATTTATT | TATTTCATCA | TTAGTGGGTG | GTGTAGACTG | TGTATGTTGT | ACAGACTTGC | 11980 |
| CGGTTAAAAC | AATTTTATTT | ACTTTTTTCG | GTTTCCGCTC | ATGGTTATTT | AGTAGGCGAT | 12040 |
| TATTTATGTT | ATTAGCTATG | ATTTATGTTT | CATTTTTAAC | CCGGTTTAGA | CATATAAAAA | 12100 |
| TGTACCATAT | TTGTATTTAA | TTCCTATTCG | TCTTTTTATA | GAACATATTC | CTATAACAAA | 12160 |

-continued

```
TATGATAGCA ATAATAATGA TGCTAAATAT AAACCATGGT CTATTTGTTA AATTCAAATA      12220

ATTATATATA TTAGCATTGT CAATATATCT TCTATTCATA GAATTCATGA TAGAATTCAT      12280

CACACAGTTT GCTTCTGCAG TACCAGAATT AACAATCTGT AATAGAATCT GTTATCGTA       12340

CGGAGCTATG CATTTTCCAA CATCTAATGT TTGAATATCA ATAATATTTG TTACATCTGC      12400

GGATGATGAA CAGTTCGTA TTATTCTGG TACATATTA GGGTCATTGT TTAATATATC         12460

AATTCCAATT TCTTTAGATA ATTCCTCTTT CTCTTTCTGA GATAACGTAC TAGTTACATC      12520

TTTAAGCGTC TTTATAAGAA TATTGAAACT TAGTTCTTTA TCGTTTATAC ACATATTGAG      12580

TATTTTCAAA AAACATCTTT TGAACGTTCC TTTGATTTCT CCTATATGTA TACCACATGT      12640

TGAATTAATA GGTATAGAAT ATATTGATAA GTTCTCTATA TATCTTTCTA CGAATACGTT      12700

ATATAATGTA TTTATTCTAA CAGGATTCTC CATTTATCCA ATTGAGAAA ATGTTTTTG        12760

TAATCAAATT TTCTAAAAAT GATATAGGAT GCAGTATGGA TACTTTTAAT CTAAATTTCT     12820

CACATGTATT TTTTGTACAA CACATTATAA AATCCTCTAA AGAATCGCTG AATTCTTTAT      12880

CAGATTCTAT TTCTGGATAA GTTCGTAGAA GTGTATGTAT AAAAAAATGA AAATCATAAT     12940

ACCAATTGTG TTCTATTTTT AAACTATTTT TAATTTCTT ATTTAATATA TTAGCCACCT      13000

GTGAAAAATC GAAATCGTTA AGACACGCTT TAATCGGTTC ATTAAATACG TATGTATATT     13060

TCTTAAATTT AATAGTTATA GGACAATCAG AATTAAATAT TAAAATATTA TCGGGTTTTA    13120

AATCAACGTG TAAAAAATTA TCACAACAAG GAAGTTCGTA TATTTTATA TATAACAATG      13180

ATATTTGTAA AAAAATAAAC TTAACATATT GAACTATAGA TTTAAAACCA AGTTCTATCG     13240

CCATCTGTTC CGTCACTTTA TCTGATGAAA ATCTTGCTAA TGGGAATATA ATTATATTTC    13300

CTCTATCGTA TAAATAATTA GCTCTTTTTT CATGTTCGAA AAAATGAAAC ATATGTGTAA     13360

AATAATTTAT TACATTTATA TTACTTTGAA CAACAATAGG ATAAAAATAT GATAATAATT    13420

TTACAAATTT TATATCGCTC TTTTTTTCAT TGAACGACTT AAGAAAATAC TTATGAGAAA    13480

AATGATGAAT ATTTAATCGT TGATTATCTA TCGTTTGAAT AATAAGTAAT AACATATATA    13540

ATACTCTTTT ATATAATCTA TGTAGAAATG TTAATTTATA ATTTAAACCC ATTGCCCATG     13600

CACAAACGAT AAGTTTTTC TCATCTCCCT TAAGATTATT ATATAAAAAT TTAGGTATTG      13660

TATACTCGGC AGTTGTATCA ATGGGACTAT ACTGTTTATT TGGTTCATAA ACAAATTTAA    13720

CAACGTATTT ATCCATTTTA AATACGATAC CATAACCTCC TGTTGATATA TGATAGAAAT    13780

CATCATTAAG TGGATAAAAT CGTTTATCTC TTTGTTGGAA AAAAGATGGG TTAATATATT    13840

CCGTATCTGA TATTTTATCA AATGATTCTT TGTTAAACTT CCTAAAATAT CTTATTAGTC     13900

TGATATCAGG AGACCAATTT TGATGTATAT CTAACTGAGA AATTATATAA TCAAAATATA    13960

TATCATCACC GAGAATAGTT GTATCATTAT TATCATCGAT AGACTCCCAC TGACATTCTA    14020

ACGAATTAAT TTCTTTCATT TATTGTATAA AAAGCTACTT TATTGTATAC GAAATCCAAT    14080

ATTTGATAAT GCGAATAAAT TATTAACTAT TTCTTCTTTT AAAGAATAAG ATTCTCCCAT     14140

TGATAGTTTG TATATTACAT ATGAATCAAT AAGCTT                               14176
```

( 2 ) INFORMATION FOR SEQ ID NO:2:

( i ) SEQUENCE CHARACTERISTICS:
( A ) LENGTH: 124 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met  Asn  Ser  Cys  Tyr  Asp  Arg  Phe  Arg  Ile  Ile  Phe  Gln  Lys  Lys  Asn
 1              5                        10                         15

Asn  Tyr  Tyr  Cys  Lys  Tyr  Asn  Asp  Cys  Met  Arg  Tyr  Phe  Leu  Asn  Ile
               20                        25                        30

Ser  Leu  Tyr  Leu  Ile  Leu  Ile  Cys  Glu  Lys  Asn  Ile  Thr  Ser  Lys  Ser
           35                       40                        45

Thr  Ser  Ile  Ile  Phe  Asp  Asp  Asn  Ile  Ala  Asn  Ile  Pro  Ile  Glu  Asp
     50                        55                        60

Leu  Gln  Cys  Leu  Ile  Ile  Ser  Ser  Leu  His  Phe  Lys  Arg  Met  Leu  Met
 65                       70                   75                         80

Asp  Ile  Val  Ser  Pro  Ser  Leu  Tyr  Val  Phe  Ile  Ile  Ser  Leu  Tyr  Ile
                     85                   90                         95

Tyr  Phe  Val  Ala  Asn  Ile  Ser  Tyr  Phe  Met  Ser  Ser  Leu  Asn  Asn  Leu
                100                      105                      110

Pro  His  Ala  His  Val  Leu  Leu  Tyr  Phe  Phe  Leu  Gln
               115                 120
```

(2) INFORMATION FOR SEQ ID NO:3:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:3:

```
Met  Asn  Phe  Leu  Leu  Gln  Tyr  Thr  Asn  Ser  Phe  Leu  Tyr  Leu  Tyr  Lys
 1              5                        10                        15

Arg  Ile  Tyr  Cys  Ser  Val  Phe  Thr  Ile  Ser  Ser  Cys  Asn  Ile  Ser  Leu
               20                        25                        30

Asn  Glu  Asp  Asn  Ile  Leu  Leu  Tyr  Lys  Cys  Ile  Asn  Phe  Asp  Asp  Ile
           35                       40                        45

Leu  Asp  Ser  Tyr  Leu  Ser  Leu  Thr  Thr  Leu  Tyr  Asn  Leu  Leu  Leu  Thr
     50                        55                        60

Leu  Ser  Ile  Ser  Ser  Lys  Ser  Leu  Ile  Lys  Tyr  Val  Ser  Ile  Phe  Leu
 65                       70                   75                         80

Gly  Ile  Asn  Pro  Ser  Thr  His  Thr  Leu  Val  Leu  Leu  Ser  Val  Phe  Phe
                     85                   90                         95

Gly  Pro  Asn  Ser
                100
```

(2) INFORMATION FOR SEQ ID NO:4:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Leu  Thr  Ile  Gly  Glu  Val  Ile  Cys  Thr  Ile  Ser  His  Thr  Leu  Pro
 1              5                        10                        15

Ile  Leu  Cys  Ser  Leu  Asp  Val  Leu  Phe  Ser  Tyr  Leu  Asn  Leu  Thr  His
               20                        25                        30

Val  Ser  Ser  Ser  Leu  Ser  Ile  Ser  Glu  Phe  Val  Lys  Leu  Gln  Tyr  Pro
           35                       40                        45

Lys  Glu  Leu  Val  Gln  Thr  Val  Leu  His  Ser  Ser
     50                        55
```

( 2 ) INFORMATION FOR SEQ ID NO:5:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Glu Asn Thr His Cys Glu Asn Gly Phe Leu Thr Leu Met Met Leu
 1               5                  10                  15
Tyr Ser Leu Leu His Asn Leu Gln Asp Arg Ser Leu Glu Tyr Cys Ile
                20                  25                  30
His Phe Phe Ile His Ser Ser Cys Thr Thr Leu Tyr Ser Phe Leu Gln
                35                  40                  45
Leu Gln
 50
```

( 2 ) INFORMATION FOR SEQ ID NO:6:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Leu Ala Ile Ile Ile Leu Asn Pro Arg Arg Leu His Arg Val Ser
 1               5                  10                  15
Val Tyr Leu Ser Asn Ser Ser Lys Asn Asn Ile Ile Tyr Ile Pro Ser
                20                  25                  30
Ser Asp Ile Ile Phe Ile Ile Ser Ser Ile Ile Tyr Leu Ala Ile Arg
                35                  40                  45
Ile Phe Leu His Ile Ser Leu Ser Ile Ile Ile Asp Asn Asn Glu Ile
         50                  55                  60
Ala Ala Asn Leu Ile Leu Gly Arg Glu Ser Asp Asn Asn Ile Leu Ile
 65                  70                  75                  80
Thr Ser Leu Cys Thr Leu Ser Ile Tyr Leu Phe Ser Ser Tyr Ser Lys
                85                  90                  95
Ile His Val Thr Glu Leu Lys Ser Leu Gln Tyr Leu Tyr Phe Ile Ala
               100                 105                 110
Ser His
```

( 2 ) INFORMATION FOR SEQ ID NO:7:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Ile Ile Asp Val Ile Thr Ser Leu Asp Gly Gly Cys Asn Lys Cys
 1               5                  10                  15
Leu Asn Ile Lys His Ala Lys Ser Gln Cys Lys Pro Ser Ser Leu Leu
                20                  25                  30
Ile Ser Ser Leu Glu Asn Val Asn Pro Gly Ile Asn Pro Arg Phe Phe
                35                  40                  45
```

| Ile | Gln | Asn | Ile | Ala | Ala | Asn | Glu | Pro | Glu | Lys | Asn | Ile | Pro | Ser | Thr |
|     | 50  |     |     |     |     | 55  |     |     |     |     | 60  |     |     |     |     |

| Ala | Ala | Asn | Ala | Thr | Thr | Leu | Ser | Pro | Tyr | Thr | Leu | Leu | Leu | Asp | Ile |
| 65  |     |     |     |     | 70  |     |     |     |     | 75  |     |     |     |     | 80  |

| His | Phe | Leu | Ala | Gln | Ser | Ala | Phe | Phe | Phe | Thr | His | Ser | Ile | Val | Ser |
|     |     |     |     |     | 85  |     |     |     |     | 90  |     |     |     |     | 95  |

| Ile | Ala | Leu | Asn | Lys | Cys | Ile | Phe | Ser | Ile | Leu | Ser | Leu | Thr | Tyr | Val |
|     |     |     |     | 100 |     |     |     |     | 105 |     |     |     |     | 110 |     |

| Ser | Ile | Asn | Lys | Leu | Tyr | Ile | Ser | Glu |
|     |     |     |     | 115 |     |     |     | 120 |

( 2 ) INFORMATION FOR SEQ ID NO:8:

( i ) SEQUENCE CHARACTERISTICS:
        ( A ) LENGTH: 375 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:8:

```
ATGAATTCAT GTTATGATAG ATTTAGGATT ATTTTTCAAA AAAAAAACAA TTATTATTGT      60
AAGTATAATG ATTGTATGAG ATATTTTTTG AATATTAGTC TATATCTTAT ACTTATTTGT     120
GAAAAGAATA TAACATCAAA ATCTACGTCG ATTATTTTCG ATGATAATAT AGCAAACATA     180
CCTATAGAAG ACTTACAATG TTTAATTATA TCATCTTTAC ATTTAAACG TATGTTAATG      240
GATATAGTAT CTCCCTCTTT GTATGTATTT ATAATATCAT TATATATATA TTTTGTAGCT     300
AATATATCAT ATTCATGAG  TTCCTTAAAT AACTTACCAC ATGCGCATGT GTTGTTATAT     360
TTTTTTCTCC AATGA                                                     375
```

( 2 ) INFORMATION FOR SEQ ID NO:9:

( i ) SEQUENCE CHARACTERISTICS:
        ( A ) LENGTH: 303 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:9:

```
ATGAATTTTT TATTACAATA TACGAATTCA TTCCTTTATC TTTATAAACG TATTTACTGT      60
TCAGTATTTA CCATAAGTTC TTGCAATATT AGTTTAAACG AAGATAATAT ATTATTATAT     120
AAGTGCATAA ACTTTGACGA TATATTGGAT TCATATTTAT CACTTACAAC TCTATATAAT     180
CTGTTATTAA CTCTATCTAT ATCATCGAAA TCTTTAATAA AATATGTATC GATTTTCTT      240
GGAATTAATC CATCTACACA CACTCTAGTA CTATTATCTG TTTTTTTTGG ACCAAATTCA     300
TAA                                                                  303
```

( 2 ) INFORMATION FOR SEQ ID NO:10:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:10:

```
ATGTTAACAA   TAGGTGAAGT   TATTTGTACA   ATCTCACATA   CTCTGCCAAT   ATTATGTTCA      60

TTAGATGTCT   TATTTTCATA   TTTAAACCTC   ACCCATGTTT   CATCATCATT   GTCGATATCA     120

GAATTGTTA    AATTACAGTA   TCCTAAAGAA   TTAGTACAAA   CGGTTCTCCA   TTCGTCATGA     180
```

( 2 ) INFORMATION FOR SEQ ID NO:11:

( i ) SEQUENCE CHARACTERISTICS:
        ( A ) LENGTH: 153 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:11:

```
ATGGAGAATA   CCCACTGTGA   GAATGGTTTT   CTAACACTAA   TGATGTTATA   TTCTTTATTA      60

CATAATTTAC   AAGATCGTTC   CCTTGAGTAT   TGTATCCACT   TTTTCATACA   TTCATCGTGT     120

ACAACTTTAT   ACTCGTTTTT   ACAGTTACAA   TAA                                     153
```

( 2 ) INFORMATION FOR SEQ ID NO:12:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:12:

```
ATGCTCGCTA   TCATCATACT   TAATCCACGG   CGCCTACATC   GGGTATCGGT   ATATTTATCA      60

AATTCATCTA   AAAATAATAT   AATATATATA   CCGTCTTCTG   ATATAATATT   TATTATATCA     120

TCAATTATAT   ATTTAGCTAT   ACGAATATTT   CTACATATTA   GTTTATCTAT   TATTATAGAT     180

AATAACGAAA   TAGCAGCTAA   TTTGATACTA   GGTCGCGAAT   CTGATAACAA   TATACTAATA     240

ACTTCTTTAT   GCACGTTATC   TATATACTTA   TTTTCATCGT   ATTCTAAAAT   ACATGTAACA     300

GAATTAAAAT   CATTACAATA   TCTGTATTTT   ATCGCTTCAC   ATTGA                      345
```

( 2 ) INFORMATION FOR SEQ ID NO:13:

( i ) SEQUENCE CHARACTERISTICS:
        ( A ) LENGTH: 366 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:13:

```
ATGATTATCG   ACGTTATAAC   TTCCTTAGAT   GGTGGATGTA   ATAAATGTTT   AAACATTAAA      60

CACGCAAAAT   CACAATGTAA   ACCTTCGTCT   CTACTTATTA   GTTCATTAGA   AAATGTTAAT     120

CCGGGCATCA   ATCCTCGTTT   TTTTATCCAA   AATATAGCAG   CAAATGAACC   AGAAAAGAAT     180

ATTCCCTCCA   CAGCTGCAAA   TGCTACTACT   CTTCTCCAT    ATACCTTGTT   GCTAGATATC     240

CATTTCTGG    CCCAATCAGC   TTTCTTTTTT   ACGCATTCCA   TTGTTTCTAT   AGCGTTAAAT     300

AAATGCATTT   TTTCTATATT   ATCTCTTACA   TATGTATCTA   TTAATAAACT   ATACATTTCT     360

GAATGA                                                                         366
```

( 2 ) INFORMATION FOR SEQ ID NO:14:

(i) SEQUENCE CHARACTERISTICS:
 (A) LENGTH: 14176 base pairs
 (B) TYPE: nucleic acid
 (C) STRANDEDNESS: double
 (D) TOPOLOGY: unknown (ii) MOLECULE TYPE: DNA (genomic)

(ix) FEATURE:
 (A) NAME/KEY: CDS
 (B) LOCATION: 138..1460

(ix) FEATURE:
 (A) NAME/KEY: CDS
 (B) LOCATION: 2456..2659

(ix) FEATURE:
 (A) NAME/KEY: CDS
 (B) LOCATION: 2809..3030

(ix) FEATURE:
 (A) NAME/KEY: CDS
 (B) LOCATION: 3070..3330

(ix) FEATURE:
 (A) NAME/KEY: CDS
 (B) LOCATION: 3356..4180

(ix) FEATURE:
 (A) NAME/KEY: CDS
 (B) LOCATION: 4392..5894

(ix) FEATURE:
 (A) NAME/KEY: CDS
 (B) LOCATION: 6171..6398

(ix) FEATURE:
 (A) NAME/KEY: CDS
 (B) LOCATION: 6447..6875

(ix) FEATURE:
 (A) NAME/KEY: CDS
 (B) LOCATION: 6928..7431

(ix) FEATURE:
 (A) NAME/KEY: CDS
 (B) LOCATION: 7454..7858

(ix) FEATURE:
 (A) NAME/KEY: CDS
 (B) LOCATION: 7895..8155

(ix) FEATURE:
 (A) NAME/KEY: CDS
 (B) LOCATION: 8215..8682

(ix) FEATURE:
 (A) NAME/KEY: CDS
 (B) LOCATION: 8715..9539

(ix) FEATURE:
 (A) NAME/KEY: CDS
 (B) LOCATION: 9562..10272

(ix) FEATURE:
 (A) NAME/KEY: CDS
 (B) LOCATION: 10316..11908

(ix) FEATURE:
 (A) NAME/KEY: CDS
 (B) LOCATION: 11971..12780

(ix) FEATURE:
 (A) NAME/KEY: CDS
 (B) LOCATION: 12829..13107

(ix) FEATURE:
 (A) NAME/KEY: CDS
 (B) LOCATION: 13149..14171

( x i ) SEQUENCE DESCRIPTION: SEQ ID NO:14:

| | | | | | | | | | | | | |
|---|---|---|---|---|---|---|---|---|---|---|---|---|
| AAGCTTATTG | ATTCATATGT | AATATACAAA | CTATCAATGG | GAGAATCTTA | TTCTTTAAAA | | | | | | | 60 |
| GAAGAAATAG | TTAATAATTT | ATTCGCATTA | TCAAATATTG | GATTCGTAT | ACAATAAAGT | | | | | | | 120 |
| AGCTTTTTAT | ACAATAA | ATG | AAA | GAA | ATT | AAT | TCG | TTA | GAA | TGT | CAG | TGG | 170 |
| | | Met | Lys | Glu | Ile | Asn | Ser | Leu | Glu | Cys | Gln | Trp | |
| | | 1 | | 5 | | | | | | 10 | | | |

```
GAG TCT ATC GAT GAT AAT AAT GAT ACA ACT ATT CTC GGT GAT GAT ATA          218
Glu Ser Ile Asp Asp Asn Asn Asp Thr Thr Ile Leu Gly Asp Asp Ile
             15                  20                  25

TAT TTT GAT TAT ATA ATT TCT CAG TTA GAT ATA CAT CAA AAT TGG TCT          266
Tyr Phe Asp Tyr Ile Ile Ser Gln Leu Asp Ile His Gln Asn Trp Ser
             30                  35                  40

CCT GAT ATC AGA CTA ATA AGA TAT TTT AGG AAG TTT AAC AAA GAA TCA          314
Pro Asp Ile Arg Leu Ile Arg Tyr Phe Arg Lys Phe Asn Lys Glu Ser
             45                  50                  55

TTT GAT AAA ATA TCA GAT ACG GAA TAT ATT AAC CCA TCT TTT TTC CAA          362
Phe Asp Lys Ile Ser Asp Thr Glu Tyr Ile Asn Pro Ser Phe Phe Gln
60                  65                  70                  75

CAA AGA GAT AAA CGA TTT TAT CCA CTT AAT GAT GAT TTC TAT CAT ATA          410
Gln Arg Asp Lys Arg Phe Tyr Pro Leu Asn Asp Asp Phe Tyr His Ile
                 80                  85                  90

TCA ACA GGA GGT TAT GGT ATC GTA TTT AAA ATG GAT AAA TAC GTT GTT          458
Ser Thr Gly Gly Tyr Gly Ile Val Phe Lys Met Asp Lys Tyr Val Val
             95                 100                 105

AAA TTT GTT TAT GAA CCA AAT AAA CAG TAT AGT CCC ATT GAT ACA ACT          506
Lys Phe Val Tyr Glu Pro Asn Lys Gln Tyr Ser Pro Ile Asp Thr Thr
            110                 115                 120

GCC GAG TAT ACA ATA CCT AAA TTT TTA TAT AAT AAT CTT AAG GGA GAT          554
Ala Glu Tyr Thr Ile Pro Lys Phe Leu Tyr Asn Asn Leu Lys Gly Asp
125                 130                 135

GAG AAA AAA CTT ATC GTT TGT GCA TGG GCA ATG GGT TTA AAT TAT AAA          602
Glu Lys Lys Leu Ile Val Cys Ala Trp Ala Met Gly Leu Asn Tyr Lys
140                 145                 150                 155

TTA ACA TTT CTA CAT AGA TTA TAT AAA AGA GTA TTA TAT ATG TTA TTA          650
Leu Thr Phe Leu His Arg Leu Tyr Lys Arg Val Leu Tyr Met Leu Leu
                160                 165                 170

CTT ATT ATT CAA ACG ATA GAT AAT CAA CGA TTA AAT ATT CAT CAT TTT          698
Leu Ile Ile Gln Thr Ile Asp Asn Gln Arg Leu Asn Ile His His Phe
            175                 180                 185

TCT CAT AAG TAT TTT CTT AAG TCG TTC AAT GAA AAA AAG AGC GAT ATA          746
Ser His Lys Tyr Phe Leu Lys Ser Phe Asn Glu Lys Lys Ser Asp Ile
        190                 195                 200

AAA TTT GTA AAA TTA TTA TCA TAT TTT TAT CCT ATT GTT GTT CAA AGT          794
Lys Phe Val Lys Leu Leu Ser Tyr Phe Tyr Pro Ile Val Val Gln Ser
205                 210                 215

AAT ATA AAT GTA ATA AAT TAT TTT ACA CAT ATG TTT CAT TTT TTC GAA          842
Asn Ile Asn Val Ile Asn Tyr Phe Thr His Met Phe His Phe Phe Glu
220                 225                 230                 235

CAT GAA AAA AGA GCT AAT TAT TTA TAC GAT AGA GGA AAT ATA ATT ATA          890
His Glu Lys Arg Ala Asn Tyr Leu Tyr Asp Arg Gly Asn Ile Ile Ile
                240                 245                 250

TTC CCA TTA GCA AGA TTT TCA TCA GAT AAA GTG ACG GAA CAG ATG GCG          938
Phe Pro Leu Ala Arg Phe Ser Ser Asp Lys Val Thr Glu Gln Met Ala
            255                 260                 265

ATA GAA CTT GGT TTT AAA TCT ATA GTT CAA TAT GTT AAG TTT ATT TTT          986
Ile Glu Leu Gly Phe Lys Ser Ile Val Gln Tyr Val Lys Phe Ile Phe
        270                 275                 280
```

| | | | | | | | | | | | | | | | | |
|---|---|---|---|---|---|---|---|---|---|---|---|---|---|---|---|---|
| TTA | CAA | ATA | TCA | TTG | TTA | TAT | ATA | AAA | ATA | TAC | GAA | CTT | CCT | TGT | TGT | 1034 |
| Leu | Gln | Ile | Ser | Leu | Leu | Tyr | Ile | Lys | Ile | Tyr | Glu | Leu | Pro | Cys | Cys | |
| | 285 | | | | 290 | | | | | 295 | | | | | | |
| GAT | AAT | TTT | TTA | CAC | GTT | GAT | TTA | AAA | CCC | GAT | AAT | ATT | TTA | ATA | TTT | 1082 |
| Asp | Asn | Phe | Leu | His | Val | Asp | Leu | Lys | Pro | Asp | Asn | Ile | Leu | Ile | Phe | |
| 300 | | | | | 305 | | | | | 310 | | | | | 315 | |
| AAT | TCT | GAT | TGT | CCT | ATA | ACT | ATT | AAA | TTT | AAG | AAA | TAT | ACA | TAC | GTA | 1130 |
| Asn | Ser | Asp | Cys | Pro | Ile | Thr | Ile | Lys | Phe | Lys | Lys | Tyr | Thr | Tyr | Val | |
| | | | | 320 | | | | | 325 | | | | | 330 | | |
| TTT | AAT | GAA | CCG | ATT | AAA | GCG | TGT | CTT | AAC | GAT | TTC | GAT | TTT | TCA | CAG | 1178 |
| Phe | Asn | Glu | Pro | Ile | Lys | Ala | Cys | Leu | Asn | Asp | Phe | Asp | Phe | Ser | Gln | |
| | | | 335 | | | | | 340 | | | | | 345 | | | |
| GTG | GCT | AAT | ATA | TTA | AAT | AAG | AAA | ATT | AAA | AAT | AGT | TTA | AAA | ATA | GAA | 1226 |
| Val | Ala | Asn | Ile | Leu | Asn | Lys | Lys | Ile | Lys | Asn | Ser | Leu | Lys | Ile | Glu | |
| | | 350 | | | | | 355 | | | | | 360 | | | | |
| CAC | AAT | TGG | TAT | TAT | GAT | TTT | CAT | TTT | TTT | ATA | CAT | ACA | CTT | CTA | CGA | 1274 |
| His | Asn | Trp | Tyr | Tyr | Asp | Phe | His | Phe | Phe | Ile | His | Thr | Leu | Leu | Arg | |
| | 365 | | | | 370 | | | | | 375 | | | | | | |
| ACT | TAT | CCA | GAA | ATA | GAA | TCT | GAT | AAA | GAA | TTC | AGC | GAT | TCT | TTA | GAG | 1322 |
| Thr | Tyr | Pro | Glu | Ile | Glu | Ser | Asp | Lys | Glu | Phe | Ser | Asp | Ser | Leu | Glu | |
| 380 | | | | | 385 | | | | | 390 | | | | | 395 | |
| GAT | TTT | ATA | ATG | TGT | TGT | ACA | AAA | AAT | ACA | TGT | GAG | AAA | TTT | AGA | TTA | 1370 |
| Asp | Phe | Ile | Met | Cys | Cys | Thr | Lys | Asn | Thr | Cys | Glu | Lys | Phe | Arg | Leu | |
| | | | | 400 | | | | | 405 | | | | | 410 | | |
| AAA | GTA | TCC | ATA | CTG | CAT | CCT | ATA | TCA | TTT | TTA | GAA | AAT | TTG | ATT | ACA | 1418 |
| Lys | Val | Ser | Ile | Leu | His | Pro | Ile | Ser | Phe | Leu | Glu | Asn | Leu | Ile | Thr | |
| | | | 415 | | | | | 420 | | | | | 425 | | | |
| AAA | AAC | ATT | TTC | TCA | AAT | TGG | ATA | AAT | GGA | GAA | TCC | TGT | TAGAATAAAT | | | 1467 |
| Lys | Asn | Ile | Phe | Ser | Asn | Trp | Ile | Asn | Gly | Glu | Ser | Cys | | | | |
| | | 430 | | | | | 435 | | | | | 440 | | | | |

| | |
|---|---|
| ACATTATATA ACGTATTCGT AGAAAGATAT ATAGAGAACT TATCAATATA TTCTATACCT | 1527 |
| ATTAATTCAA CATGTGGTAT ACATATAGGA GAAATCAAAG GAACGTTCAA AAGATGTTTT | 1587 |
| TTGAAAATAC TCAATATGTG TATAAACGAT AAAGAACTAA GTTCAATAT TCTTATAAAG | 1647 |
| ACGCTTAAAG ATGTAACTAG TACGTTATCT CAGAAAGAGA AAGAGGAATT ATCTAAAGAA | 1707 |
| ATTGGAATTG ATATATTAAA CAATGACCCT AAATATGTAC CAGAAATAAT ACGAAACTGT | 1767 |
| TCATCATCCG CAGATGTAAC AAATATTATT GATATTCAAA CATTAGATGT TGGAAAATGC | 1827 |
| ATAGCTCCGT ACGATAAACA GATTCTATTA CAGATTGTTA ATTCTGGTAC TGCAGAAGCA | 1887 |
| AACTGTGTGA TGAATTCTAT CATGAATTCT ATGAATAGAA GATATATTGA CAATGCTAAT | 1947 |
| ATATATAATT ATTTGAATTT AACAAATAGA CCATGGTTTA TATTTAGCAT CATTATTATT | 2007 |
| GCTATCATAT TTGTTATAGG AATATGTTCT ATAAAAGAC GAATAGGAAT TAAATACAAA | 2067 |
| TATGGTACAT TTTTATATGT CTAAACCGGG TTAAAAATGA ACATAAATC ATAGCTAATA | 2127 |
| ACATAAATAA TCGCCTACTA ATAACCATG AGCGGAAACC GAAAAAGTA AATAAAATTG | 2187 |
| TTTTAACCGG CAAGTCTGTA CAACATACAC AGTCTACACC ACCCACTAAT GATGAAATAA | 2247 |
| ATAAATATGG ATATTGTCTA AATATTAAAC CTAATCAACA TATAAAAAGA GAATCGTATT | 2307 |
| TACATAATGA TTATCCTATG ATTATAACTA CTAGGTCCAC ACAATTCTAT TATAATGGGT | 2367 |
| AAATATGGAG GATATTTATA AGTAAGGTTA AGTTTGTTTT AGAGCACTAC ATTTCATTTC | 2427 |
| ATTTCATTTC ATTTCAAAAG GAAAATGC ATG CAC CTT AAA AAT GAA GTA AAT | 2479 |
| Met His Leu Lys Asn Glu Val Asn | |
| 1 5 | |

| | | | | | | | | | | | | | | | | |
|---|---|---|---|---|---|---|---|---|---|---|---|---|---|---|---|---|
| AAT | AAT | ATG | TTT | GTT | TTT | ACT | TTA | TGT | ATT | TTA | TTA | TAC | TCG | TCT | TTT | 2527 |
| Asn | Asn | Met | Phe | Val | Phe | Thr | Leu | Cys | Ile | Leu | Leu | Tyr | Ser | Ser | Phe | |
| | 10 | | | | | 15 | | | | | 20 | | | | | |

```
TGT TAT TTT TTT TAT ATT GAA AAA ATA TTG CAA CAT ACA AAG CCA ATA        2575
Cys Tyr Phe Phe Tyr Ile Glu Lys Ile Leu Gln His Thr Lys Pro Ile
 25              30                  35                  40

TAT ACG AAC TAT GGG CAG TTG TGT ATC TGT AAA ATC AAT AAG TAT AAG        2623
Tyr Thr Asn Tyr Gly Gln Leu Cys Ile Cys Lys Ile Asn Lys Tyr Lys
                 45                  50                  55

TAT GGA TAC AGT GTC AAT ATC TTC TAT AGA CGA TGAATATTAT TATAATATAA      2676
Tyr Gly Tyr Ser Val Asn Ile Phe Tyr Arg Arg
                 60                  65

AAAATAAGCC AATATATGTA AGAAGAAAAA ATAGTTGTAG TAGTACACTA GAATCGAGAT      2736

ATTCTACATA TAGTCTAGAA TCGAGATATT CCACATATAG TATTAAATCA GTATATTTCT      2796

AAATAAATAA TA ATG AAT AAT CGT AAG TAT TCA ATA AAT AAT GGT TTT         2844
              Met Asn Asn Arg Lys Tyr Ser Ile Asn Asn Gly Phe
               1               5                   10

ATG TCA TAT TTA CGA AAG AAA TTT ACT ACA TTT TTA AGA AAG AAA TCA        2892
Met Ser Tyr Leu Arg Lys Lys Phe Thr Thr Phe Leu Arg Lys Lys Ser
         15                  20                  25

ACT TAT AGG ATA AAA TCT AAT ACC GAC TAT TAC CAG GAG AAT GAA AAG        2940
Thr Tyr Arg Ile Lys Ser Asn Thr Asp Tyr Tyr Gln Glu Asn Glu Lys
 30                  35                  40

TTG ATA CAT AAA AAT AAC ATC AAA ATA CCT TAT AAA GTA AAA GTT ATA        2988
Leu Ile His Lys Asn Asn Ile Lys Ile Pro Tyr Lys Val Lys Val Ile
 45                  50                  55                  60

AGG AAA CGT TGT AGT AGT AGC GAT GAT GAT GTT TTT ATT TAGTAAAAAA        3037
Arg Lys Arg Cys Ser Ser Ser Asp Asp Asp Val Phe Ile
                 65                  70

AACAAAAAAA ATAATAATTA AACATTCAGA CA ATG AAT ACA ACA ACT TCA CAA       3090
                                   Met Asn Thr Thr Thr Ser Gln
                                    1               5

ATA ATT ATA GAT AAT GAT ATG TCT AAT GAA GTT GGA ACA ATA ATG GTA        3138
Ile Ile Ile Asp Asn Asp Met Ser Asn Glu Val Gly Thr Ile Met Val
         10                  15                  20

ATT ACA TTA TGT TTA GTT ACT ATC GTG ATA ACG TGT TAT TTA CTA CTA        3186
Ile Thr Leu Cys Leu Val Thr Ile Val Ile Thr Cys Tyr Leu Leu Leu
 25                  30                  35

CAA TTA GTA AGA TGG TCG TTT ATA GTA GAT ATA TTT AGA CAA ATA AGA        3234
Gln Leu Val Arg Trp Ser Phe Ile Val Asp Ile Phe Arg Gln Ile Arg
 40                  45                  50                  55

ACT AGA TGT TTA CAA TGG ACA TCG AGA AGA GAA TTT TTA CAA TTA GAT AAT   3285
Thr Arg Cys Leu Gln Trp Thr Ser Arg Arg Glu Phe Leu Gln Leu Asp Asn
                 60                  65                  70

ATG TAT TAT ACG AAC GAT AGC AGC GTT GGT GTT AAT ACC GAA TAAATTGAAA   3337
Met Tyr Tyr Thr Asn Asp Ser Ser Val Gly Val Asn Thr Glu
         75                  80                  85

AATGATTTTT ATACACGA ATG GAG CCT ATT CTT CAA GAG TCT GAT TCT AGG       3388
                    Met Glu Pro Ile Leu Gln Glu Ser Asp Ser Arg
                     1               5                   10

TTC GTT ATT TTC CCT ATT AAG TAT CAT GAT ATC TGG AAA ATG TAT AAA        3436
Phe Val Ile Phe Pro Ile Lys Tyr His Asp Ile Trp Lys Met Tyr Lys
         15                  20                  25

CAA TCA GTG GCA AGT TTT TGG ACC GTT GAA GAA GTA GAT TTA TCA AAA        3484
Gln Ser Val Ala Ser Phe Trp Thr Val Glu Glu Val Asp Leu Ser Lys
 30                  35                  40

GAT TTA GAT GAT TGG GAT AAA TTA ACT AAA GAC GAA AAA TAC TTT ATA        3532
Asp Leu Asp Asp Trp Asp Lys Leu Thr Lys Asp Glu Lys Tyr Phe Ile
 45                  50                  55
```

| | | | | | | | | | | | | | | | | |
|---|---|---|---|---|---|---|---|---|---|---|---|---|---|---|---|---|
| AAA | CAT | ATA | CTA | GCA | TTT | TTT | GCA | TCT | AGT | GAT | GGT | ATT | GTA | AAT | GAG | 3580 |
| Lys | His | Ile | Leu | Ala | Phe | Phe | Ala | Ser | Ser | Asp | Gly | Ile | Val | Asn | Glu | |
| 60 | | | | 65 | | | | | 70 | | | | | 75 | | |
| AAT | TTA | GCG | GAA | AGA | TTT | TAT | GTG | GAT | GTA | CAG | TGT | TCA | GAG | GCA | CGA | 3628 |
| Asn | Leu | Ala | Glu | Arg | Phe | Tyr | Val | Asp | Val | Gln | Cys | Ser | Glu | Ala | Arg | |
| | | | 80 | | | | | 85 | | | | | 90 | | | |
| TGT | TTC | TAT | GGA | TTT | CAA | ATA | GCT | ATG | GAA | AAT | ATT | CAT | TCA | GAA | ATG | 3676 |
| Cys | Phe | Tyr | Gly | Phe | Gln | Ile | Ala | Met | Glu | Asn | Ile | His | Ser | Glu | Met | |
| | | | 95 | | | | | 100 | | | | | 105 | | | |
| TAT | AGT | TTA | TTA | ATA | GAT | ACA | TAT | GTA | AGA | GAT | AAT | ATA | GAA | AAA | ATG | 3724 |
| Tyr | Ser | Leu | Leu | Ile | Asp | Thr | Tyr | Val | Arg | Asp | Asn | Ile | Glu | Lys | Met | |
| | | 110 | | | | | 115 | | | | | 120 | | | | |
| CAT | TTA | TTT | AAC | GCT | ATA | GAA | ACA | ATG | GAA | TGC | GTA | AAA | AAG | AAA | GCT | 3772 |
| His | Leu | Phe | Asn | Ala | Ile | Glu | Thr | Met | Glu | Cys | Val | Lys | Lys | Lys | Ala | |
| | | | 125 | | | | | 130 | | | | | 135 | | | |
| GAT | TGG | GCC | AGA | AAA | TGG | ATA | TCT | AGC | AAC | AAG | GTA | TAT | GGA | GAA | AGA | 3820 |
| Asp | Trp | Ala | Arg | Lys | Trp | Ile | Ser | Ser | Asn | Lys | Val | Tyr | Gly | Glu | Arg | |
| 140 | | | | | 145 | | | | | 150 | | | | | 155 | |
| GTA | GTA | GCA | TTT | GCA | GCT | GTG | GAG | GGA | ATA | TTC | TTT | TCT | GGT | TCA | TTT | 3868 |
| Val | Val | Ala | Phe | Ala | Ala | Val | Glu | Gly | Ile | Phe | Phe | Ser | Gly | Ser | Phe | |
| | | | | 160 | | | | | 165 | | | | | 170 | | |
| GCT | GCT | ATA | TTT | TGG | ATA | AAA | AAA | CGA | GGA | TTG | ATG | CCC | GGA | TTA | ACA | 3916 |
| Ala | Ala | Ile | Phe | Trp | Ile | Lys | Lys | Arg | Gly | Leu | Met | Pro | Gly | Leu | Thr | |
| | | | 175 | | | | | 180 | | | | | 185 | | | |
| TTT | TCT | AAT | GAA | CTA | ATA | AGT | AGA | GAC | GAA | GGT | TTA | CAT | TGT | GAT | TTT | 3964 |
| Phe | Ser | Asn | Glu | Leu | Ile | Ser | Arg | Asp | Glu | Gly | Leu | His | Cys | Asp | Phe | |
| | | | 190 | | | | | 195 | | | | | 200 | | | |
| GCG | TGT | TTA | ATG | TTT | AAA | CAT | TTA | TTA | CAT | CCA | CCA | TCT | AAG | GAA | GTT | 4012 |
| Ala | Cys | Leu | Met | Phe | Lys | His | Leu | Leu | His | Pro | Pro | Ser | Lys | Glu | Val | |
| | 205 | | | | | 210 | | | | | 215 | | | | | |
| ATA | ACG | TCG | ATA | ATC | ATT | GAT | GCG | GTT | AAT | ATA | GAA | AAG | GAG | TTT | TTG | 4060 |
| Ile | Thr | Ser | Ile | Ile | Ile | Asp | Ala | Val | Asn | Ile | Glu | Lys | Glu | Phe | Leu | |
| 220 | | | | | 225 | | | | | 230 | | | | | 235 | |
| ACA | GTT | GCT | ATT | CCG | GTG | GAT | CTT | ATA | GGT | ATG | AAT | TGT | TGT | TTA | ATG | 4108 |
| Thr | Val | Ala | Ile | Pro | Val | Asp | Leu | Ile | Gly | Met | Asn | Cys | Cys | Leu | Met | |
| | | | | 240 | | | | | 245 | | | | | 250 | | |
| TCT | CAG | TAT | ATA | GAA | TTC | GTC | GCA | GAT | AGA | TTA | TTA | ACA | GAG | TTA | GGT | 4156 |
| Ser | Gln | Tyr | Ile | Glu | Phe | Val | Ala | Asp | Arg | Leu | Leu | Thr | Glu | Leu | Gly | |
| | | | 255 | | | | | 260 | | | | | 265 | | | |
| TGT | GAA | AAG | TCT | CAA | TGT | ATA | TAATCCTTTT | AGCTTTATGG | AGTATATATC | | | | | | | 4207 |
| Cys | Glu | Lys | Ser | Gln | Cys | Ile | | | | | | | | | | |
| | | 270 | | | | 275 | | | | | | | | | | |

| | |
|---|---|
| ACTAGAAGGT AAGACTAATT TTTTCGAACG ACGAGTTAGT GAATATCAAA AGATGGGGGT | 4267 |
| GTTTACAAAT AAAGAAGAGA ATATATTTTC TACGGATATA GATTTTAAT TAATAATTTT | 4327 |
| TATAAAGTTG AATAAATAAT TTAATAATAG TAATTTGCTT TGGTTTGCAA ATAGATAGTG | 4387 |

| | | | | | | | | | | | | | | | | |
|---|---|---|---|---|---|---|---|---|---|---|---|---|---|---|---|---|
| AAAA | ATG | TCT | AAA | CAA | GAA | ACT | TAC | ATT | GAT | TAT | AAC | TAT | ATA | GAA | AGG | 4436 |
| | Met | Ser | Lys | Gln | Glu | Thr | Tyr | Ile | Asp | Tyr | Asn | Tyr | Ile | Glu | Arg | |
| | 1 | | | 5 | | | | | 10 | | | | | 15 | | |
| TTA | AAT | GCT | GTG | AAT | CTA | AAC | AGA | AGT | TAT | GAT | GAA | GAG | ATA | GTA | TTT | 4484 |
| Leu | Asn | Ala | Val | Asn | Leu | Asn | Arg | Ser | Tyr | Asp | Glu | Glu | Ile | Val | Phe | |
| | | | 20 | | | | | 25 | | | | | 30 | | | |
| ATT | ATG | ACC | GTT | GGT | GGT | GTT | GTT | AAA | GTA | AAA | AAA | GAA | TTA | CTT | GTA | 4532 |
| Ile | Met | Thr | Val | Gly | Gly | Val | Val | Lys | Val | Lys | Lys | Glu | Leu | Leu | Val | |
| | | | 35 | | | | | 40 | | | | | 45 | | | |
| TCT | GTA | TCT | AAT | TAC | TTT | AAA | CTT | ATT | ACA | AAG | AAT | CAG | AGT | AAT | GAA | 4580 |
| Ser | Val | Ser | Asn | Tyr | Phe | Lys | Leu | Ile | Thr | Lys | Asn | Gln | Ser | Asn | Glu | |
| | | 50 | | | | | 55 | | | | | 60 | | | | |
| ATA | ACG | GTT | TCA | TTC | CAG | TAT | GAA | TCT | TTT | CTT | GAT | ATA | ATA | AAA | TAT | 4628 |

| | | | | | | | | | | | | | | | | |
|---|---|---|---|---|---|---|---|---|---|---|---|---|---|---|---|---|
| Ile | Thr | Val | Ser | Phe | Gln | Tyr | Glu | Ser | Phe | Leu | Asp | Ile | Ile | Lys | Tyr | |
| | 65 | | | | | 70 | | | | | 75 | | | | | |
| ATA | GAA | ACT | GGA | ATC | GTT | ACT | ATC | GAT | TTA | GAC | AAT | GTA | GAA | AAT | ATT | 4676 |
| Ile | Glu | Thr | Gly | Ile | Val | Thr | Ile | Asp | Leu | Asp | Asn | Val | Glu | Asn | Ile | |
| 80 | | | | | 85 | | | | | 90 | | | | | 95 | |
| TTT | TCC | ATA | TCT | TGT | AGT | AAA | GCC | ATA | GAT | TTT | TTA | AAA | AAT | TCA | TGT | 4724 |
| Phe | Ser | Ile | Ser | Cys | Ser | Lys | Ala | Ile | Asp | Phe | Leu | Lys | Asn | Ser | Cys | |
| | | | | 100 | | | | | 105 | | | | | 110 | | |
| ATT | GAT | TTT | ATG | TCA | AAA | CAT | ATA | ACG | GAT | TCT | ACA | TGT | GTT | AAG | ATT | 4772 |
| Ile | Asp | Phe | Met | Ser | Lys | His | Ile | Thr | Asp | Ser | Thr | Cys | Val | Lys | Ile | |
| | | | | 115 | | | | | 120 | | | | | 125 | | |
| TAC | AAA | ATA | GGT | TTC | TCG | AAT | GGA | TGT | TTT | GCG | GTA | TAT | AAT | GAT | GCT | 4820 |
| Tyr | Lys | Ile | Gly | Phe | Ser | Asn | Gly | Cys | Phe | Ala | Val | Tyr | Asn | Asp | Ala | |
| | | | 130 | | | | | 135 | | | | | 140 | | | |
| ATA | GCA | TAT | ATA | AGG | AAA | AGA | TTC | ACA | AAA | ATA | GAA | ACA | GAT | ATA | TTA | 4868 |
| Ile | Ala | Tyr | Ile | Arg | Lys | Arg | Phe | Thr | Lys | Ile | Glu | Thr | Asp | Ile | Leu | |
| | 145 | | | | | 150 | | | | | 155 | | | | | |
| CTA | TCG | TTA | TCC | TTA | TTT | GAT | TTG | AGA | ATA | ATT | CTA | AAA | AGT | GGA | GAA | 4916 |
| Leu | Ser | Leu | Ser | Leu | Phe | Asp | Leu | Arg | Ile | Ile | Leu | Lys | Ser | Gly | Glu | |
| 160 | | | | | 165 | | | | | 170 | | | | | 175 | |
| TTA | GAT | GTA | TCA | TCA | GAA | GAT | GAT | GTA | TTA | TTA | TTT | ATA | ATA | AAA | TGG | 4964 |
| Leu | Asp | Val | Ser | Ser | Glu | Asp | Asp | Val | Leu | Leu | Phe | Ile | Ile | Lys | Trp | |
| | | | | 180 | | | | | 185 | | | | | 190 | | |
| TCT | AGA | CAT | AAA | AAA | TCC | AAC | AGA | CGA | AAA | TCG | TTT | ACA | CTA | GTA | ACA | 5012 |
| Ser | Arg | His | Lys | Lys | Ser | Asn | Arg | Arg | Lys | Ser | Phe | Thr | Leu | Val | Thr | |
| | | | | 195 | | | | | 200 | | | | | 205 | | |
| GAG | GTA | CTA | AGA | TAT | AAT | TAT | CTA | TCC | ATA | TAT | GGT | AAG | TAT | AAA | TTA | 5060 |
| Glu | Val | Leu | Arg | Tyr | Asn | Tyr | Leu | Ser | Ile | Tyr | Gly | Lys | Tyr | Lys | Leu | |
| | | | 210 | | | | | 215 | | | | | 220 | | | |
| ACA | AAA | TGG | TTG | GCA | CGA | TTC | GGA | AAA | AAT | AAT | AAT | GTA | GAG | TTA | AAT | 5108 |
| Thr | Lys | Trp | Leu | Ala | Arg | Phe | Gly | Lys | Asn | Asn | Asn | Val | Glu | Leu | Asn | |
| | 225 | | | | | 230 | | | | | 235 | | | | | |
| GAA | AAT | GAA | TTA | CCT | AGA | ATA | AGT | TAT | CAA | CAT | AGA | TTT | ACA | AAC | AGA | 5156 |
| Glu | Asn | Glu | Leu | Pro | Arg | Ile | Ser | Tyr | Gln | His | Arg | Phe | Thr | Asn | Arg | |
| 240 | | | | | 245 | | | | | 250 | | | | | 255 | |
| AGA | TAT | ACG | ATG | GTT | ACA | CCA | TCT | TCA | TTT | AGT | ATA | AAT | ATG | CTA | GGT | 5204 |
| Arg | Tyr | Thr | Met | Val | Thr | Pro | Ser | Ser | Phe | Ser | Ile | Asn | Met | Leu | Gly | |
| | | | | 260 | | | | | 265 | | | | | 270 | | |
| AAT | GTA | TCT | GTT | AAG | AAT | GAA | CTT | AGT | ATA | ATC | AAT | AGT | ATA | GCT | GAG | 5252 |
| Asn | Val | Ser | Val | Lys | Asn | Glu | Leu | Ser | Ile | Ile | Asn | Ser | Ile | Ala | Glu | |
| | | | 275 | | | | | 280 | | | | | 285 | | | |
| AAT | CAT | AAT | CCT | TAC | TGT | GGA | TCT | GTA | CTT | ATG | AAT | GAT | ATA | TTA | TAT | 5300 |
| Asn | His | Asn | Pro | Tyr | Cys | Gly | Ser | Val | Leu | Met | Asn | Asp | Ile | Leu | Tyr | |
| | | 290 | | | | | 295 | | | | | 300 | | | | |
| CTT | ATA | GGT | GGT | ATA | AAT | AAA | TCA | TTG | GAT | CCT | GTT | AGT | GAT | ATA | ACT | 5348 |
| Leu | Ile | Gly | Gly | Ile | Asn | Lys | Ser | Leu | Asp | Pro | Val | Ser | Asp | Ile | Thr | |
| | 305 | | | | | 310 | | | | | 315 | | | | | |
| AGC | GTA | GAC | ACT | AGA | TCA | TTT | ATA | GAG | TTG | CAT | ACA | CCA | CCA | TTA | TTA | 5396 |
| Ser | Val | Asp | Thr | Arg | Ser | Phe | Ile | Glu | Leu | His | Thr | Pro | Pro | Leu | Leu | |
| 320 | | | | | 325 | | | | | 330 | | | | | 335 | |
| CAT | CCT | AGA | AAG | TGT | CCG | GGT | GTT | GCT | ATT | TTT | AAA | AAT | AGA | ATT | TAT | 5444 |
| His | Pro | Arg | Lys | Cys | Pro | Gly | Val | Ala | Ile | Phe | Lys | Asn | Arg | Ile | Tyr | |
| | | | | 340 | | | | | 345 | | | | | 350 | | |
| GTG | GTA | GGT | GGT | ATA | GGA | TAC | GAT | GGA | CCA | TTA | AAA | ACA | GTA | GAA | AGT | 5492 |
| Val | Val | Gly | Gly | Ile | Gly | Tyr | Asp | Gly | Pro | Leu | Lys | Thr | Val | Glu | Ser | |
| | | | 355 | | | | | 360 | | | | | 365 | | | |
| TGG | TCA | CCT | GGA | GAA | CAA | CAA | TGG | AGA | GAA | GAA | GTA | CCA | TTA | TTA | CAA | 5540 |
| Trp | Ser | Pro | Gly | Glu | Gln | Gln | Trp | Arg | Glu | Glu | Val | Pro | Leu | Leu | Gln | |
| | | 370 | | | | | 375 | | | | | 380 | | | | |
| CCC | AGA | TTT | AAT | CCT | TGC | ATA | ATT | GGA | ACA | GAT | AAT | GAT | TTA | TAT | GTT | 5588 |

```
        Pro  Arg  Phe  Asn  Pro  Cys  Ile  Ile  Gly  Thr  Asp  Asn  Asp  Leu  Tyr  Val
             385                     390                          395

GTT  GGT  GGT  ATT  TCT  GAA  GAT  GAT  AAA  ACT  ATT  GAA  ATC  TAT  TCT  TAT             5636
Val  Gly  Gly  Ile  Ser  Glu  Asp  Asp  Lys  Thr  Ile  Glu  Ile  Tyr  Ser  Tyr
400                     405                          410                     415

GAA  GAA  AAC  ACT  TGG  TCT  ATT  GGT  AAT  GCG  ATG  AAT  TAT  TCA  CAT  TTT             5684
Glu  Glu  Asn  Thr  Trp  Ser  Ile  Gly  Asn  Ala  Met  Asn  Tyr  Ser  His  Phe
                         420                          425                     430

GGT  GGA  TGT  ATA  GCA  TAT  CAC  CAT  GGT  TAT  ATA  TAT  ATG  ATT  GGT  GGT             5732
Gly  Gly  Cys  Ile  Ala  Tyr  His  His  Gly  Tyr  Ile  Tyr  Met  Ile  Gly  Gly
                    435                          440                     445

TTA  TCT  TTT  ATA  GAT  AAT  ATT  CAT  GTA  TTT  ACT  ATG  GTT  GAG  AAG  TAT             5780
Leu  Ser  Phe  Ile  Asp  Asn  Ile  His  Val  Phe  Thr  Met  Val  Glu  Lys  Tyr
               450                          455                     460

AAC  CCT  CAT  TCG  AAT  AAA  TGG  ACT  GTA  GAA  AAG  TCT  CTA  CCC  TTT  CCT             5828
Asn  Pro  His  Ser  Asn  Lys  Trp  Thr  Val  Glu  Lys  Ser  Leu  Pro  Phe  Pro
          465                          470                     475

CGA  TTT  AAT  TCA  TCG  CTT  TGT  ATT  ATA  GAA  GAC  TCT  ATC  GCT  ATA  ATA             5876
Arg  Phe  Asn  Ser  Ser  Leu  Cys  Ile  Ile  Glu  Asp  Ser  Ile  Ala  Ile  Ile
480                     485                          490                     495

GGC  TGG  ATA  TAT  TAT  TAACAAATAT  ATTAGTCAAA  TAGAAATATA  TAACGGAGCT                    5931
Gly  Trp  Ile  Tyr  Tyr
                    500

AGATGAATGG  GGTATTGTAG  GGTCTATCGA  TATAGAGTCA  TTCTTTCAAG  AAATGAAAAA                      5991

ATAATCTACA  TTTTTTCTTG  TTACGACAAT  GGAACTACGT  TATACGATCA  TATCTGTCTG                      6051

TGCTTGAAAG  GTTGACACCG  TATCAGTTTA  AAACGTTATT  ATTCTTGATA  CAGGATGACA                      6111

TTAATATATC  TAACGATGAT  ATTAATGTAT  TAGATAGAGT  CGATCTAGCT  ATTAAAATA                       6170

ATG  AAT  AAA  TAT  AAT  AAT  TAT  AGA  GCA  ATT  TAT  TTT  CTC  TAT  AAA  GTC             6218
Met  Asn  Lys  Tyr  Asn  Asn  Tyr  Arg  Ala  Ile  Tyr  Phe  Leu  Tyr  Lys  Val
  1                 5                        10                     15

ATA  TTA  CGA  ATA  CAT  AAT  ACA  GAA  TAT  ATA  AGT  GGA  ACA  CTA  CAA  AGA             6266
Ile  Leu  Arg  Ile  His  Asn  Thr  Glu  Tyr  Ile  Ser  Gly  Thr  Leu  Gln  Arg
               20                          25                     30

TCT  ATA  CAG  AAT  ATA  ACA  CCT  ACA  ACA  TCA  TCA  TAT  ACG  TAT  TGT  GAT             6314
Ser  Ile  Gln  Asn  Ile  Thr  Pro  Thr  Thr  Ser  Ser  Tyr  Thr  Tyr  Cys  Asp
          35                          40                     45

AAT  TCA  AAA  AGA  CGC  AGA  CAT  AGA  TTT  AGA  GAT  ACG  GAA  ATC  CTT  AAA             6362
Asn  Ser  Lys  Arg  Arg  Arg  His  Arg  Phe  Arg  Asp  Thr  Glu  Ile  Leu  Lys
     50                          55                     60

GCT  ATG  GGT  AGT  AAA  ATG  CGT  AGA  AAA  CTT  TTT  TAGTTAGTGA  GTAATATTAT               6415
Ala  Met  Gly  Ser  Lys  Met  Arg  Arg  Lys  Leu  Phe
 65                     70                     75

AAAATTAAAA  AAAAAATAAT  ATTTCTAGA  C ATG  TCA  CTA  TAT  GTT  AAA  TGT                      6467
                                     Met  Ser  Leu  Tyr  Val  Lys  Cys
                                       1                      5

GTT  AAG  TTA  TCT  AAT  AAT  GCT  ATT  ATA  CCA  AAT  AGA  TCA  ATG  AGC  GGA             6515
Val  Lys  Leu  Ser  Asn  Asn  Ala  Ile  Ile  Pro  Asn  Arg  Ser  Met  Ser  Gly
               10                          15                     20

TCC  GCT  GGA  TAT  GAT  CTG  TAT  AGT  GCA  TAT  AGT  TAT  ACA  GTT  AAG  CCG             6563
Ser  Ala  Gly  Tyr  Asp  Leu  Tyr  Ser  Ala  Tyr  Ser  Tyr  Thr  Val  Lys  Pro
 25                      30                          35

TAT  AAT  AGA  ATT  TTA  GTT  AGA  ACA  GAT  ATT  TGT  TTA  ATG  ATA  CCA  GAT             6611
Tyr  Asn  Arg  Ile  Leu  Val  Arg  Thr  Asp  Ile  Cys  Leu  Met  Ile  Pro  Asp
 40                      45                          50                     55

AAA  TGT  TAT  GGA  CGC  ATA  TCG  CCT  AGA  TCG  GGA  TTA  TCG  TTA  AAT  TAT             6659
Lys  Cys  Tyr  Gly  Arg  Ile  Ser  Pro  Arg  Ser  Gly  Leu  Ser  Leu  Asn  Tyr
                    60                          65                     70
```

| | | | | | | | | | | | | | | | | |
|---|---|---|---|---|---|---|---|---|---|---|---|---|---|---|---|---|
| AAT | ATA | GAT | ATA | GGA | GGA | GGC | GTT | ATT | GAT | AGT | GAT | TAC | AGA | GGG | GAA | 6707 |
| Asn | Ile | Asp | Ile | Gly | Gly | Gly | Val | Ile | Asp | Ser | Asp | Tyr | Arg | Gly | Glu | |
| | | | 75 | | | | 80 | | | | | 85 | | | | |
| ATA | GGT | ATC | GTG | TTT | ATA | AAT | AAT | GGA | TGT | AGT | GAT | TTT | AAC | ATA | AAG | 6755 |
| Ile | Gly | Ile | Val | Phe | Ile | Asn | Asn | Gly | Cys | Ser | Asp | Phe | Asn | Ile | Lys | |
| | | 90 | | | | | 95 | | | | | 100 | | | | |
| GTA | GGT | GAT | AGG | ATA | GCA | CAA | ATA | ATA | TTT | GAA | AGA | GTA | GAA | TAT | CCT | 6803 |
| Val | Gly | Asp | Arg | Ile | Ala | Gln | Ile | Ile | Phe | Glu | Arg | Val | Glu | Tyr | Pro | |
| | | 105 | | | | 110 | | | | | 115 | | | | | |
| ATA | ATG | GAA | GAA | GTA | AAA | TGT | TTG | GAA | GAT | ACA | GAA | CGT | GGA | AAT | AGT | 6851 |
| Ile | Met | Glu | Glu | Val | Lys | Cys | Leu | Glu | Asp | Thr | Glu | Arg | Gly | Asn | Ser | |
| 120 | | | | | 125 | | | | | 130 | | | | | 135 | |
| GGT | TTT | GGG | TCA | AGT | GGT | ATG | TAAAGTATAA | | TAAATGAAAA | | AATAATTCAT | | | | | 6902 |
| Gly | Phe | Gly | Ser | Ser | Gly | Met | | | | | | | | | | |
| | | | | | | 140 | | | | | | | | | | |
| CTGTATTATA | | TCCATTATTA | | TCAAT | ATG | TAC | AAG | AAA | TAT | AAC | TCT | AAC | GTA | | | 6954 |
| | | | | | Met | Tyr | Lys | Lys | Tyr | Asn | Ser | Asn | Val | | | |
| | | | | | 1 | | | | 5 | | | | | | | |
| TGC | ATT | AGG | AAT | GTA | TTA | TAT | GTA | TAT | CTA | AAA | TAT | AAT | ACT | ATA | AAT | 7002 |
| Cys | Ile | Arg | Asn | Val | Leu | Tyr | Val | Tyr | Leu | Lys | Tyr | Asn | Thr | Ile | Asn | |
| 10 | | | | | 15 | | | | | 20 | | | | | 25 | |
| AAA | CTT | AGT | AGA | TAT | GAA | CGG | ATG | ATA | TAC | ACA | AAG | ATA | AAA | AAT | CAA | 7050 |
| Lys | Leu | Ser | Arg | Tyr | Glu | Arg | Met | Ile | Tyr | Thr | Lys | Ile | Lys | Asn | Gln | |
| | | | | 30 | | | | | 35 | | | | | 40 | | |
| TGT | GAA | GCG | ATA | AAA | TAC | AGA | TAT | TGT | AAT | GAT | TTT | AAT | TCT | GTT | ACA | 7098 |
| Cys | Glu | Ala | Ile | Lys | Tyr | Arg | Tyr | Cys | Asn | Asp | Phe | Asn | Ser | Val | Thr | |
| | | | 45 | | | | | 50 | | | | | 55 | | | |
| TGT | ATT | TTA | GAA | TAC | GAT | GAA | AAT | AAG | TAT | ATA | GAT | AAC | GTG | CAT | AAA | 7146 |
| Cys | Ile | Leu | Glu | Tyr | Asp | Glu | Asn | Lys | Tyr | Ile | Asp | Asn | Val | His | Lys | |
| | | 60 | | | | | 65 | | | | | 70 | | | | |
| GAA | GTT | ATT | AGT | ATA | TTG | TTA | TCA | GAT | TCG | CGA | CCT | AGT | ATC | AAA | TTA | 7194 |
| Glu | Val | Ile | Ser | Ile | Leu | Leu | Ser | Asp | Ser | Arg | Pro | Ser | Ile | Lys | Leu | |
| | 75 | | | | | 80 | | | | | 85 | | | | | |
| GCT | GCT | ATT | TCG | TTA | TTA | TCT | ATA | ATA | ATA | GAT | AAA | CTA | ATA | TGT | AGA | 7242 |
| Ala | Ala | Ile | Ser | Leu | Leu | Ser | Ile | Ile | Ile | Asp | Lys | Leu | Ile | Cys | Arg | |
| 90 | | | | | 95 | | | | | 100 | | | | | 105 | |
| AAT | ATT | CGT | ATA | GCT | AAA | TAT | ATA | ATT | GAT | GAT | ATA | ATA | AAT | ATT | ATA | 7290 |
| Asn | Ile | Arg | Ile | Ala | Lys | Tyr | Ile | Ile | Asp | Asp | Ile | Ile | Asn | Ile | Ile | |
| | | | | 110 | | | | | 115 | | | | | 120 | | |
| TCA | GAA | GAC | GGT | ATA | TAT | ATT | ATA | TTA | TTT | TTA | GAT | GAA | TTT | GAT | AAA | 7338 |
| Ser | Glu | Asp | Gly | Ile | Tyr | Ile | Ile | Leu | Phe | Leu | Asp | Glu | Phe | Asp | Lys | |
| | | | 125 | | | | | 130 | | | | | 135 | | | |
| TAT | ACC | GAT | ACC | CGA | TGT | AGG | CGC | CGT | GGA | TTA | AGT | ATG | ATG | ATA | GCG | 7386 |
| Tyr | Thr | Asp | Thr | Arg | Cys | Arg | Arg | Arg | Gly | Leu | Ser | Met | Met | Ile | Ala | |
| | | 140 | | | | 145 | | | | | 150 | | | | | |
| AGC | ATT | GTA | ACT | TAC | TAC | TGT | TTA | CGG | TAT | GTA | TTA | AAA | ATA | TAAAAATAAA | | 7438 |
| Ser | Ile | Val | Thr | Tyr | Tyr | Cys | Leu | Arg | Tyr | Val | Leu | Lys | Ile | | | |
| | 155 | | | | 160 | | | | | 165 | | | | | | |
| TCTTTTTTTT | | TAAAA | ATG | AAC | CGT | AAT | ATG | TGG | ATA | GTG | TTA | TCG | TGT | GTA | | 7489 |
| | | | Met | Asn | Arg | Asn | Met | Trp | Ile | Val | Leu | Ser | Cys | Val | | |
| | | | 1 | | | | 5 | | | | | 10 | | | | |
| TTA | TAT | ATG | ATT | TAT | ATA | TGT | AAC | GGA | CGA | GAT | GTA | TTG | TTA | TAT | CCA | 7537 |
| Leu | Tyr | Met | Ile | Tyr | Ile | Cys | Asn | Gly | Arg | Asp | Val | Leu | Leu | Tyr | Pro | |
| | | | 15 | | | | 20 | | | | | 25 | | | | |
| CCA | CAT | AAG | AAA | ACA | AAT | AAG | GTT | ATA | GTA | AAA | TGT | AAC | GGA | TAT | ACT | 7585 |
| Pro | His | Lys | Lys | Thr | Asn | Lys | Val | Ile | Val | Lys | Cys | Asn | Gly | Tyr | Thr | |
| | | 30 | | | | 35 | | | | | 40 | | | | | |
| AAT | TCT | ACG | TAT | AGT | ATC | TTA | TAT | TGG | ATG | GTA | GGT | AAC | AAC | AAT | ACA | 7633 |
| Asn | Ser | Thr | Tyr | Ser | Ile | Leu | Tyr | Trp | Met | Val | Gly | Asn | Asn | Asn | Thr | |

5,651,972

-continued

| | 45 | | | | 50 | | | | 55 | | | | 60 | | | |
|---|---|---|---|---|---|---|---|---|---|---|---|---|---|---|---|---|
| TTC | GTA | GAA | CAA | CTA | AAT | AGC | GAT | CAT | TAT | AAA | GAG | AAG | AAA | TAC | AAT | 7681 |
| Phe | Val | Glu | Gln | Leu | Asn | Ser | Asp | His | Tyr | Lys | Glu | Lys | Lys | Tyr | Asn | |
| | | | | | 65 | | | | 70 | | | | 75 | | | |
| AGT | ACT | GAA | AAA | AAT | GAG | CAT | ATG | TAT | AAG | TTA | CGT | ACC | GAT | CTT | ATT | 7729 |
| Ser | Thr | Glu | Lys | Asn | Glu | His | Met | Tyr | Lys | Leu | Arg | Thr | Asp | Leu | Ile | |
| | | | 80 | | | | | 85 | | | | | 90 | | | |
| ATA | TAT | AAT | ATT | ACG | TCA | GAA | ATG | GAG | ATG | ACA | AAA | CTA | ACA | TGT | GTA | 7777 |
| Ile | Tyr | Asn | Ile | Thr | Ser | Glu | Met | Glu | Met | Thr | Lys | Leu | Thr | Cys | Val | |
| | | 95 | | | | | 100 | | | | | 105 | | | | |
| TTA | TCA | GAT | ATA | TAC | ACA | CCT | ATC | AAG | GCA | TCT | ATA | ATA | TTA | AAT | AAT | 7825 |
| Leu | Ser | Asp | Ile | Tyr | Thr | Pro | Ile | Lys | Ala | Ser | Ile | Ile | Leu | Asn | Asn | |
| | 110 | | | | | 115 | | | | | 120 | | | | | |
| TTA | TGG | AGT | TGT | TTA | AAT | ACT | ACA | CAA | GTA | TGAAATATGA | | AATATAAAGT | | | | 7875 |
| Leu | Trp | Ser | Cys | Leu | Asn | Thr | Thr | Gln | Val | | | | | | | |
| 125 | | | | | 130 | | | | | 135 | | | | | | |
| ATTCAAATAA | | ATAACAATA | | ATG | TCA | ACT | ATG | AAT | ACG | TTG | GCA | TTT | TGT | TAT | | 7927 |
| | | | | Met | Ser | Thr | Met | Asn | Thr | Leu | Ala | Phe | Cys | Tyr | | |
| | | | | 1 | | | | 5 | | | | | 10 | | | |
| GGA | TTA | CCT | AAC | ATA | AAT | GAT | ATC | ACG | CAA | GGT | ATA | ATT | TTT | GTT | AGA | 7975 |
| Gly | Leu | Pro | Asn | Ile | Asn | Asp | Ile | Thr | Gln | Gly | Ile | Ile | Phe | Val | Arg | |
| | | | 15 | | | | | 20 | | | | | 25 | | | |
| AAT | AAC | ATA | TTT | TAC | TCA | TAT | TTA | ACA | GAT | TAT | GCA | ATG | GAA | GCG | TGT | 8023 |
| Asn | Asn | Ile | Phe | Tyr | Ser | Tyr | Leu | Thr | Asp | Tyr | Ala | Met | Glu | Ala | Cys | |
| | | 30 | | | | | 35 | | | | | 40 | | | | |
| ATA | TTG | AAT | TAT | ATA | AAT | ATT | AGA | GCC | GAT | AAA | ATA | GAA | GAT | CTA | AAG | 8071 |
| Ile | Leu | Asn | Tyr | Ile | Asn | Ile | Arg | Ala | Asp | Lys | Ile | Glu | Asp | Leu | Lys | |
| | 45 | | | | | 50 | | | | | 55 | | | | | |
| AAA | TCA | TTA | GTT | GGA | AAA | ACT | ATT | AGC | GTG | AGA | GTT | ATT | AGA | GTT | GAT | 8119 |
| Lys | Ser | Leu | Val | Gly | Lys | Thr | Ile | Ser | Val | Arg | Val | Ile | Arg | Val | Asp | |
| 60 | | | | | 65 | | | | | 70 | | | | | 75 | |
| GTA | TTA | AAA | GGA | TAT | ATA | GAT | GTT | TCA | ATT | GTA | TAATTTTTT | | ATCAAAACTG | | | 8172 |
| Val | Leu | Lys | Gly | Tyr | Ile | Asp | Val | Ser | Ile | Val | | | | | | |
| | | | 80 | | | | | 85 | | | | | | | | |
| AAGTATAATC | | TAGACCTTAG | | AAGATATTTT | | GTACCATATA | | AA | ATG | GAT | CCT | GTT | | | | 8226 |
| | | | | | | | | | Met | Asp | Pro | Val | | | | |
| | | | | | | | | | 1 | | | | | | | |
| TGT | TGG | ATA | TGT | AAA | GAT | GAC | TAC | AGT | ATT | GAA | AAG | AAT | TAT | TGT | AAC | 8274 |
| Cys | Trp | Ile | Cys | Lys | Asp | Asp | Tyr | Ser | Ile | Glu | Lys | Asn | Tyr | Cys | Asn | |
| 5 | | | | 10 | | | | | 15 | | | | | 20 | | |
| TGT | AAA | AAC | GAG | TAT | AAA | GTT | GTA | CAC | GAT | GAA | TGT | ATG | AAA | AAG | TGG | 8322 |
| Cys | Lys | Asn | Glu | Tyr | Lys | Val | Val | His | Asp | Glu | Cys | Met | Lys | Lys | Trp | |
| | | | | 25 | | | | 30 | | | | | 35 | | | |
| ATA | CAA | TAC | TCA | AGG | GAA | CGA | TCT | TGT | AAA | TTA | TGT | AAT | AAA | GAA | TAT | 8370 |
| Ile | Gln | Tyr | Ser | Arg | Glu | Arg | Ser | Cys | Lys | Leu | Cys | Asn | Lys | Glu | Tyr | |
| | | 40 | | | | | 45 | | | | | 50 | | | | |
| AAC | ATC | ATT | AGT | GTT | AGA | AAA | CCA | TTC | TCA | CAG | TGG | GTA | TTC | TCC | ATT | 8418 |
| Asn | Ile | Ile | Ser | Val | Arg | Lys | Pro | Phe | Ser | Gln | Trp | Val | Phe | Ser | Ile | |
| | 55 | | | | | 60 | | | | | 65 | | | | | |
| AAA | GAT | TGC | AAA | AAG | TCA | GCA | ATT | TTG | TAC | GCT | ACT | CTA | TTC | TTA | TGT | 8466 |
| Lys | Asp | Cys | Lys | Lys | Ser | Ala | Ile | Leu | Tyr | Ala | Thr | Leu | Phe | Leu | Cys | |
| 70 | | | | | 75 | | | | | 80 | | | | | | |
| ACG | TTT | ATT | ATA | TCG | CTT | GTT | TTA | ACT | AGA | ATT | AAT | ATA | ACA | AAA | ATA | 8514 |
| Thr | Phe | Ile | Ile | Ser | Leu | Val | Leu | Thr | Arg | Ile | Asn | Ile | Thr | Lys | Ile | |
| 85 | | | | | 90 | | | | | 95 | | | | | 100 | |
| ATA | GAT | ACA | TCA | AAA | AAT | GAT | GTT | TCA | TTT | AAG | CTG | GTT | ACG | ATG | ATA | 8562 |
| Ile | Asp | Thr | Ser | Lys | Asn | Asp | Val | Ser | Phe | Lys | Leu | Val | Thr | Met | Ile | |
| | | | 105 | | | | | 110 | | | | | 115 | | | |

-continued

| | | | | | | | | | | | | | | | | |
|---|---|---|---|---|---|---|---|---|---|---|---|---|---|---|---|---|
| TTC | TAC | TTA | TTA | CCA | TTT | GTC | ATA | ACT | TGT | ATA | TCG | TTC | ATA | ACG | CTG | 8610 |
| Phe | Tyr | Leu | Leu | Pro | Phe | Val | Ile | Thr | Cys | Ile | Ser | Phe | Ile | Thr | Leu | |
| | | | 120 | | | | 125 | | | | | 130 | | | | |
| ATA | GTT | TAT | CTA | TAT | AAA | TAT | TGT | AAG | ATT | TCC | GCT | AAA | AAC | AAC | ACA | 8658 |
| Ile | Val | Tyr | Leu | Tyr | Lys | Tyr | Cys | Lys | Ile | Ser | Ala | Lys | Asn | Asn | Thr | |
| | | 135 | | | | 140 | | | | | 145 | | | | | |
| TAC | GAT | ACG | ATT | TAT | GAA | CTT | TAAAGTGAAA | | ATTTAATCTA | | TTTTTATAAT | | | | | 8709 |
| Tyr | Asp | Thr | Ile | Tyr | Glu | Leu | | | | | | | | | | |
| | 150 | | | | 155 | | | | | | | | | | | |
| AAAAC | ATG | CAT | TTC | ATA | TTC | ATT | ATA | TTA | TCA | CTA | TCA | TTT | GTA | GTA | | 8756 |
| | Met | His | Phe | Ile | Phe | Ile | Ile | Leu | Ser | Leu | Ser | Phe | Val | Val | | |
| | 1 | | | 5 | | | | | 10 | | | | | | | |
| AAT | GCC | GAT | GTA | TTT | CCA | TCG | TCG | GTT | ACT | TTA | TCA | TCT | AAT | GAT | TTT | 8804 |
| Asn | Ala | Asp | Val | Phe | Pro | Ser | Ser | Val | Thr | Leu | Ser | Ser | Asn | Asp | Phe | |
| 15 | | | | 20 | | | | | 25 | | | | | | 30 | |
| GAT | ACA | ATA | ATT | AAA | TGG | GAT | AAT | AAT | GTA | ATA | TCA | TAC | GAT | GTA | GAA | 8852 |
| Asp | Thr | Ile | Ile | Lys | Trp | Asp | Asn | Asn | Val | Ile | Ser | Tyr | Asp | Val | Glu | |
| | | | | 35 | | | | 40 | | | | | 45 | | | |
| TTA | ATG | CAG | TAC | AGT | CAT | GAC | GAA | TGG | AGA | ACC | GTT | TGT | ACT | AAT | TCT | 8900 |
| Leu | Met | Gln | Tyr | Ser | His | Asp | Glu | Trp | Arg | Thr | Val | Cys | Thr | Asn | Ser | |
| | | | 50 | | | | | 55 | | | | | 60 | | | |
| TTA | GGA | TAC | TGT | AAT | TTA | ACA | AAT | TCT | GAT | ATC | GAC | AAT | GAT | GAT | GAA | 8948 |
| Leu | Gly | Tyr | Cys | Asn | Leu | Thr | Asn | Ser | Asp | Ile | Asp | Asn | Asp | Asp | Glu | |
| | | 65 | | | | 70 | | | | | | 75 | | | | |
| ACA | TGG | GTG | AGG | TTT | AAA | TAT | GAA | AAT | AAG | ACA | TCT | AAT | GAA | CAT | AAT | 8996 |
| Thr | Trp | Val | Arg | Phe | Lys | Tyr | Glu | Asn | Lys | Thr | Ser | Asn | Glu | His | Asn | |
| | | 80 | | | | 85 | | | | | 90 | | | | | |
| ATT | GGC | AGA | GTA | TGT | GAG | ATT | GTA | CAA | ATA | ACT | TCA | CCT | ATT | GTT | AAC | 9044 |
| Ile | Gly | Arg | Val | Cys | Glu | Ile | Val | Gln | Ile | Thr | Ser | Pro | Ile | Val | Asn | |
| 95 | | | | | 100 | | | | | 105 | | | | | 110 | |
| ATG | ACA | AGA | GAT | GGT | TCA | ATT | ATA | CTA | TTA | GAT | ATA | CAT | CAT | CCA | ATG | 9092 |
| Met | Thr | Arg | Asp | Gly | Ser | Ile | Ile | Leu | Leu | Asp | Ile | His | His | Pro | Met | |
| | | | | | 115 | | | | | 120 | | | | | 125 | |
| ACA | TAC | GAT | AAT | CAG | TAT | TAT | ATA | TAT | AAT | AAT | ATA | ACA | TTA | TGT | GGA | 9140 |
| Thr | Tyr | Asp | Asn | Gln | Tyr | Tyr | Ile | Tyr | Asn | Asn | Ile | Thr | Leu | Cys | Gly | |
| | | | 130 | | | | | 135 | | | | | 140 | | | |
| TTT | GAA | TTT | ATT | TAC | GAA | GCT | ACA | TTT | ATT | ATT | AAT | GAT | ACA | ATT | ATA | 9188 |
| Phe | Glu | Phe | Ile | Tyr | Glu | Ala | Thr | Phe | Ile | Ile | Asn | Asp | Thr | Ile | Ile | |
| | | 145 | | | | | 150 | | | | | 155 | | | | |
| CCA | TAT | AGT | ATA | GAC | AAT | CAA | TAT | TGT | GAT | GAT | GTT | CAT | TGT | TTA | TTT | 9236 |
| Pro | Tyr | Ser | Ile | Asp | Asn | Gln | Tyr | Cys | Asp | Asp | Val | His | Cys | Leu | Phe | |
| | | 160 | | | | | 165 | | | | | 170 | | | | |
| TAC | TTT | ATA | TCA | CAA | GAA | CCC | GTT | TGT | GTG | TAT | GTA | ATG | GGT | ATG | GAA | 9284 |
| Tyr | Phe | Ile | Ser | Gln | Glu | Pro | Val | Cys | Val | Tyr | Val | Met | Gly | Met | Glu | |
| 175 | | | | | 180 | | | | | 185 | | | | | 190 | |
| CAA | TAT | TAT | GAA | TTT | GGT | CCA | AAA | AAA | ACA | GAT | AAT | AGT | ACT | AGA | GTG | 9332 |
| Gln | Tyr | Tyr | Glu | Phe | Gly | Pro | Lys | Lys | Thr | Asp | Asn | Ser | Thr | Arg | Val | |
| | | | | 195 | | | | | 200 | | | | | 205 | | |
| TGT | GTA | GAT | GGA | TTA | ATT | CCA | AGA | AAA | ATC | GAT | ACA | TAT | TTT | ATT | AAA | 9380 |
| Cys | Val | Asp | Gly | Leu | Ile | Pro | Arg | Lys | Ile | Asp | Thr | Tyr | Phe | Ile | Lys | |
| | | | 210 | | | | 215 | | | | | 220 | | | | |
| GAT | TTC | GAT | GAT | ATA | GAT | AGA | GTT | AAT | AAC | AGA | TTA | TAT | AGA | GTT | GTA | 9428 |
| Asp | Phe | Asp | Asp | Ile | Asp | Arg | Val | Asn | Asn | Arg | Leu | Tyr | Arg | Val | Val | |
| | | 225 | | | | | 230 | | | | | 235 | | | | |
| AGT | GAT | AAA | TAT | GAA | TCC | AAT | ATA | TCG | TCA | AAG | TTT | ATG | CAC | TTA | TAT | 9476 |
| Ser | Asp | Lys | Tyr | Glu | Ser | Asn | Ile | Ser | Ser | Lys | Phe | Met | His | Leu | Tyr | |
| | | 240 | | | | 245 | | | | | 250 | | | | | |
| AAT | AAT | ATA | TTA | TCT | TCG | TTT | AAA | CTA | ATA | TTG | CAA | GAA | CTT | ATG | GTA | 9524 |
| Asn | Asn | Ile | Leu | Ser | Ser | Phe | Lys | Leu | Ile | Leu | Gln | Glu | Leu | Met | Val | |
| 255 | | | | 260 | | | | | 265 | | | | | 270 | | |

| | | | | | | | | | | | | | | | | |
|---|---|---|---|---|---|---|---|---|---|---|---|---|---|---|---|---|
| AAT | ACT | GAA | CAG | TAAATACGTT | TATAAAGATA | AAGGA | ATG | AAT | TCG | TAT | ATT | | | | | 9576 |
| Asn | Thr | Glu | Gln | | | | Met | Asn | Ser | Tyr | Ile | | | | | |
| | | | 275 | | | | 1 | | | | 5 | | | | | |

| | | | | | | | | | | | | | | | | |
|---|---|---|---|---|---|---|---|---|---|---|---|---|---|---|---|---|
| GTA | ATA | AAA | AAT | TCA | TTA | CGT | GAT | TAT | AGA | TCT | GGA | AGA | ATT | ATA | AGA | 9624 |
| Val | Ile | Lys | Asn | Ser | Leu | Arg | Asp | Tyr | Arg | Ser | Gly | Arg | Ile | Ile | Arg | |
| | | | | 10 | | | | | 15 | | | | | 20 | | |

| | | | | | | | | | | | | | | | | |
|---|---|---|---|---|---|---|---|---|---|---|---|---|---|---|---|---|
| AAA | TAC | ATA | AGA | AAA | TTA | AAT | AAG | GAT | GAG | TAT | AAG | CAT | TTT | TGT | GCT | 9672 |
| Lys | Tyr | Ile | Arg | Lys | Leu | Asn | Lys | Asp | Glu | Tyr | Lys | His | Phe | Cys | Ala | |
| | | | 25 | | | | | 30 | | | | | 35 | | | |

| | | | | | | | | | | | | | | | | |
|---|---|---|---|---|---|---|---|---|---|---|---|---|---|---|---|---|
| GTA | TTT | AGA | TTA | AAT | GTA | GAT | TTT | TCT | CAA | GAT | GAT | AAA | AAT | CCA | TCT | 9720 |
| Val | Phe | Arg | Leu | Asn | Val | Asp | Phe | Ser | Gln | Asp | Asp | Lys | Asn | Pro | Ser | |
| | | 40 | | | | | 45 | | | | | 50 | | | | |

| | | | | | | | | | | | | | | | | |
|---|---|---|---|---|---|---|---|---|---|---|---|---|---|---|---|---|
| AGA | AAA | GAA | GTA | ATA | AGA | ATA | ATA | GAT | GAG | GAA | TTC | AAT | TTT | TGT | GAT | 9768 |
| Arg | Lys | Glu | Val | Ile | Arg | Ile | Ile | Asp | Glu | Glu | Phe | Asn | Phe | Cys | Asp | |
| | 55 | | | | | 60 | | | | | 65 | | | | | |

| | | | | | | | | | | | | | | | | |
|---|---|---|---|---|---|---|---|---|---|---|---|---|---|---|---|---|
| CTT | AGA | CTA | TTT | TAT | GAT | ATC | ATG | ACC | GTT | GTA | CCT | AAT | CAT | ATG | AAT | 9816 |
| Leu | Arg | Leu | Phe | Tyr | Asp | Ile | Met | Thr | Val | Val | Pro | Asn | His | Met | Asn | |
| 70 | | | | | 75 | | | | | 80 | | | | | 85 | |

| | | | | | | | | | | | | | | | | |
|---|---|---|---|---|---|---|---|---|---|---|---|---|---|---|---|---|
| GTG | GCA | TCT | ATT | ATT | TAT | AGC | GAA | TAC | GAA | TAT | CTT | TTA | AAA | AAA | TCA | 9864 |
| Val | Ala | Ser | Ile | Ile | Tyr | Ser | Glu | Tyr | Glu | Tyr | Leu | Leu | Lys | Lys | Ser | |
| | | | | 90 | | | | | 95 | | | | | 100 | | |

| | | | | | | | | | | | | | | | | |
|---|---|---|---|---|---|---|---|---|---|---|---|---|---|---|---|---|
| AAT | TAT | AAA | AAT | AAG | AAG | ATA | AAT | TAT | ACT | ATA | TTA | GAT | AAG | ATT | AAT | 9912 |
| Asn | Tyr | Lys | Asn | Lys | Lys | Ile | Asn | Tyr | Thr | Ile | Leu | Asp | Lys | Ile | Asn | |
| | | | 105 | | | | | 110 | | | | | 115 | | | |

| | | | | | | | | | | | | | | | | |
|---|---|---|---|---|---|---|---|---|---|---|---|---|---|---|---|---|
| AAA | TAT | CAT | AGT | ATA | GAT | GAT | ATT | ATA | TTT | ATG | TAT | CTT | CAT | TGG | AGA | 9960 |
| Lys | Tyr | His | Ser | Ile | Asp | Asp | Ile | Ile | Phe | Met | Tyr | Leu | His | Trp | Arg | |
| | | 120 | | | | | 125 | | | | | 130 | | | | |

| | | | | | | | | | | | | | | | | |
|---|---|---|---|---|---|---|---|---|---|---|---|---|---|---|---|---|
| AAA | AAA | TAT | AAC | AAC | ACA | TGC | GCA | TGT | GGT | AAG | TTA | TTT | AAG | GAA | CTC | 10008 |
| Lys | Lys | Tyr | Asn | Asn | Thr | Cys | Ala | Cys | Gly | Lys | Leu | Phe | Lys | Glu | Leu | |
| 135 | | | | | 140 | | | | | 145 | | | | | | |

| | | | | | | | | | | | | | | | | |
|---|---|---|---|---|---|---|---|---|---|---|---|---|---|---|---|---|
| ATG | AAA | TAT | GAT | ATA | TTA | GCT | ACA | AAA | TAT | ATA | TAT | AAT | GAT | ATT | ATA | 10056 |
| Met | Lys | Tyr | Asp | Ile | Leu | Ala | Thr | Lys | Tyr | Ile | Tyr | Asn | Asp | Ile | Ile | |
| 150 | | | | | 155 | | | | | 160 | | | | | 165 | |

| | | | | | | | | | | | | | | | | |
|---|---|---|---|---|---|---|---|---|---|---|---|---|---|---|---|---|
| AAT | ACA | TAC | AAA | GAG | GGA | GAT | ACT | ATA | TCC | ATT | AAC | ATA | CGT | TTA | AAA | 10104 |
| Asn | Thr | Tyr | Lys | Glu | Gly | Asp | Thr | Ile | Ser | Ile | Asn | Ile | Arg | Leu | Lys | |
| | | | | 170 | | | | | 175 | | | | | 180 | | |

| | | | | | | | | | | | | | | | | |
|---|---|---|---|---|---|---|---|---|---|---|---|---|---|---|---|---|
| TGT | AAA | GAT | GAT | ATA | ATT | AAA | CAT | TGT | AAG | TCT | TCT | ATA | GGT | ATG | TTT | 10152 |
| Cys | Lys | Asp | Asp | Ile | Ile | Lys | His | Cys | Lys | Ser | Ser | Ile | Gly | Met | Phe | |
| | | | 185 | | | | | 190 | | | | | 195 | | | |

| | | | | | | | | | | | | | | | | |
|---|---|---|---|---|---|---|---|---|---|---|---|---|---|---|---|---|
| GCT | ATA | TTA | TCA | TCG | AAA | ATA | ATC | GAC | GTA | GAT | TTT | GAT | GTT | ATA | TTC | 10200 |
| Ala | Ile | Leu | Ser | Ser | Lys | Ile | Ile | Asp | Val | Asp | Phe | Asp | Val | Ile | Phe | |
| | | | 200 | | | | | 205 | | | | | 210 | | | |

| | | | | | | | | | | | | | | | | |
|---|---|---|---|---|---|---|---|---|---|---|---|---|---|---|---|---|
| TTT | TCA | CAA | ATA | AGT | ATA | AGA | TAT | AGA | CTA | ATA | TTC | AAA | AAA | TAT | CTC | 10248 |
| Phe | Ser | Gln | Ile | Ser | Ile | Arg | Tyr | Arg | Leu | Ile | Phe | Lys | Lys | Tyr | Leu | |
| | | 215 | | | | | 220 | | | | | 225 | | | | |

| | | | | | | | | | | | | | | | | |
|---|---|---|---|---|---|---|---|---|---|---|---|---|---|---|---|---|
| ATA | CAA | TCA | TTA | TAC | TTA | CAA | TAATAATTGT | TTTTTTTTG | AAAAATAATC | | | | | | | 10299 |
| Ile | Gln | Ser | Leu | Tyr | Leu | Gln | | | | | | | | | | |
| 230 | | | | | 235 | | | | | | | | | | | |

| | | | | | | | | | | | | | |
|---|---|---|---|---|---|---|---|---|---|---|---|---|---|
| CTAAATCTAT | CATAAC | ATG | AAT | TCA | TTA | TTA | TTA | CGA | TTA | CAT | GAT | TTT | 10348 |
| | | Met | Asn | Ser | Leu | Leu | Leu | Arg | Leu | His | Asp | Phe | |
| | | 1 | | | 5 | | | | | 10 | | | |

| | | | | | | | | | | | | | | | | |
|---|---|---|---|---|---|---|---|---|---|---|---|---|---|---|---|---|
| TTT | AAA | CAT | GGA | ATT | ATG | TGT | GAT | ATA | AAA | ATA | GTA | TCC | ATA | GAG | AAT | 10396 |
| Phe | Lys | His | Gly | Ile | Met | Cys | Asp | Ile | Lys | Ile | Val | Ser | Ile | Glu | Asn | |
| | | | 15 | | | | | 20 | | | | | 25 | | | |

| | | | | | | | | | | | | | | | | |
|---|---|---|---|---|---|---|---|---|---|---|---|---|---|---|---|---|
| AAT | AAA | ACC | ATT | AGC | GCA | CAT | AGG | TTA | ATA | TTA | TCT | ATG | TAC | TCT | AAG | 10444 |
| Asn | Lys | Thr | Ile | Ser | Ala | His | Arg | Leu | Ile | Leu | Ser | Met | Tyr | Ser | Lys | |
| | | 30 | | | | | 35 | | | | | 40 | | | | |

| | | | | | | | | | | | | | | | | |
|---|---|---|---|---|---|---|---|---|---|---|---|---|---|---|---|---|
| TAC | TTT | TAT | AAT | ATA | TTT | AAT | TCA | GAT | TTT | ATT | GAT | AAA | AAT | AAT | GAT | 10492 |
| Tyr | Phe | Tyr | Asn | Ile | Phe | Asn | Ser | Asp | Phe | Ile | Asp | Lys | Asn | Asn | Asp | |

-continued

```
                   45                            50                              55
GAA  ATC  TAT  ATA  TGC  GCC  GAT  TAT  GAT  ATA  TTG  TAT  ATT  ATA  TTG  GAA            10540
Glu  Ile  Tyr  Ile  Cys  Ala  Asp  Tyr  Asp  Ile  Leu  Tyr  Ile  Ile  Leu  Glu
60              65                       70                            75

TTT  ATG  TAC  ACC  GGT  AAT  ATA  GTA  CTA  ACA  AAG  GAT  AAT  ATA  GAA  TTA            10588
Phe  Met  Tyr  Thr  Gly  Asn  Ile  Val  Leu  Thr  Lys  Asp  Asn  Ile  Glu  Leu
                    80                       85                            90

GTA  ATA  CAA  GTC  TGT  GAT  TAT  CTA  TGT  ATA  GAT  TCT  TTA  ATA  AAA  ATA            10636
Val  Ile  Gln  Val  Cys  Asp  Tyr  Leu  Cys  Ile  Asp  Ser  Leu  Ile  Lys  Ile
                95                      100                           105

TGT  GAA  GAA  TAT  ATA  TGC  GGT  ATA  ATA  GAT  GAA  ACA  AAT  TGT  ATA  CAT            10684
Cys  Glu  Glu  Tyr  Ile  Cys  Gly  Ile  Ile  Asp  Glu  Thr  Asn  Cys  Ile  His
     110                      115                          120

CTC  TTA  AAC  TTT  TCA  GAT  ACT  TAC  AAT  CTA  CAA  CGA  TTA  CGT  GAA  ATG            10732
Leu  Leu  Asn  Phe  Ser  Asp  Thr  Tyr  Asn  Leu  Gln  Arg  Leu  Arg  Glu  Met
     125                      130                          135

TCA  AAA  TGG  TAT  TTA  CCA  AAA  ATA  ATA  AAT  AAT  AAC  AAA  CTG  GTA  GTA            10780
Ser  Lys  Trp  Tyr  Leu  Pro  Lys  Ile  Ile  Asn  Asn  Asn  Lys  Leu  Val  Val
140                      145                           150                      155

GAA  TTA  GAT  ATA  GAT  GAT  ATG  ATA  TTA  ATT  ATA  AAA  GAA  ATT  AAA  TAC            10828
Glu  Leu  Asp  Ile  Asp  Asp  Met  Ile  Leu  Ile  Ile  Lys  Glu  Ile  Lys  Tyr
                         160                      165                          170

ATT  GCA  TGT  GAA  TAT  ATA  GTT  AAA  AAA  ATA  ATA  TTA  AAT  TGG  ATC  GTT            10876
Ile  Ala  Cys  Glu  Tyr  Ile  Val  Lys  Lys  Ile  Ile  Leu  Asn  Trp  Ile  Val
               175                      180                           185

CAT  AAA  GAT  GAA  CGA  ATT  ATT  TAT  ACT  AAA  AAA  TTA  ATG  AAA  CAT  ATC            10924
His  Lys  Asp  Glu  Arg  Ile  Ile  Tyr  Thr  Lys  Lys  Leu  Met  Lys  His  Ile
          190                      195                           200

AAT  GAT  CAA  GAC  CAT  TAT  ACA  TCC  TTA  TCG  GAT  ATT  GAA  TTG  TAC  AAT            10972
Asn  Asp  Gln  Asp  His  Tyr  Thr  Ser  Leu  Ser  Asp  Ile  Glu  Leu  Tyr  Asn
     205                      210                           215

AAT  ATA  CGG  GAA  CGA  ATA  TAT  GAT  AAC  AAA  GAA  CAC  GAT  GTA  GAT  ATA            11020
Asn  Ile  Arg  Glu  Arg  Ile  Tyr  Asp  Asn  Lys  Glu  His  Asp  Val  Asp  Ile
220                      225                           230                      235

TCA  CAT  AAC  TTT  ATA  ATA  ATG  GTA  GGA  GGA  AAA  AAG  ATA  TTT  AAT  ATA            11068
Ser  His  Asn  Phe  Ile  Ile  Met  Val  Gly  Gly  Lys  Lys  Ile  Phe  Asn  Ile
                         240                      245                          250

ACC  GCA  TTC  AAT  CCG  TTA  TCG  AAT  AAA  AAA  CAT  ATT  ATA  GAC  AGA  TAC            11116
Thr  Ala  Phe  Asn  Pro  Leu  Ser  Asn  Lys  Lys  His  Ile  Ile  Asp  Arg  Tyr
               255                      260                           265

GAT  GAT  ATG  TTT  GGT  TGT  AAA  ACT  CAT  TTT  AGT  GTT  GTA  TAC  TTA  AAT            11164
Asp  Asp  Met  Phe  Gly  Cys  Lys  Thr  His  Phe  Ser  Val  Val  Tyr  Leu  Asn
          270                      275                           280

AGT  ATA  CTA  TAT  ATT  ATC  GGT  GGA  AAG  AAA  CGA  GGA  TAT  TTC  ACT  AAA            11212
Ser  Ile  Leu  Tyr  Ile  Ile  Gly  Gly  Lys  Lys  Arg  Gly  Tyr  Phe  Thr  Lys
     285                      290                           295

GAG  GTG  TTG  TCA  TAT  AAT  ATA  AAA  AAC  AAA  TTA  TGG  TGT  TAC  GAA  CCA            11260
Glu  Val  Leu  Ser  Tyr  Asn  Ile  Lys  Asn  Lys  Leu  Trp  Cys  Tyr  Glu  Pro
300                      305                           310                      315

GAA  TTA  AAT  TAT  TTT  AGA  TAC  GAT  ACA  TCT  GTA  TGT  GTA  TCA  AAT  GGG            11308
Glu  Leu  Asn  Tyr  Phe  Arg  Tyr  Asp  Thr  Ser  Val  Cys  Val  Ser  Asn  Gly
                         320                      325                          330

ATG  ATA  TAT  TCA  ATT  GGT  GGA  AAA  GAT  ACA  AAT  GGA  TAT  ATG  ACA  AAC            11356
Met  Ile  Tyr  Ser  Ile  Gly  Gly  Lys  Asp  Thr  Asn  Gly  Tyr  Met  Thr  Asn
               335                      340                           345

ATC  GTA  GAA  TTT  TGG  AAA  CCT  GAA  TGG  AAA  TCA  TGG  TAT  GAT  GGT  CAA            11404
Ile  Val  Glu  Phe  Trp  Lys  Pro  Glu  Trp  Lys  Ser  Trp  Tyr  Asp  Gly  Gln
          350                      355                           360

CAT  TTG  TGT  TAT  CCT  AGA  TGT  TAT  ATG  TCG  TTG  GTA  GAC  TAT  AAT  AAT            11452
His  Leu  Cys  Tyr  Pro  Arg  Cys  Tyr  Met  Ser  Leu  Val  Asp  Tyr  Asn  Asn
```

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
|     |     | 365 |     |     |     |     | 370 |     |     |     |     | 375 |     |     |     |       |
| GAA | GTA | TAT | ACA | ATA | GGT | GGA | TTA | AAA | ACA | TCA | ATA | ACG | GAT | GAA | TTT | 11500 |
| Glu | Val | Tyr | Thr | Ile | Gly | Gly | Leu | Lys | Thr | Ser | Ile | Thr | Asp | Glu | Phe |       |
| 380 |     |     |     |     | 385 |     |     |     |     | 390 |     |     |     |     | 395 |       |
| AAT | ATA | GAA | ATG | ATT | GTA | TCA | GAC | GAT | GCC | GTA | GAG | AAA | CTG | ACC | GAT | 11548 |
| Asn | Ile | Glu | Met | Ile | Val | Ser | Asp | Asp | Ala | Val | Glu | Lys | Leu | Thr | Asp |       |
|     |     |     |     | 400 |     |     |     |     | 405 |     |     |     |     | 410 |     |       |
| CAT | TCA | TGG | ATG | AAG | TTA | AAA | CAA | TTT | CCC | ATA | GCA | AAG | AGT | GGT | ATA | 11596 |
| His | Ser | Trp | Met | Lys | Leu | Lys | Gln | Phe | Pro | Ile | Ala | Lys | Ser | Gly | Ile |       |
|     |     |     | 415 |     |     |     |     | 420 |     |     |     |     | 425 |     |     |       |
| TCA | TCC | ATA | GTA | TAT | AAC | GAT | TTT | ATA | TAC | TGT | ATA | GGT | GGT | CGT | ATA | 11644 |
| Ser | Ser | Ile | Val | Tyr | Asn | Asp | Phe | Ile | Tyr | Cys | Ile | Gly | Gly | Arg | Ile |       |
|     |     | 430 |     |     |     |     | 435 |     |     |     |     | 440 |     |     |     |       |
| GAT | ACA | CCA | CAT | ATA | AGT | ATA | GAA | CAC | ACT | AAC | GAT | GTT | TAT | ATA | TAT | 11692 |
| Asp | Thr | Pro | His | Ile | Ser | Ile | Glu | His | Thr | Asn | Asp | Val | Tyr | Ile | Tyr |       |
|     |     | 445 |     |     |     |     | 450 |     |     |     |     | 455 |     |     |     |       |
| TCT | TCA | AGA | GAT | GAT | TGT | TGG | AAA | TAT | TTA | TCA | AAT | ACA | AAT | GTA | AAA | 11740 |
| Ser | Ser | Arg | Asp | Asp | Cys | Trp | Lys | Tyr | Leu | Ser | Asn | Thr | Asn | Val | Lys |       |
| 460 |     |     |     |     | 465 |     |     |     |     | 470 |     |     |     |     | 475 |       |
| AGA | TCA | TTT | TGT | CTA | TCG | TGT | GTT | TTT | AAT | AAT | GAA | TTA | TAT | ATA | ATA | 11788 |
| Arg | Ser | Phe | Cys | Leu | Ser | Cys | Val | Phe | Asn | Asn | Glu | Leu | Tyr | Ile | Ile |       |
|     |     |     |     | 480 |     |     |     |     | 485 |     |     |     |     | 490 |     |       |
| GGT | GGA | TAT | AAT | ACA | AAC | AGT | GTA | GAA | AAG | TAC | AAT | AAA | TTA | AAA | AAT | 11836 |
| Gly | Gly | Tyr | Asn | Thr | Asn | Ser | Val | Glu | Lys | Tyr | Asn | Lys | Leu | Lys | Asn |       |
|     |     |     | 495 |     |     |     |     | 500 |     |     |     |     | 505 |     |     |       |
| ACA | TGG | AAG | CGT | TTA | AAC | GAT | ATT | CCT | AAG | TTT | GAA | GAA | TGT | GTT | AAT | 11884 |
| Thr | Trp | Lys | Arg | Leu | Asn | Asp | Ile | Pro | Lys | Phe | Glu | Glu | Cys | Val | Asn |       |
|     |     | 510 |     |     |     |     | 515 |     |     |     |     | 520 |     |     |     |       |
| GAA | GCA | TCG | GCA | ATA | TAT | TTG | TAGTATCCCT | | TATAGCGTTC | | AAAAGAAACA | | | | | 11935 |
| Glu | Ala | Ser | Ala | Ile | Tyr | Leu |     |     |     |     |     |     |     |     |     |       |
| 525 |     |     |     |     |     | 530 |     |     |     |     |     |     |     |     |     |       |

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
| AATCCATAAC | | AGACATCTAT | | ATTCTTAATC | | TATCT | | ATG | TCA | GAT | TGT | ATA | TTC | | | 11988 |
|     |     |     |     |     |     |     |     | Met | Ser | Asp | Cys | Ile | Phe |     |     |       |
|     |     |     |     |     |     |     |     | 1   |     |     |     | 5   |     |     |     |       |
| GTA | TTT | CAG | ATT | CCG | TTC | ATT | GTG | TAT | AGT | AAA | CTC | GAT | CAA | TGG | ATT | 12036 |
| Val | Phe | Gln | Ile | Pro | Phe | Ile | Val | Tyr | Ser | Lys | Leu | Asp | Gln | Trp | Ile |       |
|     |     |     | 10  |     |     |     |     | 15  |     |     |     |     | 20  |     |     |       |
| TTT | GGG | AAT | ATA | CTA | TGT | AAA | ATA | ATG | TCC | GTA | TTA | TAC | TAC | GTA | GGA | 12084 |
| Phe | Gly | Asn | Ile | Leu | Cys | Lys | Ile | Met | Ser | Val | Leu | Tyr | Tyr | Val | Gly |       |
|     |     | 25  |     |     |     |     | 30  |     |     |     |     | 35  |     |     |     |       |
| TTC | TTT | AGT | AAT | ATG | TTT | ATA | ATA | ACA | CTT | ATG | AGT | ATA | GAT | AGA | TAT | 12132 |
| Phe | Phe | Ser | Asn | Met | Phe | Ile | Ile | Thr | Leu | Met | Ser | Ile | Asp | Arg | Tyr |       |
|     |     | 40  |     |     |     | 45  |     |     |     |     | 50  |     |     |     |     |       |
| TTT | GCG | ATC | GTT | CAT | CCT | ATA | AAG | CGA | CAA | CCG | TAT | AGG | ACG | AAA | CGT | 12180 |
| Phe | Ala | Ile | Val | His | Pro | Ile | Lys | Arg | Gln | Pro | Tyr | Arg | Thr | Lys | Arg |       |
| 55  |     |     |     |     | 60  |     |     |     |     | 65  |     |     |     |     | 70  |       |
| ATA | GGT | ATC | CTT | ATG | TGC | TGT | TCC | GCT | TGG | TTA | TTA | TCC | TTG | ATA | TTA | 12228 |
| Ile | Gly | Ile | Leu | Met | Cys | Cys | Ser | Ala | Trp | Leu | Leu | Ser | Leu | Ile | Leu |       |
|     |     |     |     | 75  |     |     |     |     | 80  |     |     |     |     | 85  |     |       |
| TCT | AGT | CCC | GTA | TCT | AAA | CTA | TAC | GAG | AAT | ATT | CCT | CAT | ATG | TCT | AAA | 12276 |
| Ser | Ser | Pro | Val | Ser | Lys | Leu | Tyr | Glu | Asn | Ile | Pro | His | Met | Ser | Lys |       |
|     |     |     | 90  |     |     |     |     | 95  |     |     |     |     | 100 |     |     |       |
| GAT | ATA | TAC | CAA | TGT | ACT | CTG | ACG | AAC | GAG | AAT | GAC | TCC | ATA | ATC | GCA | 12324 |
| Asp | Ile | Tyr | Gln | Cys | Thr | Leu | Thr | Asn | Glu | Asn | Asp | Ser | Ile | Ile | Ala |       |
|     |     | 105 |     |     |     |     | 110 |     |     |     |     | 115 |     |     |     |       |
| TTC | ATA | AAA | AGA | CTG | ATG | CAA | ATA | GAG | ATC | ACT | ATA | TTG | GGA | TTC | CTG | 12372 |
| Phe | Ile | Lys | Arg | Leu | Met | Gln | Ile | Glu | Ile | Thr | Ile | Leu | Gly | Phe | Leu |       |
|     |     | 120 |     |     |     |     | 125 |     |     |     |     | 130 |     |     |     |       |
| ATA | CCT | ATA | ATC | ATA | TTC | GTA | TAT | TGC | TAT | TAT | AGA | ATT | TTT | TCT | ACA | 12420 |

| | | | | | | | | | | | | | | | | |
|---|---|---|---|---|---|---|---|---|---|---|---|---|---|---|---|---|
| Ile | Pro | Ile | Ile | Ile | Phe | Val | Tyr | Cys | Tyr | Tyr | Arg | Ile | Phe | Ser | Thr | |
| 135 | | | | 140 | | | | | 145 | | | | | | 150 | |

```
GTG GTT AGA TTA AGA AAT AGA CGA AAG TAT AAA TCT ATA AAA ATT GTA      12468
Val Val Arg Leu Arg Asn Arg Arg Lys Tyr Lys Ser Ile Lys Ile Val
            155                 160                 165

TTA ATG ATT GTT GTA TGT TCT CTA ATA TGT TGG ATT CCG CTC TAT ATC      12516
Leu Met Ile Val Val Cys Ser Leu Ile Cys Trp Ile Pro Leu Tyr Ile
            170                 175                 180

GTT CTA ATG ATA GCG ACG ATT GTT AGC TTA TAT ACA TCT AAT ATA TTT      12564
Val Leu Met Ile Ala Thr Ile Val Ser Leu Tyr Thr Ser Asn Ile Phe
            185                 190                 195

AGA CAT CTG TGC CTC TAT CTA AAC CTG GCC TAT GCG ATC ACC TTT TCG      12612
Arg His Leu Cys Leu Tyr Leu Asn Leu Ala Tyr Ala Ile Thr Phe Ser
    200                 205                 210

GAG ACT ATC TCG TTA GCG CGT TGT TGT ATA AAT CCA ATA ATA TAT ACA      12660
Glu Thr Ile Ser Leu Ala Arg Cys Cys Ile Asn Pro Ile Ile Tyr Thr
215                 220                 225                 230

CTG ATA GGT GAA CAT GTT CGA TCT CGT ATA TCT AGC ATA TGT TCG TGT      12708
Leu Ile Gly Glu His Val Arg Ser Arg Ile Ser Ser Ile Cys Ser Cys
                235                 240                 245

ATA TAT AGA GAC AAT AGG ATT AGG AAA AAA CTC TTT TCA CGA AAA TCT      12756
Ile Tyr Arg Asp Asn Arg Ile Arg Lys Lys Leu Phe Ser Arg Lys Ser
            250                 255                 260

TCT AGC AGT AGC AAT ATT ATT TAGTTGTTAT TTTCTTACAA AACACAAGTT         12807
Ser Ser Ser Ser Asn Ile Ile
        265             270

ATAAATAATC ATTACGTAAT C ATG CTA TCG TAT ATT ATT AAT CCT TTG CTA      12858
                       Met Leu Ser Tyr Ile Ile Asn Pro Leu Leu
                        1               5                   10

AGT ATT GTA TAC TTT ATA TTA GGA AAT GTA TCT AAG CTG CTT ACA TAT      12906
Ser Ile Val Tyr Phe Ile Leu Gly Asn Val Ser Lys Leu Leu Thr Tyr
                15                  20                  25

ATA CTT ATG AAA ATA ATG ATT TTT TTA CTT CGT GCG GTG AAT CCA TAC      12954
Ile Leu Met Lys Ile Met Ile Phe Leu Leu Arg Ala Val Asn Pro Tyr
            30                  35                  40

TCT CTG ATA TCT AAC AGA GGT TGG CTG TCG CTG GAT AGT ATA AAT CCC      13002
Ser Leu Ile Ser Asn Arg Gly Trp Leu Ser Leu Asp Ser Ile Asn Pro
        45                  50                  55

TTT AAA AAG GAA AAG CGT AGG GAG TCT TTT CTA TCT AGT CTA AAT CCG      13050
Phe Lys Lys Glu Lys Arg Arg Glu Ser Phe Leu Ser Ser Leu Asn Pro
    60                  65                  70

TTT AGA AAA GAG GAA ACA AAG AAA AAA GAA GGT TTC TTT TCT GGT TGG      13098
Phe Arg Lys Glu Glu Thr Lys Lys Lys Glu Gly Phe Phe Ser Gly Trp
75                  80                  85                  90

TTC GGA TAATCTCTTT TATAATTGAA ATAATATTCC AAAAATAAAT CATA ATG ATT     13154
Phe Gly                                                    Met Ile
                                                            1

ACT AAA GCG ATT GTG ATA TTG TCT ATT ATT ACA GCA TAT GTA GAT GCT      13202
Thr Lys Ala Ile Val Ile Leu Ser Ile Ile Thr Ala Tyr Val Asp Ala
        5                   10                  15

TCC GCA TTC TTA GTA TAC AAT TAT ACA TAT ACT TTA CAA GAT GAT AAT      13250
Ser Ala Phe Leu Val Tyr Asn Tyr Thr Tyr Thr Leu Gln Asp Asp Asn
    20                  25                  30

CAT CGA TAT GAC TTC GAA GTC ACC GAT TAT TTT AAT GAT ATA CTA ATA      13298
His Arg Tyr Asp Phe Glu Val Thr Asp Tyr Phe Asn Asp Ile Leu Ile
35                  40                  45                  50

AAA CGT TTA AAA CTA AAT AGC GAG ACA GGA AGA CCA GAA TTA AGA AAT      13346
Lys Arg Leu Lys Leu Asn Ser Glu Thr Gly Arg Pro Glu Leu Arg Asn
                55                  60                  65
```

| | | | | | | | | | | | | | | | | |
|---|---|---|---|---|---|---|---|---|---|---|---|---|---|---|---|---|
| GAA | CCA | CCA | ACA | TGG | TTT | AAT | GAG | ACT | AAG | ATT | AGA | TAT | TAT | CCG | AAA | 13394 |
| Glu | Pro | Pro | Thr | Trp | Phe | Asn | Glu | Thr | Lys | Ile | Arg | Tyr | Tyr | Pro | Lys | |
| | | | 70 | | | | | 75 | | | | | 80 | | | |
| AAT | AAT | TAT | AAT | TTT | ATG | TTC | TGG | CTA | AAT | AGA | ATG | AGT | GAA | ACG | CTA | 13442 |
| Asn | Asn | Tyr | Asn | Phe | Met | Phe | Trp | Leu | Asn | Arg | Met | Ser | Glu | Thr | Leu | |
| | | 85 | | | | | 90 | | | | | 95 | | | | |
| GAT | GAG | ATA | AAT | AAA | CTT | CCA | GAA | ACG | AGT | AAT | CCT | TAC | AAG | ACT | ATG | 13490 |
| Asp | Glu | Ile | Asn | Lys | Leu | Pro | Glu | Thr | Ser | Asn | Pro | Tyr | Lys | Thr | Met | |
| | 100 | | | | | 105 | | | | | 110 | | | | | |
| TCC | TTG | ACA | ATT | GGA | TGT | ACT | GAT | CTA | AGA | CAA | CTT | CAA | GTA | AAT | TTC | 13538 |
| Ser | Leu | Thr | Ile | Gly | Cys | Thr | Asp | Leu | Arg | Gln | Leu | Gln | Val | Asn | Phe | |
| 115 | | | | | 120 | | | | | 125 | | | | | 130 | |
| GGT | TAT | GTT | ACT | GTA | GGT | GGT | AAT | ATA | TGG | ACA | CGA | TTC | GAC | CCC | AAG | 13586 |
| Gly | Tyr | Val | Thr | Val | Gly | Gly | Asn | Ile | Trp | Thr | Arg | Phe | Asp | Pro | Lys | |
| | | | | 135 | | | | | 140 | | | | | 145 | | |
| AAT | AAA | CGC | TTT | AGT | AAA | GTT | AGA | TCA | CGT | ACA | TTT | CCA | AAG | GTA | GGA | 13634 |
| Asn | Lys | Arg | Phe | Ser | Lys | Val | Arg | Ser | Arg | Thr | Phe | Pro | Lys | Val | Gly | |
| | | | 150 | | | | | 155 | | | | | 160 | | | |
| ATG | TTA | ACT | GTT | AAA | TCA | CAA | CAC | TGG | GAA | CGT | GTT | ATG | GAA | CAT | CTT | 13682 |
| Met | Leu | Thr | Val | Lys | Ser | Gln | His | Trp | Glu | Arg | Val | Met | Glu | His | Leu | |
| | | 165 | | | | | 170 | | | | | 175 | | | | |
| GGA | TCA | ATG | GTA | ACA | TTA | ACA | TGT | CCG | TTT | ACA | GCG | GAT | GAT | TAT | TAT | 13730 |
| Gly | Ser | Met | Val | Thr | Leu | Thr | Cys | Pro | Phe | Thr | Ala | Asp | Asp | Tyr | Tyr | |
| | 180 | | | | | 185 | | | | | 190 | | | | | |
| AAA | ATT | TCT | AAG | GGA | TAT | ATA | GAT | AAG | CCA | GTT | AAG | CCT | ACT | GTT | ACA | 13778 |
| Lys | Ile | Ser | Lys | Gly | Tyr | Ile | Asp | Lys | Pro | Val | Lys | Pro | Thr | Val | Thr | |
| 195 | | | | | 200 | | | | | 205 | | | | | 210 | |
| GTT | ACA | GGA | ATT | GAA | AGA | GGA | GAT | AAT | ACT | ACA | TTG | ATA | TGC | ACA | TTT | 13826 |
| Val | Thr | Gly | Ile | Glu | Arg | Gly | Asp | Asn | Thr | Thr | Leu | Ile | Cys | Thr | Phe | |
| | | | | 215 | | | | | 220 | | | | | 225 | | |
| GAT | AAT | CAT | TAT | CCG | TCG | TCG | GTC | GCT | GTT | AAA | TGG | TAT | AAC | ATC | GAG | 13874 |
| Asp | Asn | His | Tyr | Pro | Ser | Ser | Val | Ala | Val | Lys | Trp | Tyr | Asn | Ile | Glu | |
| | | | 230 | | | | | 235 | | | | | 240 | | | |
| GAC | TTT | GCT | CCG | GAC | TAT | CGT | TAT | GAT | CCG | TAC | GTA | AAT | GAA | TTG | CTT | 13922 |
| Asp | Phe | Ala | Pro | Asp | Tyr | Arg | Tyr | Asp | Pro | Tyr | Val | Asn | Glu | Leu | Leu | |
| | | 245 | | | | | 250 | | | | | 255 | | | | |
| CCT | GAT | ACG | GAC | TAT | CTA | CCG | GGT | GAA | CCA | GGA | TAT | CCG | ACT | ATA | ACT | 13970 |
| Pro | Asp | Thr | Asp | Tyr | Leu | Pro | Gly | Glu | Pro | Gly | Tyr | Pro | Thr | Ile | Thr | |
| | 260 | | | | | 265 | | | | | 270 | | | | | |
| AGG | AGA | TTA | GGT | GAT | AAA | TAT | TTA | TTT | ACA | TCA | TCA | CCT | AGG | GTT | ATG | 14018 |
| Arg | Arg | Leu | Gly | Asp | Lys | Tyr | Leu | Phe | Thr | Ser | Ser | Pro | Arg | Val | Met | |
| 275 | | | | | 280 | | | | | 285 | | | | | 290 | |
| GTA | CCA | ACT | ATC | ATG | TCT | AAT | AGA | ATA | GCA | TGT | GTT | GGA | TTT | CAT | AGT | 14066 |
| Val | Pro | Thr | Ile | Met | Ser | Asn | Arg | Ile | Ala | Cys | Val | Gly | Phe | His | Ser | |
| | | | | 295 | | | | | 300 | | | | | 305 | | |
| ACG | TTA | GAA | CCA | AGC | ATA | TAT | AGA | TGT | GTA | AAC | TGC | TCG | GGA | CCT | GAG | 14114 |
| Thr | Leu | Glu | Pro | Ser | Ile | Tyr | Arg | Cys | Val | Asn | Cys | Ser | Gly | Pro | Glu | |
| | | | 310 | | | | | 315 | | | | | 320 | | | |
| CCT | GTT | TTA | CAA | TAC | CAG | GGA | GAT | AGA | AGG | AAT | GAC | TTG | GAG | GAT | GAG | 14162 |
| Pro | Val | Leu | Gln | Tyr | Gln | Gly | Asp | Arg | Arg | Asn | Asp | Leu | Glu | Asp | Glu | |
| | | 325 | | | | | 330 | | | | | 335 | | | | |
| GAG | GAT | TAAAGCTT | | | | | | | | | | | | | | 14176 |
| Glu | Asp | | | | | | | | | | | | | | | |
| 340 | | | | | | | | | | | | | | | | |

( 2 ) INFORMATION FOR SEQ ID NO:15:

( i ) SEQUENCE CHARACTERISTICS:
( A ) LENGTH: 440 amino acids
( B ) TYPE: amino acid
( D ) TOPOLOGY: linear ( i i ) MOLECULE TYPE: protein ( x i ) SEQUENCE DESCRIPTION: SEQ ID NO:15:

| Met | Lys | Glu | Ile | Asn | Ser | Leu | Glu | Cys | Gln | Trp | Glu | Ser | Ile | Asp | Asp |
| 1 | | | | 5 | | | | | 10 | | | | | 15 | |

| Asn | Asn | Asp | Thr | Thr | Ile | Leu | Gly | Asp | Asp | Ile | Tyr | Phe | Asp | Tyr | Ile |
| | | | 20 | | | | | 25 | | | | | 30 | | |

| Ile | Ser | Gln | Leu | Asp | Ile | His | Gln | Asn | Trp | Ser | Pro | Asp | Ile | Arg | Leu |
| | | 35 | | | | | 40 | | | | | 45 | | | |

| Ile | Arg | Tyr | Phe | Arg | Lys | Phe | Asn | Lys | Glu | Ser | Phe | Asp | Lys | Ile | Ser |
| | 50 | | | | | 55 | | | | | 60 | | | | |

| Asp | Thr | Glu | Tyr | Ile | Asn | Pro | Ser | Phe | Phe | Gln | Arg | Asp | Lys | Arg |
| 65 | | | | | 70 | | | | | 75 | | | | 80 |

| Phe | Tyr | Pro | Leu | Asn | Asp | Asp | Phe | Tyr | His | Ile | Ser | Thr | Gly | Gly | Tyr |
| | | | | 85 | | | | | 90 | | | | | 95 | |

| Gly | Ile | Val | Phe | Lys | Met | Asp | Lys | Tyr | Val | Val | Lys | Phe | Val | Tyr | Glu |
| | | | 100 | | | | | 105 | | | | | 110 | | |

| Pro | Asn | Lys | Gln | Tyr | Ser | Pro | Ile | Asp | Thr | Thr | Ala | Glu | Tyr | Thr | Ile |
| | | 115 | | | | | 120 | | | | | 125 | | | |

| Pro | Lys | Phe | Leu | Tyr | Asn | Asn | Leu | Lys | Gly | Asp | Glu | Lys | Lys | Leu | Ile |
| | 130 | | | | | 135 | | | | | 140 | | | | |

| Val | Cys | Ala | Trp | Ala | Met | Gly | Leu | Asn | Tyr | Lys | Leu | Thr | Phe | Leu | His |
| 145 | | | | | 150 | | | | | 155 | | | | | 160 |

| Arg | Leu | Tyr | Lys | Arg | Val | Leu | Tyr | Met | Leu | Leu | Ile | Ile | Gln | Thr |
| | | | | 165 | | | | | 170 | | | | | 175 |

| Ile | Asp | Asn | Gln | Arg | Leu | Asn | Ile | His | His | Phe | Ser | His | Lys | Tyr | Phe |
| | | | 180 | | | | | 185 | | | | | 190 | | |

| Leu | Lys | Ser | Phe | Asn | Glu | Lys | Lys | Ser | Asp | Ile | Lys | Phe | Val | Lys | Leu |
| | | 195 | | | | | 200 | | | | | 205 | | | |

| Leu | Ser | Tyr | Phe | Tyr | Pro | Ile | Val | Val | Gln | Ser | Asn | Ile | Asn | Val | Ile |
| | 210 | | | | | 215 | | | | | 220 | | | | |

| Asn | Tyr | Phe | Thr | His | Met | Phe | His | Phe | Phe | Glu | His | Glu | Lys | Arg | Ala |
| 225 | | | | | 230 | | | | | 235 | | | | | 240 |

| Asn | Tyr | Leu | Tyr | Asp | Arg | Gly | Asn | Ile | Ile | Ile | Phe | Pro | Leu | Ala | Arg |
| | | | | 245 | | | | | 250 | | | | | 255 | |

| Phe | Ser | Ser | Asp | Lys | Val | Thr | Glu | Gln | Met | Ala | Ile | Glu | Leu | Gly | Phe |
| | | | 260 | | | | | 265 | | | | | 270 | | |

| Lys | Ser | Ile | Val | Gln | Tyr | Val | Lys | Phe | Ile | Phe | Leu | Gln | Ile | Ser | Leu |
| | | 275 | | | | | 280 | | | | | 285 | | | |

| Leu | Tyr | Ile | Lys | Ile | Tyr | Glu | Leu | Pro | Cys | Cys | Asp | Asn | Phe | Leu | His |
| | 290 | | | | | 295 | | | | | 300 | | | | |

| Val | Asp | Leu | Lys | Pro | Asp | Asn | Ile | Leu | Ile | Phe | Asn | Ser | Asp | Cys | Pro |
| 305 | | | | | 310 | | | | | 315 | | | | | 320 |

| Ile | Thr | Ile | Lys | Phe | Lys | Lys | Tyr | Thr | Tyr | Val | Phe | Asn | Glu | Pro | Ile |
| | | | | 325 | | | | | 330 | | | | | 335 | |

| Lys | Ala | Cys | Leu | Asn | Asp | Phe | Asp | Phe | Ser | Gln | Val | Ala | Asn | Ile | Leu |
| | | | 340 | | | | | 345 | | | | | 350 | | |

| Asn | Lys | Lys | Ile | Lys | Asn | Ser | Leu | Lys | Ile | Glu | His | Asn | Trp | Tyr | Tyr |
| | | 355 | | | | | 360 | | | | | 365 | | | |

| Asp | Phe | His | Phe | Phe | Ile | His | Thr | Leu | Leu | Arg | Thr | Tyr | Pro | Glu | Ile |
| | | 370 | | | | | 375 | | | | | 380 | | | |

| Glu | Ser | Asp | Lys | Glu | Phe | Ser | Asp | Ser | Leu | Glu | Asp | Phe | Ile | Met | Cys |
| 385 | | | | | 390 | | | | | 395 | | | | | 400 |

| Cys | Thr | Lys | Asn | Thr | Cys | Glu | Lys | Phe | Arg | Leu | Lys | Val | Ser | Ile | Leu |

```
                              405                     410                     415
His Pro Ile Ser Phe Leu Glu Asn Leu Ile Thr Lys Asn Ile Phe Ser
            420                     425                 430
Asn Trp Ile Asn Gly Glu Ser Cys
            435                 440
```

( 2 ) INFORMATION FOR SEQ ID NO:16:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met His Leu Lys Asn Glu Val Asn Asn Met Phe Val Phe Thr Leu
 1               5                  10                  15
Cys Ile Leu Leu Tyr Ser Ser Phe Cys Tyr Phe Phe Tyr Ile Glu Lys
                20                  25                  30
Ile Leu Gln His Thr Lys Pro Ile Tyr Thr Asn Tyr Gly Gln Leu Cys
             35                 40                  45
Ile Cys Lys Ile Asn Lys Tyr Lys Tyr Gly Tyr Ser Val Asn Ile Phe
         50                  55                  60
Tyr Arg Arg
65
```

( 2 ) INFORMATION FOR SEQ ID NO:17:

( i ) SEQUENCE CHARACTERISTICS:
        ( A ) LENGTH: 73 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Asn Asn Arg Lys Tyr Ser Ile Asn Asn Gly Phe Met Ser Tyr Leu
 1               5                  10                  15
Arg Lys Lys Phe Thr Thr Phe Leu Arg Lys Lys Ser Thr Tyr Arg Ile
                20                  25                  30
Lys Ser Asn Thr Asp Tyr Tyr Gln Glu Asn Glu Lys Leu Ile His Lys
             35                 40                  45
Asn Asn Ile Lys Ile Pro Tyr Lys Val Lys Val Ile Arg Lys Arg Cys
         50                  55                  60
Ser Ser Ser Asp Asp Asp Val Phe Ile
65                  70
```

( 2 ) INFORMATION FOR SEQ ID NO:18:

( i ) SEQUENCE CHARACTERISTICS:
        ( A ) LENGTH: 86 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met Asn Thr Thr Thr Ser Gln Ile Ile Ile Asp Asn Asp Met Ser Asn
 1               5                  10                  15
Glu Val Gly Thr Ile Met Val Ile Thr Leu Cys Leu Val Thr Ile Val
                20                  25                  30
```

```
Ile Thr Cys Tyr Leu Leu Leu Gln Leu Val Arg Trp Ser Phe Ile Val
         35                  40                  45

Asp Ile Phe Arg Gln Ile Arg Thr Arg Cys Leu Gln Trp Thr Ser Arg
         50                  55                  60

Arg Glu Phe Leu Gln Leu Asp Asn Met Tyr Tyr Thr Asn Asp Ser Ser
 65                  70                  75                  80

Val Gly Val Asn Thr Glu
                 85
```

(2) INFORMATION FOR SEQ ID NO:19:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:19:

```
Met Glu Pro Ile Leu Gln Glu Ser Asp Ser Arg Phe Val Ile Phe Pro
  1               5                  10                  15

Ile Lys Tyr His Asp Ile Trp Lys Met Tyr Lys Gln Ser Val Ala Ser
                 20                  25                  30

Phe Trp Thr Val Glu Glu Val Asp Leu Ser Lys Asp Leu Asp Asp Trp
         35                  40                  45

Asp Lys Leu Thr Lys Asp Glu Lys Tyr Phe Ile Lys His Ile Leu Ala
         50                  55                  60

Phe Phe Ala Ser Ser Asp Gly Ile Val Asn Glu Asn Leu Ala Glu Arg
 65                  70                  75                  80

Phe Tyr Val Asp Val Gln Cys Ser Glu Ala Arg Cys Phe Tyr Gly Phe
                 85                  90                  95

Gln Ile Ala Met Glu Asn Ile His Ser Glu Met Tyr Ser Leu Leu Ile
                100                 105                 110

Asp Thr Tyr Val Arg Asp Asn Ile Glu Lys Met His Leu Phe Asn Ala
             115                 120                 125

Ile Glu Thr Met Glu Cys Val Lys Lys Lys Ala Asp Trp Ala Arg Lys
         130                 135                 140

Trp Ile Ser Ser Asn Lys Val Tyr Gly Glu Arg Val Val Ala Phe Ala
145                 150                 155                 160

Ala Val Glu Gly Ile Phe Phe Ser Gly Ser Phe Ala Ala Ile Phe Trp
                 165                 170                 175

Ile Lys Lys Arg Gly Leu Met Pro Gly Leu Thr Phe Ser Asn Glu Leu
             180                 185                 190

Ile Ser Arg Asp Glu Gly Leu His Cys Asp Phe Ala Cys Leu Met Phe
         195                 200                 205

Lys His Leu Leu His Pro Pro Ser Lys Glu Val Ile Thr Ser Ile Ile
     210                 215                 220

Ile Asp Ala Val Asn Ile Glu Lys Glu Phe Leu Thr Val Ala Ile Pro
225                 230                 235                 240

Val Asp Leu Ile Gly Met Asn Cys Cys Leu Met Ser Gln Tyr Ile Glu
                 245                 250                 255

Phe Val Ala Asp Arg Leu Leu Thr Glu Leu Gly Cys Glu Lys Ser Gln
             260                 265                 270

Cys Ile
```

(2) INFORMATION FOR SEQ ID NO:20:

( i ) SEQUENCE CHARACTERISTICS:
   ( A ) LENGTH: 500 amino acids
   ( B ) TYPE: amino acid
   ( D ) TOPOLOGY: linear ( i i ) MOLECULE TYPE: protein ( x i ) SEQUENCE DESCRIPTION: SEQ ID NO:20:

| Met | Ser | Lys | Gln | Glu | Thr | Tyr | Ile | Asp | Tyr | Asn | Tyr | Ile | Glu | Arg | Leu |
|---|---|---|---|---|---|---|---|---|---|---|---|---|---|---|---|
| 1 | | | | 5 | | | | | 10 | | | | | 15 | |

| Asn | Ala | Val | Asn | Leu | Asn | Arg | Ser | Tyr | Asp | Glu | Glu | Ile | Val | Phe | Ile |
| | | | 20 | | | | | 25 | | | | | 30 | | |

| Met | Thr | Val | Gly | Gly | Val | Val | Lys | Val | Lys | Lys | Glu | Leu | Leu | Val | Ser |
| | | | 35 | | | | 40 | | | | | 45 | | | |

| Val | Ser | Asn | Tyr | Phe | Lys | Leu | Ile | Thr | Lys | Asn | Gln | Ser | Asn | Glu | Ile |
| | 50 | | | | | 55 | | | | | 60 | | | | |

| Thr | Val | Ser | Phe | Gln | Tyr | Glu | Ser | Phe | Leu | Asp | Ile | Ile | Lys | Tyr | Ile |
| 65 | | | | | 70 | | | | | 75 | | | | | 80 |

| Glu | Thr | Gly | Ile | Val | Thr | Ile | Asp | Leu | Asp | Asn | Val | Glu | Asn | Ile | Phe |
| | | | | 85 | | | | | 90 | | | | | 95 | |

| Ser | Ile | Ser | Cys | Ser | Lys | Ala | Ile | Asp | Phe | Leu | Lys | Asn | Ser | Cys | Ile |
| | | | 100 | | | | | 105 | | | | | 110 | | |

| Asp | Phe | Met | Ser | Lys | His | Ile | Thr | Asp | Ser | Thr | Cys | Val | Lys | Ile | Tyr |
| | | | 115 | | | | | 120 | | | | | 125 | | |

| Lys | Ile | Gly | Phe | Ser | Asn | Gly | Cys | Phe | Ala | Val | Tyr | Asn | Asp | Ala | Ile |
| | 130 | | | | | 135 | | | | | 140 | | | | |

| Ala | Tyr | Ile | Arg | Lys | Arg | Phe | Thr | Lys | Ile | Glu | Thr | Asp | Ile | Leu | Leu |
| 145 | | | | | 150 | | | | | 155 | | | | | 160 |

| Ser | Leu | Ser | Leu | Phe | Asp | Leu | Arg | Ile | Ile | Leu | Lys | Ser | Gly | Glu | Leu |
| | | | | 165 | | | | | 170 | | | | | 175 | |

| Asp | Val | Ser | Ser | Glu | Asp | Asp | Val | Leu | Leu | Phe | Ile | Ile | Lys | Trp | Ser |
| | | | 180 | | | | | 185 | | | | | 190 | | |

| Arg | His | Lys | Lys | Ser | Asn | Arg | Arg | Lys | Ser | Phe | Thr | Leu | Val | Thr | Glu |
| | | 195 | | | | | 200 | | | | | 205 | | | |

| Val | Leu | Arg | Tyr | Asn | Tyr | Leu | Ser | Ile | Tyr | Gly | Lys | Tyr | Lys | Leu | Thr |
| | 210 | | | | | 215 | | | | | 220 | | | | |

| Lys | Trp | Leu | Ala | Arg | Phe | Gly | Lys | Asn | Asn | Val | Glu | Leu | Asn | Glu |
| 225 | | | | | 230 | | | | | 235 | | | | | 240 |

| Asn | Glu | Leu | Pro | Arg | Ile | Ser | Tyr | Gln | His | Arg | Phe | Thr | Asn | Arg | Arg |
| | | | | 245 | | | | | 250 | | | | | 255 | |

| Tyr | Thr | Met | Val | Thr | Pro | Ser | Ser | Phe | Ser | Ile | Asn | Met | Leu | Gly | Asn |
| | | | 260 | | | | | 265 | | | | | 270 | | |

| Val | Ser | Val | Lys | Asn | Glu | Leu | Ser | Ile | Ile | Asn | Ser | Ile | Ala | Glu | Asn |
| | | | 275 | | | | | 280 | | | | | 285 | | |

| His | Asn | Pro | Tyr | Cys | Gly | Ser | Val | Leu | Met | Asn | Asp | Ile | Leu | Tyr | Leu |
| | | 290 | | | | | 295 | | | | | 300 | | | |

| Ile | Gly | Gly | Ile | Asn | Lys | Ser | Leu | Asp | Pro | Val | Ser | Asp | Ile | Thr | Ser |
| 305 | | | | | 310 | | | | | 315 | | | | | 320 |

| Val | Asp | Thr | Arg | Ser | Phe | Ile | Glu | Leu | His | Thr | Pro | Pro | Leu | Leu | His |
| | | | | 325 | | | | | 330 | | | | | 335 | |

| Pro | Arg | Lys | Cys | Pro | Gly | Val | Ala | Ile | Phe | Lys | Asn | Arg | Ile | Tyr | Val |
| | | | 340 | | | | | 345 | | | | | 350 | | |

| Val | Gly | Gly | Ile | Gly | Tyr | Asp | Gly | Pro | Leu | Lys | Thr | Val | Glu | Ser | Trp |
| | | | 355 | | | | | 360 | | | | | 365 | | |

| Ser | Pro | Gly | Glu | Gln | Gln | Trp | Arg | Glu | Glu | Val | Pro | Leu | Leu | Gln | Pro |
| | 370 | | | | | 375 | | | | | 380 | | | | |

```
Arg  Phe  Asn  Pro  Cys  Ile  Ile  Gly  Thr  Asp  Asn  Asp  Leu  Tyr  Val  Val
385                      390                      395                      400

Gly  Gly  Ile  Ser  Glu  Asp  Asp  Lys  Thr  Ile  Glu  Ile  Tyr  Ser  Tyr  Glu
                    405                      410                      415

Glu  Asn  Thr  Trp  Ser  Ile  Gly  Asn  Ala  Met  Asn  Tyr  Ser  His  Phe  Gly
               420                      425                      430

Gly  Cys  Ile  Ala  Tyr  His  His  Gly  Tyr  Ile  Tyr  Met  Ile  Gly  Gly  Leu
          435                      440                      445

Ser  Phe  Ile  Asp  Asn  Ile  His  Val  Phe  Thr  Met  Val  Glu  Lys  Tyr  Asn
     450                      455                      460

Pro  His  Ser  Asn  Lys  Trp  Thr  Val  Glu  Lys  Ser  Leu  Pro  Phe  Pro  Arg
465                      470                      475                      480

Phe  Asn  Ser  Ser  Leu  Cys  Ile  Ile  Glu  Asp  Ser  Ile  Ala  Ile  Ile  Gly
                    485                      490                      495

Trp  Ile  Tyr  Tyr
               500
```

( 2 ) INFORMATION FOR SEQ ID NO:21:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Asn  Lys  Tyr  Asn  Asn  Tyr  Arg  Ala  Ile  Tyr  Phe  Leu  Tyr  Lys  Val
1                   5                        10                       15

Ile  Leu  Arg  Ile  His  Asn  Thr  Glu  Tyr  Ile  Ser  Gly  Thr  Leu  Gln  Arg
               20                       25                       30

Ser  Ile  Gln  Asn  Ile  Thr  Pro  Thr  Thr  Ser  Ser  Tyr  Thr  Tyr  Cys  Asp
          35                       40                       45

Asn  Ser  Lys  Arg  Arg  Arg  His  Arg  Phe  Arg  Asp  Thr  Glu  Ile  Leu  Lys
     50                       55                       60

Ala  Met  Gly  Ser  Lys  Met  Arg  Arg  Lys  Leu  Phe
65                   70                       75
```

( 2 ) INFORMATION FOR SEQ ID NO:22:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met  Ser  Leu  Tyr  Val  Lys  Cys  Val  Lys  Leu  Ser  Asn  Asn  Ala  Ile  Ile
1                   5                        10                       15

Pro  Asn  Arg  Ser  Met  Ser  Gly  Ser  Ala  Gly  Tyr  Asp  Leu  Tyr  Ser  Ala
               20                       25                       30

Tyr  Ser  Tyr  Thr  Val  Lys  Pro  Tyr  Asn  Arg  Ile  Leu  Val  Arg  Thr  Asp
          35                       40                       45

Ile  Cys  Leu  Met  Ile  Pro  Asp  Lys  Cys  Tyr  Gly  Arg  Ile  Ser  Pro  Arg
     50                       55                       60

Ser  Gly  Leu  Ser  Leu  Asn  Tyr  Asn  Ile  Asp  Ile  Gly  Gly  Gly  Val  Ile
65                   70                       75                       80

Asp  Ser  Asp  Tyr  Arg  Gly  Glu  Ile  Gly  Ile  Val  Phe  Ile  Asn  Asn  Gly
```

```
                         85                              90                              95
Cys  Ser  Asp  Phe  Asn  Ile  Lys  Val  Gly  Asp  Arg  Ile  Ala  Gln  Ile  Ile
               100                      105                     110

Phe  Glu  Arg  Val  Glu  Tyr  Pro  Ile  Met  Glu  Glu  Val  Lys  Cys  Leu  Glu
               115                      120                     125

Asp  Thr  Glu  Arg  Gly  Asn  Ser  Gly  Phe  Gly  Ser  Ser  Gly  Met
               130                      135                     140
```

( 2 ) INFORMATION FOR SEQ ID NO:23:

( i ) SEQUENCE CHARACTERISTICS:
    ( A ) LENGTH: 167 amino acids
    ( B ) TYPE: amino acid
    ( D ) TOPOLOGY: linear ( i i ) MOLECULE TYPE: protein ( x i ) SEQUENCE DESCRIPTION: SEQ ID NO:23:

```
Met  Tyr  Lys  Lys  Tyr  Asn  Ser  Asn  Val  Cys  Ile  Arg  Asn  Val  Leu  Tyr
 1                   5                        10                       15

Val  Tyr  Leu  Lys  Tyr  Asn  Thr  Ile  Asn  Lys  Leu  Ser  Arg  Tyr  Glu  Arg
               20                       25                      30

Met  Ile  Tyr  Thr  Lys  Ile  Lys  Asn  Gln  Cys  Glu  Ala  Ile  Lys  Tyr  Arg
               35                       40                      45

Tyr  Cys  Asn  Asp  Phe  Asn  Ser  Val  Thr  Cys  Ile  Leu  Glu  Tyr  Asp  Glu
          50                       55                           60

Asn  Lys  Tyr  Ile  Asp  Asn  Val  His  Lys  Glu  Val  Ile  Ser  Ile  Leu  Leu
 65                       70                       75                       80

Ser  Asp  Ser  Arg  Pro  Ser  Ile  Lys  Leu  Ala  Ala  Ile  Ser  Leu  Leu  Ser
               85                       90                              95

Ile  Ile  Ile  Asp  Lys  Leu  Ile  Cys  Arg  Asn  Ile  Arg  Ile  Ala  Lys  Tyr
               100                      105                     110

Ile  Ile  Asp  Asp  Ile  Ile  Asn  Ile  Ile  Ser  Glu  Asp  Gly  Ile  Tyr  Ile
               115                      120                     125

Ile  Leu  Phe  Leu  Asp  Glu  Phe  Asp  Lys  Tyr  Thr  Asp  Thr  Arg  Cys  Arg
          130                      135                          140

Arg  Arg  Gly  Leu  Ser  Met  Met  Ile  Ala  Ser  Ile  Val  Thr  Tyr  Tyr  Cys
145                      150                      155                      160

Leu  Arg  Tyr  Val  Leu  Lys  Ile
               165
```

( 2 ) INFORMATION FOR SEQ ID NO:24:

( i ) SEQUENCE CHARACTERISTICS:
    ( A ) LENGTH: 134 amino acids
    ( B ) TYPE: amino acid
    ( D ) TOPOLOGY: linear ( i i ) MOLECULE TYPE: protein ( x i ) SEQUENCE DESCRIPTION: SEQ ID NO:24:

```
Met  Asn  Arg  Asn  Met  Trp  Ile  Val  Leu  Ser  Cys  Val  Leu  Tyr  Met  Ile
 1                   5                        10                       15

Tyr  Ile  Cys  Asn  Gly  Arg  Asp  Val  Leu  Leu  Tyr  Pro  Pro  His  Lys  Lys
               20                       25                      30

Thr  Asn  Lys  Val  Ile  Val  Lys  Cys  Asn  Gly  Tyr  Thr  Asn  Ser  Thr  Tyr
               35                       40                      45

Ser  Ile  Leu  Tyr  Trp  Met  Val  Gly  Asn  Asn  Thr  Phe  Val  Glu  Gln
          50                       55                           60
```

| Leu | Asn | Ser | Asp | His | Tyr | Lys | Glu | Lys | Tyr | Asn | Ser | Thr | Glu | Lys |
| 65 |     |     |     |     | 70  |     |     |     | 75  |     |     |     |     | 80  |

| Asn | Glu | His | Met | Tyr | Lys | Leu | Arg | Thr | Asp | Leu | Ile | Ile | Tyr | Asn | Ile |
|     |     |     |     | 85  |     |     |     |     | 90  |     |     |     |     | 95  |     |

| Thr | Ser | Glu | Met | Glu | Met | Thr | Lys | Leu | Thr | Cys | Val | Leu | Ser | Asp | Ile |
|     |     |     | 100 |     |     |     |     | 105 |     |     |     |     | 110 |     |     |

| Tyr | Thr | Pro | Ile | Lys | Ala | Ser | Ile | Ile | Leu | Asn | Asn | Leu | Trp | Ser | Cys |
|     |     | 115 |     |     |     |     | 120 |     |     |     |     | 125 |     |     |     |

| Leu | Asn | Thr | Thr | Gln | Val |
|     | 130 |     |     |     |     |

( 2 ) INFORMATION FOR SEQ ID NO:25:

( i ) SEQUENCE CHARACTERISTICS:
        ( A ) LENGTH: 86 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| Met | Ser | Thr | Met | Asn | Thr | Leu | Ala | Phe | Cys | Tyr | Gly | Leu | Pro | Asn | Ile |
| 1   |     |     |     | 5   |     |     |     |     | 10  |     |     |     |     | 15  |     |

| Asn | Asp | Ile | Thr | Gln | Gly | Ile | Ile | Phe | Val | Arg | Asn | Asn | Ile | Phe | Tyr |
|     |     |     | 20  |     |     |     |     | 25  |     |     |     |     | 30  |     |     |

| Ser | Tyr | Leu | Thr | Asp | Tyr | Ala | Met | Glu | Ala | Cys | Ile | Leu | Asn | Tyr | Ile |
|     |     |     | 35  |     |     |     |     | 40  |     |     |     |     | 45  |     |     |

| Asn | Ile | Arg | Ala | Asp | Lys | Ile | Glu | Asp | Leu | Lys | Lys | Ser | Leu | Val | Gly |
|     |     |     | 50  |     |     |     |     | 55  |     |     |     |     | 60  |     |     |

| Lys | Thr | Ile | Ser | Val | Arg | Val | Ile | Arg | Val | Asp | Val | Leu | Lys | Gly | Tyr |
| 65  |     |     |     |     | 70  |     |     |     | 75  |     |     |     |     |     | 80  |

| Ile | Asp | Val | Ser | Ile | Val |
|     |     |     |     | 85  |     |

( 2 ) INFORMATION FOR SEQ ID NO:26:

( i ) SEQUENCE CHARACTERISTICS:
        ( A ) LENGTH: 155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| Met | Asp | Pro | Val | Cys | Trp | Ile | Cys | Lys | Asp | Asp | Tyr | Ser | Ile | Glu | Lys |
| 1   |     |     |     | 5   |     |     |     |     | 10  |     |     |     |     | 15  |     |

| Asn | Tyr | Cys | Asn | Cys | Lys | Asn | Glu | Tyr | Lys | Val | Val | His | Asp | Glu | Cys |
|     |     |     | 20  |     |     |     |     | 25  |     |     |     |     | 30  |     |     |

| Met | Lys | Lys | Trp | Ile | Gln | Tyr | Ser | Arg | Glu | Arg | Ser | Cys | Lys | Leu | Cys |
|     |     | 35  |     |     |     |     | 40  |     |     |     |     | 45  |     |     |     |

| Asn | Lys | Glu | Tyr | Asn | Ile | Ile | Ser | Val | Arg | Lys | Pro | Phe | Ser | Gln | Trp |
|     | 50  |     |     |     |     | 55  |     |     |     |     | 60  |     |     |     |     |

| Val | Phe | Ser | Ile | Lys | Asp | Cys | Lys | Lys | Ser | Ala | Ile | Leu | Tyr | Ala | Thr |
| 65  |     |     |     |     | 70  |     |     |     |     | 75  |     |     |     |     | 80  |

| Leu | Phe | Leu | Cys | Thr | Phe | Ile | Ile | Ser | Leu | Val | Leu | Thr | Arg | Ile | Asn |
|     |     |     |     | 85  |     |     |     |     | 90  |     |     |     |     | 95  |     |

| Ile | Thr | Lys | Ile | Ile | Asp | Thr | Ser | Lys | Asn | Asp | Val | Ser | Phe | Lys | Leu |
|     |     |     | 100 |     |     |     |     | 105 |     |     |     |     | 110 |     |     |

| Val | Thr | Met | Ile | Phe | Tyr | Leu | Leu | Pro | Phe | Val | Ile | Thr | Cys | Ile | Ser |
|     |     |     | 115 |     |     |     |     | 120 |     |     |     |     | 125 |     |     |

```
Phe  Ile  Thr  Leu  Ile  Val  Tyr  Leu  Tyr  Lys  Tyr  Cys  Lys  Ile  Ser  Ala
     130                 135                      140

Lys  Asn  Asn  Thr  Tyr  Asp  Thr  Ile  Tyr  Glu  Leu
145                      150                      155
```

( 2 ) INFORMATION FOR SEQ ID NO:27:

( i ) SEQUENCE CHARACTERISTICS:
      ( A ) LENGTH: 274 amino acids
      ( B ) TYPE: amino acid
      ( D ) TOPOLOGY: linear ( i i ) MOLECULE TYPE: protein ( x i ) SEQUENCE DESCRIPTION: SEQ ID NO:27:

```
Met  His  Phe  Ile  Phe  Ile  Ile  Leu  Ser  Leu  Ser  Phe  Val  Val  Asn  Ala
 1                    5                   10                       15

Asp  Val  Phe  Pro  Ser  Ser  Val  Thr  Leu  Ser  Ser  Asn  Asp  Phe  Asp  Thr
               20                       25                        30

Ile  Ile  Lys  Trp  Asp  Asn  Asn  Val  Ile  Ser  Tyr  Asp  Val  Glu  Leu  Met
          35                        40                    45

Gln  Tyr  Ser  His  Asp  Glu  Trp  Arg  Thr  Val  Cys  Thr  Asn  Ser  Leu  Gly
     50                        55                       60

Tyr  Cys  Asn  Leu  Thr  Asn  Ser  Asp  Ile  Asp  Asn  Asp  Asp  Glu  Thr  Trp
 65                      70                        75                        80

Val  Arg  Phe  Lys  Tyr  Glu  Asn  Lys  Thr  Ser  Asn  Glu  His  Asn  Ile  Gly
                85                       90                         95

Arg  Val  Cys  Glu  Ile  Val  Gln  Ile  Thr  Ser  Pro  Ile  Val  Asn  Met  Thr
               100                      105                      110

Arg  Asp  Gly  Ser  Ile  Ile  Leu  Leu  Asp  Ile  His  His  Pro  Met  Thr  Tyr
               115                      120                      125

Asp  Asn  Gln  Tyr  Tyr  Ile  Tyr  Asn  Asn  Ile  Thr  Leu  Cys  Gly  Phe  Glu
               130                      135                      140

Phe  Ile  Tyr  Glu  Ala  Thr  Phe  Ile  Ile  Asn  Asp  Thr  Ile  Ile  Pro  Tyr
145                      150                      155                      160

Ser  Ile  Asp  Asn  Gln  Tyr  Cys  Asp  Asp  Val  His  Cys  Leu  Phe  Tyr  Phe
                    165                      170                      175

Ile  Ser  Gln  Glu  Pro  Val  Cys  Val  Tyr  Val  Met  Gly  Met  Glu  Gln  Tyr
               180                      185                      190

Tyr  Glu  Phe  Gly  Pro  Lys  Lys  Thr  Asp  Asn  Ser  Thr  Arg  Val  Cys  Val
               195                      200                      205

Asp  Gly  Leu  Ile  Pro  Arg  Lys  Ile  Asp  Thr  Tyr  Phe  Ile  Lys  Asp  Phe
     210                      215                      220

Asp  Asp  Ile  Asp  Arg  Val  Asn  Asn  Arg  Leu  Tyr  Arg  Val  Val  Ser  Asp
225                      230                      235                      240

Lys  Tyr  Glu  Ser  Asn  Ile  Ser  Ser  Lys  Phe  Met  His  Leu  Tyr  Asn  Asn
                    245                      250                      255

Ile  Leu  Ser  Ser  Phe  Lys  Leu  Ile  Leu  Gln  Glu  Leu  Met  Val  Asn  Thr
               260                      265                      270

Glu  Gln
```

( 2 ) INFORMATION FOR SEQ ID NO:28:

( i ) SEQUENCE CHARACTERISTICS:
      ( A ) LENGTH: 236 amino acids
      ( B ) TYPE: amino acid
      ( D ) TOPOLOGY: linear ( i i ) MOLECULE TYPE: protein ( x i ) SEQUENCE DESCRIPTION: SEQ ID NO:28:

| Met | Asn | Ser | Tyr | Ile | Val | Ile | Lys | Asn | Ser | Leu | Arg | Asp | Tyr | Arg | Ser |
|---|---|---|---|---|---|---|---|---|---|---|---|---|---|---|---|
| 1 | | | | 5 | | | | | 10 | | | | | 15 | |

| Gly | Arg | Ile | Ile | Arg | Lys | Tyr | Ile | Arg | Lys | Leu | Asn | Lys | Asp | Glu | Tyr |
|---|---|---|---|---|---|---|---|---|---|---|---|---|---|---|---|
| | | | 20 | | | | | 25 | | | | | 30 | | |

| Lys | His | Phe | Cys | Ala | Val | Phe | Arg | Leu | Asn | Val | Asp | Phe | Ser | Gln | Asp |
|---|---|---|---|---|---|---|---|---|---|---|---|---|---|---|---|
| | | 35 | | | | 40 | | | | | 45 | | | | |

| Asp | Lys | Asn | Pro | Ser | Arg | Lys | Glu | Val | Ile | Arg | Ile | Ile | Asp | Glu | Glu |
|---|---|---|---|---|---|---|---|---|---|---|---|---|---|---|---|
| | 50 | | | | | 55 | | | | | 60 | | | | |

| Phe | Asn | Phe | Cys | Asp | Leu | Arg | Leu | Phe | Tyr | Asp | Ile | Met | Thr | Val | Val |
|---|---|---|---|---|---|---|---|---|---|---|---|---|---|---|---|
| 65 | | | | | 70 | | | | | 75 | | | | | 80 |

| Pro | Asn | His | Met | Asn | Val | Ala | Ser | Ile | Ile | Tyr | Ser | Glu | Tyr | Glu | Tyr |
|---|---|---|---|---|---|---|---|---|---|---|---|---|---|---|---|
| | | | | 85 | | | | | 90 | | | | | 95 | |

| Leu | Leu | Lys | Lys | Ser | Asn | Tyr | Lys | Asn | Lys | Lys | Ile | Asn | Tyr | Thr | Ile |
|---|---|---|---|---|---|---|---|---|---|---|---|---|---|---|---|
| | | | 100 | | | | | 105 | | | | | 110 | | |

| Leu | Asp | Lys | Ile | Asn | Lys | Tyr | His | Ser | Ile | Asp | Asp | Ile | Ile | Phe | Met |
|---|---|---|---|---|---|---|---|---|---|---|---|---|---|---|---|
| | | 115 | | | | | 120 | | | | | 125 | | | |

| Tyr | Leu | His | Trp | Arg | Lys | Lys | Tyr | Asn | Asn | Thr | Cys | Ala | Cys | Gly | Lys |
|---|---|---|---|---|---|---|---|---|---|---|---|---|---|---|---|
| | 130 | | | | | 135 | | | | | 140 | | | | |

| Leu | Phe | Lys | Glu | Leu | Met | Lys | Tyr | Asp | Ile | Leu | Ala | Thr | Lys | Tyr | Ile |
|---|---|---|---|---|---|---|---|---|---|---|---|---|---|---|---|
| 145 | | | | | 150 | | | | | 155 | | | | | 160 |

| Tyr | Asn | Asp | Ile | Ile | Asn | Thr | Tyr | Lys | Glu | Gly | Asp | Thr | Ile | Ser | Ile |
|---|---|---|---|---|---|---|---|---|---|---|---|---|---|---|---|
| | | | | 165 | | | | | 170 | | | | | 175 | |

| Asn | Ile | Arg | Leu | Lys | Cys | Lys | Asp | Asp | Ile | Ile | Lys | His | Cys | Lys | Ser |
|---|---|---|---|---|---|---|---|---|---|---|---|---|---|---|---|
| | | | 180 | | | | | 185 | | | | | 190 | | |

| Ser | Ile | Gly | Met | Phe | Ala | Ile | Leu | Ser | Ser | Lys | Ile | Ile | Asp | Val | Asp |
|---|---|---|---|---|---|---|---|---|---|---|---|---|---|---|---|
| | | 195 | | | | | 200 | | | | | 205 | | | |

| Phe | Asp | Val | Ile | Phe | Phe | Ser | Gln | Ile | Ser | Ile | Arg | Tyr | Arg | Leu | Ile |
|---|---|---|---|---|---|---|---|---|---|---|---|---|---|---|---|
| | 210 | | | | | 215 | | | | | 220 | | | | |

| Phe | Lys | Lys | Tyr | Leu | Ile | Gln | Ser | Leu | Tyr | Leu | Gln |
|---|---|---|---|---|---|---|---|---|---|---|---|
| 225 | | | | | 230 | | | | | 235 | |

( 2 ) INFORMATION FOR SEQ ID NO:29:

( i ) SEQUENCE CHARACTERISTICS:
        ( A ) LENGTH: 530 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

| Met | Asn | Ser | Leu | Leu | Leu | Arg | Leu | His | Asp | Phe | Phe | Lys | His | Gly | Ile |
|---|---|---|---|---|---|---|---|---|---|---|---|---|---|---|---|
| 1 | | | | 5 | | | | | 10 | | | | | 15 | |

| Met | Cys | Asp | Ile | Lys | Ile | Val | Ser | Ile | Glu | Asn | Asn | Lys | Thr | Ile | Ser |
|---|---|---|---|---|---|---|---|---|---|---|---|---|---|---|---|
| | | | 20 | | | | | 25 | | | | | 30 | | |

| Ala | His | Arg | Leu | Ile | Leu | Ser | Met | Tyr | Ser | Lys | Tyr | Phe | Tyr | Asn | Ile |
|---|---|---|---|---|---|---|---|---|---|---|---|---|---|---|---|
| | | 35 | | | | | 40 | | | | | 45 | | | |

| Phe | Asn | Ser | Asp | Phe | Ile | Asp | Lys | Asn | Asn | Asp | Glu | Ile | Tyr | Ile | Cys |
|---|---|---|---|---|---|---|---|---|---|---|---|---|---|---|---|
| | 50 | | | | | 55 | | | | | 60 | | | | |

| Ala | Asp | Tyr | Asp | Ile | Leu | Tyr | Ile | Ile | Leu | Glu | Phe | Met | Tyr | Thr | Gly |
|---|---|---|---|---|---|---|---|---|---|---|---|---|---|---|---|
| 65 | | | | | 70 | | | | | 75 | | | | | 80 |

| Asn | Ile | Val | Leu | Thr | Lys | Asp | Asn | Ile | Glu | Leu | Val | Ile | Gln | Val | Cys |
|---|---|---|---|---|---|---|---|---|---|---|---|---|---|---|---|
| | | | | 85 | | | | | 90 | | | | | 95 | |

| Asp | Tyr | Leu | Cys | Ile | Asp | Ser | Leu | Ile | Lys | Ile | Cys | Glu | Glu | Tyr | Ile |

|     |     |     |     |     |     |     |     |     |     |     |     |     |     |     |
|-----|-----|-----|-----|-----|-----|-----|-----|-----|-----|-----|-----|-----|-----|-----|
|     |     |     |     |     | 100 |     |     |     | 105 |     |     |     | 110 |     |
| Cys | Gly | Ile | Ile | Asp | Glu | Thr | Asn | Cys | Ile | His | Leu | Leu | Asn | Phe | Ser |
|     |     |     | 115 |     |     |     | 120 |     |     |     | 125 |     |     |     |
| Asp | Thr | Tyr | Asn | Leu | Gln | Arg | Leu | Arg | Glu | Met | Ser | Lys | Trp | Tyr | Leu |
|     | 130 |     |     |     |     | 135 |     |     |     |     | 140 |     |     |     |
| Pro | Lys | Ile | Ile | Asn | Asn | Asn | Lys | Leu | Val | Val | Glu | Leu | Asp | Ile | Asp |
| 145 |     |     |     |     | 150 |     |     |     |     | 155 |     |     |     |     | 160 |
| Asp | Met | Ile | Leu | Ile | Ile | Lys | Glu | Ile | Lys | Tyr | Ile | Ala | Cys | Glu | Tyr |
|     |     |     |     | 165 |     |     |     |     | 170 |     |     |     | 175 |     |
| Ile | Val | Lys | Lys | Ile | Ile | Leu | Asn | Trp | Ile | Val | His | Lys | Asp | Glu | Arg |
|     |     |     | 180 |     |     |     |     | 185 |     |     |     |     | 190 |     |
| Ile | Ile | Tyr | Thr | Lys | Lys | Leu | Met | Lys | His | Ile | Asn | Asp | Gln | Asp | His |
|     |     |     | 195 |     |     |     | 200 |     |     |     |     | 205 |     |     |
| Tyr | Thr | Ser | Leu | Ser | Asp | Ile | Glu | Leu | Tyr | Asn | Asn | Ile | Arg | Glu | Arg |
|     | 210 |     |     |     |     | 215 |     |     |     |     | 220 |     |     |     |
| Ile | Tyr | Asp | Asn | Lys | Glu | His | Asp | Val | Asp | Ile | Ser | His | Asn | Phe | Ile |
| 225 |     |     |     |     | 230 |     |     |     |     | 235 |     |     |     |     | 240 |
| Ile | Met | Val | Gly | Gly | Lys | Lys | Ile | Phe | Asn | Ile | Thr | Ala | Phe | Asn | Pro |
|     |     |     |     | 245 |     |     |     |     | 250 |     |     |     | 255 |     |
| Leu | Ser | Asn | Lys | Lys | His | Ile | Ile | Asp | Arg | Tyr | Asp | Asp | Met | Phe | Gly |
|     |     |     | 260 |     |     |     |     | 265 |     |     |     |     | 270 |     |
| Cys | Lys | Thr | His | Phe | Ser | Val | Val | Tyr | Leu | Asn | Ser | Ile | Leu | Tyr | Ile |
|     |     | 275 |     |     |     |     | 280 |     |     |     |     | 285 |     |     |
| Ile | Gly | Gly | Lys | Lys | Arg | Gly | Tyr | Phe | Thr | Lys | Glu | Val | Leu | Ser | Tyr |
|     | 290 |     |     |     |     | 295 |     |     |     |     | 300 |     |     |     |
| Asn | Ile | Lys | Asn | Lys | Leu | Trp | Cys | Tyr | Glu | Pro | Glu | Leu | Asn | Tyr | Phe |
| 305 |     |     |     |     | 310 |     |     |     |     | 315 |     |     |     |     | 320 |
| Arg | Tyr | Asp | Thr | Ser | Val | Cys | Val | Ser | Asn | Gly | Met | Ile | Tyr | Ser | Ile |
|     |     |     |     | 325 |     |     |     |     | 330 |     |     |     | 335 |     |
| Gly | Gly | Lys | Asp | Thr | Asn | Gly | Tyr | Met | Thr | Asn | Ile | Val | Glu | Phe | Trp |
|     |     |     | 340 |     |     |     |     | 345 |     |     |     |     | 350 |     |
| Lys | Pro | Glu | Trp | Lys | Ser | Trp | Tyr | Asp | Gly | Gln | His | Leu | Cys | Tyr | Pro |
|     |     | 355 |     |     |     |     | 360 |     |     |     |     | 365 |     |     |
| Arg | Cys | Tyr | Met | Ser | Leu | Val | Asp | Tyr | Asn | Asn | Glu | Val | Tyr | Thr | Ile |
|     | 370 |     |     |     |     | 375 |     |     |     |     | 380 |     |     |     |
| Gly | Gly | Leu | Lys | Thr | Ser | Ile | Thr | Asp | Glu | Phe | Asn | Ile | Glu | Met | Ile |
| 385 |     |     |     |     | 390 |     |     |     |     | 395 |     |     |     |     | 400 |
| Val | Ser | Asp | Asp | Ala | Val | Glu | Lys | Leu | Thr | Asp | His | Ser | Trp | Met | Lys |
|     |     |     |     | 405 |     |     |     |     | 410 |     |     |     | 415 |     |
| Leu | Lys | Gln | Phe | Pro | Ile | Ala | Lys | Ser | Gly | Ile | Ser | Ser | Ile | Val | Tyr |
|     |     |     | 420 |     |     |     |     | 425 |     |     |     |     | 430 |     |
| Asn | Asp | Phe | Ile | Tyr | Cys | Ile | Gly | Gly | Arg | Ile | Asp | Thr | Pro | His | Ile |
|     |     | 435 |     |     |     |     | 440 |     |     |     |     | 445 |     |     |
| Ser | Ile | Glu | His | Thr | Asn | Asp | Val | Tyr | Ile | Tyr | Ser | Ser | Arg | Asp | Asp |
|     | 450 |     |     |     |     | 455 |     |     |     |     | 460 |     |     |     |
| Cys | Trp | Lys | Tyr | Leu | Ser | Asn | Thr | Asn | Val | Lys | Arg | Ser | Phe | Cys | Leu |
| 465 |     |     |     |     | 470 |     |     |     |     | 475 |     |     |     |     | 480 |
| Ser | Cys | Val | Phe | Asn | Asn | Glu | Leu | Tyr | Ile | Ile | Gly | Gly | Tyr | Asn | Thr |
|     |     |     |     | 485 |     |     |     |     | 490 |     |     |     | 495 |     |
| Asn | Ser | Val | Glu | Lys | Tyr | Asn | Lys | Leu | Lys | Asn | Thr | Trp | Lys | Arg | Leu |
|     |     |     | 500 |     |     |     |     | 505 |     |     |     |     | 510 |     |
| Asn | Asp | Ile | Pro | Lys | Phe | Glu | Glu | Cys | Val | Asn | Glu | Ala | Ser | Ala | Ile |
|     |     |     | 515 |     |     |     |     | 520 |     |     |     |     | 525 |     |

Tyr Leu
530

(2) INFORMATION FOR SEQ ID NO:30:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:30:

```
Met Ser Asp Cys Ile Phe Val Phe Gln Ile Pro Phe Ile Val Tyr Ser
 1               5                  10                  15
Lys Leu Asp Gln Trp Ile Phe Gly Asn Ile Leu Cys Lys Ile Met Ser
            20                  25                  30
Val Leu Tyr Tyr Val Gly Phe Phe Ser Asn Met Phe Ile Ile Thr Leu
        35                  40                  45
Met Ser Ile Asp Arg Tyr Phe Ala Ile Val His Pro Ile Lys Arg Gln
    50                  55                  60
Pro Tyr Arg Thr Lys Arg Ile Gly Ile Leu Met Cys Cys Ser Ala Trp
65                  70                  75                  80
Leu Leu Ser Leu Ile Leu Ser Ser Pro Val Ser Lys Leu Tyr Glu Asn
                85                  90                  95
Ile Pro His Met Ser Lys Asp Ile Tyr Gln Cys Thr Leu Thr Asn Glu
            100                 105                 110
Asn Asp Ser Ile Ile Ala Phe Ile Lys Arg Leu Met Gln Ile Glu Ile
            115                 120                 125
Thr Ile Leu Gly Phe Leu Ile Pro Ile Ile Ile Phe Val Tyr Cys Tyr
    130                 135                 140
Tyr Arg Ile Phe Ser Thr Val Val Arg Leu Arg Asn Arg Arg Lys Tyr
145                 150                 155                 160
Lys Ser Ile Lys Ile Val Leu Met Ile Val Val Cys Ser Leu Ile Cys
                165                 170                 175
Trp Ile Pro Leu Tyr Ile Val Leu Met Ile Ala Thr Ile Val Ser Leu
            180                 185                 190
Tyr Thr Ser Asn Ile Phe Arg His Leu Cys Leu Tyr Leu Asn Leu Ala
        195                 200                 205
Tyr Ala Ile Thr Phe Ser Glu Thr Ile Ser Leu Ala Arg Cys Cys Ile
    210                 215                 220
Asn Pro Ile Ile Tyr Thr Leu Ile Gly Glu His Val Arg Ser Arg Ile
225                 230                 235                 240
Ser Ser Ile Cys Ser Cys Ile Tyr Arg Asp Asn Arg Ile Arg Lys Lys
                245                 250                 255
Leu Phe Ser Arg Lys Ser Ser Ser Ser Asn Ile Ile
            260                 265
```

(2) INFORMATION FOR SEQ ID NO:31:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO:31:

```
Met Leu Ser Tyr Ile Ile Asn Pro Leu Leu Ser Ile Val Tyr Phe Ile
 1               5                  10                  15
```

| Leu | Gly | Asn | Val | Ser | Lys | Leu | Leu | Thr | Tyr | Ile | Leu | Met | Lys | Ile | Met |
|---|---|---|---|---|---|---|---|---|---|---|---|---|---|---|---|
| | | | 20 | | | | | 25 | | | | | 30 | | |

| Ile | Phe | Leu | Leu | Arg | Ala | Val | Asn | Pro | Tyr | Ser | Leu | Ile | Ser | Asn | Arg |
|---|---|---|---|---|---|---|---|---|---|---|---|---|---|---|---|
| | | 35 | | | | | 40 | | | | | 45 | | | |

| Gly | Trp | Leu | Ser | Leu | Asp | Ser | Ile | Asn | Pro | Phe | Lys | Lys | Glu | Lys | Arg |
|---|---|---|---|---|---|---|---|---|---|---|---|---|---|---|---|
| | 50 | | | | | 55 | | | | | 60 | | | | |

| Arg | Glu | Ser | Phe | Leu | Ser | Ser | Leu | Asn | Pro | Phe | Arg | Lys | Glu | Glu | Thr |
|---|---|---|---|---|---|---|---|---|---|---|---|---|---|---|---|
| 65 | | | | | 70 | | | | | 75 | | | | | 80 |

| Lys | Lys | Lys | Glu | Gly | Phe | Phe | Ser | Gly | Trp | Phe | Gly |
|---|---|---|---|---|---|---|---|---|---|---|---|
| | | | | 85 | | | | | 90 | | |

( 2 ) INFORMATION FOR SEQ ID NO:32:

( i ) SEQUENCE CHARACTERISTICS:
      ( A ) LENGTH: 340 amino acids
      ( B ) TYPE: amino acid
      ( D ) TOPOLOGY: linear ( i i ) MOLECULE TYPE: protein ( x i ) SEQUENCE DESCRIPTION: SEQ ID NO:32:

| Met | Ile | Thr | Lys | Ala | Ile | Val | Ile | Leu | Ser | Ile | Ile | Thr | Ala | Tyr | Val |
|---|---|---|---|---|---|---|---|---|---|---|---|---|---|---|---|
| 1 | | | | 5 | | | | | 10 | | | | | 15 | |

| Asp | Ala | Ser | Ala | Phe | Leu | Val | Tyr | Asn | Tyr | Thr | Tyr | Thr | Leu | Gln | Asp |
|---|---|---|---|---|---|---|---|---|---|---|---|---|---|---|---|
| | | | 20 | | | | | 25 | | | | | 30 | | |

| Asp | Asn | His | Arg | Tyr | Asp | Phe | Glu | Val | Thr | Asp | Tyr | Phe | Asn | Asp | Ile |
|---|---|---|---|---|---|---|---|---|---|---|---|---|---|---|---|
| | | 35 | | | | | 40 | | | | | 45 | | | |

| Leu | Ile | Lys | Arg | Leu | Lys | Leu | Asn | Ser | Glu | Thr | Gly | Arg | Pro | Glu | Leu |
|---|---|---|---|---|---|---|---|---|---|---|---|---|---|---|---|
| | 50 | | | | | 55 | | | | | 60 | | | | |

| Arg | Asn | Glu | Pro | Pro | Thr | Trp | Phe | Asn | Glu | Thr | Lys | Ile | Arg | Tyr | Tyr |
|---|---|---|---|---|---|---|---|---|---|---|---|---|---|---|---|
| 65 | | | | | 70 | | | | | 75 | | | | | 80 |

| Pro | Lys | Asn | Asn | Tyr | Asn | Phe | Met | Phe | Trp | Leu | Asn | Arg | Met | Ser | Glu |
|---|---|---|---|---|---|---|---|---|---|---|---|---|---|---|---|
| | | | | 85 | | | | | 90 | | | | | 95 | |

| Thr | Leu | Asp | Glu | Ile | Asn | Lys | Leu | Pro | Glu | Thr | Ser | Asn | Pro | Tyr | Lys |
|---|---|---|---|---|---|---|---|---|---|---|---|---|---|---|---|
| | | | 100 | | | | | 105 | | | | | 110 | | |

| Thr | Met | Ser | Leu | Thr | Ile | Gly | Cys | Thr | Asp | Leu | Arg | Gln | Leu | Gln | Val |
|---|---|---|---|---|---|---|---|---|---|---|---|---|---|---|---|
| | | 115 | | | | | 120 | | | | | 125 | | | |

| Asn | Phe | Gly | Tyr | Val | Thr | Val | Gly | Gly | Asn | Ile | Trp | Thr | Arg | Phe | Asp |
|---|---|---|---|---|---|---|---|---|---|---|---|---|---|---|---|
| | 130 | | | | | 135 | | | | | 140 | | | | |

| Pro | Lys | Asn | Lys | Arg | Phe | Ser | Lys | Val | Arg | Ser | Arg | Thr | Phe | Pro | Lys |
|---|---|---|---|---|---|---|---|---|---|---|---|---|---|---|---|
| 145 | | | | | 150 | | | | | 155 | | | | | 160 |

| Val | Gly | Met | Leu | Thr | Val | Lys | Ser | Gln | His | Trp | Glu | Arg | Val | Met | Glu |
|---|---|---|---|---|---|---|---|---|---|---|---|---|---|---|---|
| | | | | 165 | | | | | 170 | | | | | 175 | |

| His | Leu | Gly | Ser | Met | Val | Thr | Leu | Thr | Cys | Pro | Phe | Thr | Ala | Asp | Asp |
|---|---|---|---|---|---|---|---|---|---|---|---|---|---|---|---|
| | | | 180 | | | | | 185 | | | | | 190 | | |

| Tyr | Tyr | Lys | Ile | Ser | Lys | Gly | Tyr | Ile | Asp | Lys | Pro | Val | Lys | Pro | Thr |
|---|---|---|---|---|---|---|---|---|---|---|---|---|---|---|---|
| | | | 195 | | | | | 200 | | | | | 205 | | |

| Val | Thr | Val | Thr | Gly | Ile | Glu | Arg | Gly | Asp | Asn | Thr | Thr | Leu | Ile | Cys |
|---|---|---|---|---|---|---|---|---|---|---|---|---|---|---|---|
| | 210 | | | | | 215 | | | | | 220 | | | | |

| Thr | Phe | Asp | Asn | His | Tyr | Pro | Ser | Ser | Val | Ala | Val | Lys | Trp | Tyr | Asn |
|---|---|---|---|---|---|---|---|---|---|---|---|---|---|---|---|
| 225 | | | | | 230 | | | | | 235 | | | | | 240 |

| Ile | Glu | Asp | Phe | Ala | Pro | Asp | Tyr | Arg | Tyr | Asp | Pro | Tyr | Val | Asn | Glu |
|---|---|---|---|---|---|---|---|---|---|---|---|---|---|---|---|
| | | | | 245 | | | | | 250 | | | | | 255 | |

| Leu | Leu | Pro | Asp | Thr | Asp | Tyr | Leu | Pro | Gly | Glu | Pro | Gly | Tyr | Pro | Thr |
|---|---|---|---|---|---|---|---|---|---|---|---|---|---|---|---|
| | | | 260 | | | | | 265 | | | | | 270 | | |

| Ile | Thr | Arg | Arg | Leu | Gly | Asp | Lys | Tyr | Leu | Phe | Thr | Ser | Ser | Pro | Arg |
|---|---|---|---|---|---|---|---|---|---|---|---|---|---|---|---|

|           |           |           |           | 275       |           |           |           | 280       |           |           |           | 285       |           |           |
|-----------|-----------|-----------|-----------|-----------|-----------|-----------|-----------|-----------|-----------|-----------|-----------|-----------|-----------|-----------|
| Val | Met | Val | Pro | Thr | Ile | Met | Ser | Asn | Arg | Ile | Ala | Cys | Val | Gly | Phe |
|     | 290 |     |     |     |     | 295 |     |     |     | 300 |     |     |     |     |     |

```
Val Met Val Pro Thr Ile Met Ser Asn Arg Ile Ala Cys Val Gly Phe
    290                 295                 300

His Ser Thr Leu Glu Pro Ser Ile Tyr Arg Cys Val Asn Cys Ser Gly
305                 310                 315                 320

Pro Glu Pro Val Leu Gln Tyr Gln Gly Asp Arg Arg Asn Asp Leu Glu
                325                 330                 335

Asp Glu Glu Asp
            340
```

( 2 ) INFORMATION FOR SEQ ID NO:33:

( i ) SEQUENCE CHARACTERISTICS:
        ( A ) LENGTH: 67 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:33:

```
Met Met Ile Ser Ile Ile Tyr Gln Gln Glu Val Met Val Ser Tyr Leu
1               5                   10                  15

Lys Trp Ile Asn Thr Leu Leu Asn Leu Phe Met Asn Gln Ile Asn Ser
                20                  25                  30

Ile Val Pro Leu Ile Gln Leu Pro Ser Ile Gln Tyr Leu Asn Phe Tyr
            35                  40                  45

Ile Ile Ile Leu Arg Glu Met Arg Lys Asn Leu Ser Phe Val His Gly
        50                  55                  60

Gln Trp Val
65
```

( 2 ) INFORMATION FOR SEQ ID NO:34:

( i ) SEQUENCE CHARACTERISTICS:
        ( A ) LENGTH: 215 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:34:

```
Met Glu Asn Pro Val Arg Ile Asn Thr Leu Tyr Asn Val Phe Val Glu
1               5                   10                  15

Arg Tyr Ile Glu Asn Leu Ser Ile Tyr Ser Ile Pro Ile Asn Ser Thr
                20                  25                  30

Cys Gly Ile His Ile Gly Glu Ile Lys Gly Thr Phe Lys Arg Cys Phe
            35                  40                  45

Leu Lys Ile Leu Asn Met Cys Ile Asn Asp Lys Glu Leu Ser Phe Asn
        50                  55                  60

Ile Leu Ile Lys Thr Leu Lys Asp Val Thr Ser Thr Leu Ser Gln Lys
65                  70                  75                  80

Glu Lys Glu Glu Leu Ser Lys Glu Ile Gly Ile Asp Ile Leu Asn Asn
                85                  90                  95

Asp Pro Lys Tyr Val Pro Glu Ile Ile Arg Asn Cys Ser Ser Ser Ala
            100                 105                 110

Asp Val Thr Asn Ile Ile Asp Ile Gln Thr Leu Asp Val Gly Lys Cys
        115                 120                 125

Ile Ala Pro Tyr Asp Lys Gln Ile Leu Leu Gln Ile Val Asn Ser Gly
```

```
                130                       135                          140
         Thr  Ala  Glu  Ala  Asn  Cys  Val  Met  Asn  Ser  Ile  Met  Asn  Ser  Met  Asn
         145                      150                      155                      160

Arg  Arg  Tyr  Ile  Asp  Asn  Ala  Asn  Ile  Tyr  Asn  Tyr  Leu  Asn  Leu  Thr
                            165                      170                      175

Asn  Arg  Pro  Trp  Phe  Ile  Phe  Ser  Ile  Ile  Ile  Ile  Ala  Ile  Ile  Phe
                            180                      185                      190

Val  Ile  Gly  Ile  Cys  Ser  Ile  Lys  Arg  Arg  Ile  Gly  Ile  Lys  Tyr  Lys
                       195                      200                      205

Tyr  Gly  Thr  Phe  Leu  Tyr  Val
                       210                 215
```

( 2 ) INFORMATION FOR SEQ ID NO:35:

( i ) SEQUENCE CHARACTERISTICS:
        ( A ) LENGTH: 70 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:35:

```
         Met  Gly  Ser  Cys  Val  Ser  Val  Lys  Ser  Ile  Ser  Ile  Ser  Met  Asp  Thr
         1                   5                        10                       15

Val  Ser  Ile  Ser  Ser  Ile  Asp  Asp  Glu  Tyr  Tyr  Tyr  Asn  Ile  Lys  Asn
                            20                       25                       30

Lys  Pro  Ile  Tyr  Val  Arg  Arg  Lys  Asn  Ser  Cys  Ser  Ser  Thr  Leu  Glu
                       35                       40                       45

Ser  Arg  Tyr  Ser  Thr  Tyr  Ser  Leu  Glu  Ser  Arg  Tyr  Ser  Thr  Tyr  Ser
                  50                       55                       60

Ile  Lys  Ser  Val  Tyr  Phe
         65                      70
```

( 2 ) INFORMATION FOR SEQ ID NO:36:

( i ) SEQUENCE CHARACTERISTICS:
        ( A ) LENGTH: 1323 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:36:

```
ATGAAAGAAA  TTAATTCGTT  AGAATGTCAG  TGGGAGTCTA  TCGATGATAA  TAATGATACA      60
ACTATTCTCG  GTGATGATAT  ATATTTTGAT  TATATAATTT  CTCAGTTAGA  TATACATCAA     120
AATTGGTCTC  CTGATATCAG  ACTAATAAGA  TATTTTAGGA  AGTTAACAA   AGAATCATTT     180
GATAAAATAT  CAGATACGGA  ATATATTAAC  CCATCTTTTT  TCCAACAAAG  AGATAAACGA     240
TTTTATCCAC  TTAATGATGA  TTTCTATCAT  ATATCAACAG  GAGGTTATGG  TATCGTATTT     300
AAAATGGATA  AATACGTTGT  TAAATTTGTT  TATGAACCAA  ATAAACAGTA  TAGTCCATT      360
GATACAACTG  CCGAGTATAC  AATACCTAAA  TTTTTATATA  ATAATCTTAA  GGGAGATGAG     420
AAAAAACTTA  TCGTTTGTGC  ATGGGCAATG  GGTTTAAATT  ATAAATTAAC  ATTTCTACAT     480
AGATTATATA  AAAGAGTATT  ATATATGTTA  TTACTTATTA  TTCAAACGAT  AGATAATCAA     540
CGATTAAATA  TTCATCATTT  TTCTCATAAG  TATTTTCTTA  AGTCGTTCAA  TGAAAAAAAG     600
AGCGATATAA  AATTTGTAAA  ATTATTATCA  TATTTTTATC  CTATTGTTGT  TCAAAGTAAT     660
```

-continued

| | | | | | |
|---|---|---|---|---|---|
| ATAAATGTAA | TAAATTATTT | TACACATATG | TTTCATTTTT | TCGAACATGA | AAAAAGAGCT | 720
| AATTATTTAT | ACGATAGAGG | AAATATAATT | ATATTCCCAT | TAGCAAGATT | TTCATCAGAT | 780
| AAAGTGACGG | AACAGATGGC | GATAGAACTT | GGTTTTAAAT | CTATAGTTCA | ATATGTTAAG | 840
| TTTATTTTTT | TACAAATATC | ATTGTTATAT | ATAAAAATAT | ACGAACTTCC | TTGTTGTGAT | 900
| AATTTTTTAC | ACGTTGATTT | AAAACCCGAT | AATATTTTAA | TATTTAATTC | TGATTGTCCT | 960
| ATAACTATTA | AATTAAGAA | ATATACATAC | GTATTTAATG | AACCGATTAA | AGCGTGTCTT | 1020
| AACGATTTCG | ATTTTTCACA | GGTGGCTAAT | ATATTAAATA | AGAAAATTAA | AAATAGTTTA | 1080
| AAAATAGAAC | ACAATTGGTA | TTATGATTTT | CATTTTTTA | TACATACACT | TCTACGAACT | 1140
| TATCCAGAAA | TAGAATCTGA | TAAAGAATTC | AGCGATTCTT | TAGAGGATTT | TATAATGTGT | 1200
| TGTACAAAAA | ATACATGTGA | GAAATTTAGA | TTAAAAGTAT | CCATACTGCA | TCCTATATCA | 1260
| TTTTAGAAA | ATTTGATTAC | AAAAAACATT | TTCTCAAATT | GGATAAATGG | AGAATCCTGT | 1320
| TAG | | | | | | 1323

( 2 ) INFORMATION FOR SEQ ID NO:37:

( i ) SEQUENCE CHARACTERISTICS:
     ( A ) LENGTH: 204 base pairs
     ( B ) TYPE: nucleic acid
     ( C ) STRANDEDNESS: double
     ( D ) TOPOLOGY: unknown ( i i ) MOLECULE TYPE: DNA (genomic)

( x i ) SEQUENCE DESCRIPTION: SEQ ID NO:37:

| | | | | | |
|---|---|---|---|---|---|
| ATGCACCTTA | AAAATGAAGT | AAATAATAAT | ATGTTTGTTT | TTACTTTATG | TATTTTATTA | 60
| TACTCGTCTT | TTTGTTATTT | TTTTTATATT | GAAAAAATAT | TGCAACATAC | AAAGCCAATA | 120
| TATACGAACT | ATGGGCAGTT | GTGTATCTGT | AAAATCAATA | AGTATAAGTA | TGGATACAGT | 180
| GTCAATATCT | TCTATAGACG | ATGA | | | | 204

( 2 ) INFORMATION FOR SEQ ID NO:38:

( i ) SEQUENCE CHARACTERISTICS:
     ( A ) LENGTH: 222 base pairs
     ( B ) TYPE: nucleic acid
     ( C ) STRANDEDNESS: double
     ( D ) TOPOLOGY: unknown ( i i ) MOLECULE TYPE: DNA (genomic)

( x i ) SEQUENCE DESCRIPTION: SEQ ID NO:38:

| | | | | | |
|---|---|---|---|---|---|
| ATGAATAATC | GTAAGTATTC | AATAAATAAT | GGTTTTATGT | CATATTTACG | AAAGAAATTT | 60
| ACTACATTTT | TAAGAAAGAA | ATCAACTTAT | AGGATAAAAT | CTAATACCGA | CTATTACCAG | 120
| GAGAATGAAA | AGTTGATACA | TAAAAATAAC | ATCAAAATAC | CTTATAAAGT | AAAAGTTATA | 180
| AGGAAACGTT | GTAGTAGTAG | CGATGATGAT | GTTTTATTT | AG | | 222

( 2 ) INFORMATION FOR SEQ ID NO:39:

( i ) SEQUENCE CHARACTERISTICS:
     ( A ) LENGTH: 261 base pairs
     ( B ) TYPE: nucleic acid
     ( C ) STRANDEDNESS: double
     ( D ) TOPOLOGY: unknown ( i i ) MOLECULE TYPE: DNA (genomic)

( x i ) SEQUENCE DESCRIPTION: SEQ ID NO:39:

| | | | | | |
|---|---|---|---|---|---|
| ATGAATACAA | CAACTTCACA | AATAATTATA | GATAATGATA | TGTCTAATGA | AGTTGGAACA | 60

| | | | | | |
|---|---|---|---|---|---|
| ATAATGGTAA | TTACATTATG | TTTAGTTACT | ATCGTGATAA | CGTGTTATTT | ACTACTACAA | 120 |
| TTAGTAAGAT | GGTCGTTTAT | AGTAGATATA | TTTAGACAAA | TAAGAACTAG | ATGTTTACAA | 180 |
| TGGACATCGA | GAAGAGAATT | TTACAATTA | GATAATATGT | ATTATACGAA | CGATAGCAGC | 240 |
| GTTGGTGTTA | ATACCGAATA | A | | | | 261 |

( 2 ) INFORMATION FOR SEQ ID NO:40:

( i ) SEQUENCE CHARACTERISTICS:
        ( A ) LENGTH: 825 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:40:

| | | | | | |
|---|---|---|---|---|---|
| ATGGAGCCTA | TTCTTCAAGA | GTCTGATTCT | AGGTTCGTTA | TTTTCCCTAT | TAAGTATCAT | 60 |
| GATATCTGGA | AAATGTATAA | ACAATCAGTG | GCAAGTTTTT | GGACCGTTGA | AGAAGTAGAT | 120 |
| TTATCAAAAG | ATTTAGATGA | TTGGGATAAA | TTAACTAAAG | ACGAAAAATA | CTTTATAAAA | 180 |
| CATATACTAG | CATTTTTTGC | ATCTAGTGAT | GGTATTGTAA | ATGAGAATTT | AGCGGAAAGA | 240 |
| TTTTATGTGG | ATGTACAGTG | TTCAGAGGCA | CGATGTTTCT | ATGGATTTCA | AATAGCTATG | 300 |
| GAAAATATTC | ATTCAGAAAT | GTATAGTTTA | TTAATAGATA | CATATGTAAG | AGATAATATA | 360 |
| GAAAAAATGC | ATTTATTTAA | CGCTATAGAA | ACAATGGAAT | GCGTAAAAAA | GAAAGCTGAT | 420 |
| TGGGCCAGAA | AATGGATATC | TAGCAACAAG | GTATATGGAG | AAAGAGTAGT | AGCATTTGCA | 480 |
| GCTGTGGAGG | GAATATTCTT | TTCTGGTTCA | TTTGCTGCTA | TATTTGGAT | AAAAAAACGA | 540 |
| GGATTGATGC | CCGGATTAAC | ATTTCTAAT | GAACTAATAA | GTAGAGACGA | AGGTTTACAT | 600 |
| TGTGATTTTG | CGTGTTTAAT | GTTTAAACAT | TTATTACATC | CACCATCTAA | GGAAGTTATA | 660 |
| ACGTCGATAA | TCATTGATGC | GGTTAATATA | GAAAAGGAGT | TTTTGACAGT | TGCTATTCCG | 720 |
| GTGGATCTTA | TAGGTATGAA | TTGTTGTTTA | ATGTCTCAGT | ATATAGAATT | CGTCGCAGAT | 780 |
| AGATTATTAA | CAGAGTTAGG | TTGTGAAAAG | TCTCAATGTA | TATAA | | 825 |

( 2 ) INFORMATION FOR SEQ ID NO:41:

( i ) SEQUENCE CHARACTERISTICS:
        ( A ) LENGTH: 1503 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:41:

| | | | | | |
|---|---|---|---|---|---|
| ATGTCTAAAC | AAGAAACTTA | CATTGATTAT | AACTATATAG | AAAGGTTAAA | TGCTGTGAAT | 60 |
| CTAAACAGAA | GTTATGATGA | AGAGATAGTA | TTTATTATGA | CCGTTGGTGG | TGTTGTTAAA | 120 |
| GTAAAAAAAG | AATTACTTGT | ATCTGTATCT | AATTACTTTA | AACTTATTAC | AAAGAATCAG | 180 |
| AGTAATGAAA | TAACGGTTTC | ATTCCAGTAT | GAATCTTTTC | TTGATATAAT | AAAATATATA | 240 |
| GAAACTGGAA | TCGTTACTAT | CGATTTAGAC | AATGTAGAAA | ATATTTTTTC | CATATCTTGT | 300 |
| AGTAAAGCCA | TAGATTTTTT | AAAAAATTCA | TGTATTGATT | TTATGTCAAA | ACATATAACG | 360 |
| GATTCTACAT | GTGTTAAGAT | TTACAAAATA | GGTTTCTCGA | ATGGATGTTT | TGCGGTATAT | 420 |
| AATGATGCTA | TAGCATATAT | AAGGAAAAGA | TTCACAAAAA | TAGAAACAGA | TATATTACTA | 480 |
| TCGTTATCCT | TATTTGATTT | GAGAATAATT | CTAAAAGTG | GAGAATTAGA | TGTATCATCA | 540 |

-continued

| | | | | | |
|---|---|---|---|---|---|
| GAAGATGATG | TATTATTATT | TATAATAAAA | TGGTCTAGAC | ATAAAAAATC | CAACAGACGA | 600 |
| AAATCGTTTA | CACTAGTAAC | AGAGGTACTA | AGATATAATT | ATCTATCCAT | ATATGGTAAG | 660 |
| TATAAATTAA | CAAAATGGTT | GGCACGATTC | GGAAAAAATA | ATAATGTAGA | GTTAAATGAA | 720 |
| AATGAATTAC | CTAGAATAAG | TTATCAACAT | AGATTTACAA | ACAGAAGATA | TACGATGGTT | 780 |
| ACACCATCTT | CATTTAGTAT | AAATATGCTA | GGTAATGTAT | CTGTTAAGAA | TGAACTTAGT | 840 |
| ATAATCAATA | GTATAGCTGA | GAATCATAAT | CCTTACTGTG | GATCTGTACT | TATGAATGAT | 900 |
| ATATTATATC | TTATAGGTGG | TATAAATAAA | TCATTGGATC | CTGTTAGTGA | TATAACTAGC | 960 |
| GTAGACACTA | GATCATTTAT | AGAGTTGCAT | ACACCACCAT | TATTACATCC | TAGAAAGTGT | 1020 |
| CCGGGTGTTG | CTATTTTTAA | AAATAGAATT | TATGTGGTAG | GTGGTATAGG | ATACGATGGA | 1080 |
| CCATTAAAAA | CAGTAGAAAG | TTGGTCACCT | GGAGAACAAC | AATGGAGAGA | AGAAGTACCA | 1140 |
| TTATTACAAC | CCAGATTTAA | TCCTTGCATA | ATTGGAACAG | ATAATGATTT | ATATGTTGTT | 1200 |
| GGTGGTATTT | CTGAAGATGA | TAAAACTATT | GAAATCTATT | CTTATGAAGA | AAACACTTGG | 1260 |
| TCTATTGGTA | ATGCGATGAA | TTATTCACAT | TTGGTGGAT | GTATAGCATA | TCACCATGGT | 1320 |
| TATATATATA | TGATTGGTGG | TTTATCTTTT | ATAGATAATA | TTCATGTATT | TACTATGGTT | 1380 |
| GAGAAGTATA | ACCCTCATTC | GAATAAATGG | ACTGTAGAAA | AGTCTCTACC | CTTTCCTCGA | 1440 |
| TTTAATTCAT | CGCTTTGTAT | TATAGAAGAC | TCTATCGCTA | TAATAGGCTG | GATATATTAT | 1500 |
| TAA | | | | | | 1503 |

(2) INFORMATION FOR SEQ ID NO:42:

(i) SEQUENCE CHARACTERISTICS:
  (A) LENGTH: 228 base pairs
  (B) TYPE: nucleic acid
  (C) STRANDEDNESS: double
  (D) TOPOLOGY: unknown (ii) MOLECULE TYPE: DNA (genomic)

(xi) SEQUENCE DESCRIPTION: SEQ ID NO:42:

| | | | | | |
|---|---|---|---|---|---|
| ATGAATAAAT | ATAATAATTA | TAGAGCAATT | TATTTCTCT | ATAAAGTCAT | ATTACGAATA | 60 |
| CATAATACAG | AATATATAAG | TGGAACACTA | CAAAGATCTA | TACAGAATAT | AACACCTACA | 120 |
| ACATCATCAT | ATACGTATTG | TGATAATTCA | AAAAGACGCA | GACATAGATT | TAGAGATACG | 180 |
| GAAATCCTTA | AAGCTATGGG | TAGTAAAATG | CGTAGAAAAC | TTTTTTAG | | 228 |

(2) INFORMATION FOR SEQ ID NO:43:

(i) SEQUENCE CHARACTERISTICS:
  (A) LENGTH: 429 base pairs
  (B) TYPE: nucleic acid
  (C) STRANDEDNESS: double
  (D) TOPOLOGY: unknown (ii) MOLECULE TYPE: DNA (genomic)

(xi) SEQUENCE DESCRIPTION: SEQ ID NO:43:

| | | | | | |
|---|---|---|---|---|---|
| ATGTCACTAT | ATGTTAAATG | TGTTAAGTTA | TCTAATAATG | CTATTATACC | AAATAGATCA | 60 |
| ATGAGCGGAT | CCGCTGGATA | TGATCTGTAT | AGTGCATATA | GTTATACAGT | TAAGCCGTAT | 120 |
| AATAGAATTT | TAGTTAGAAC | AGATATTTGT | TTAATGATAC | CAGATAAATG | TTATGGACGC | 180 |
| ATATCGCCTA | GATCGGGATT | ATCGTTAAAT | TATAATATAG | ATATAGGAGG | AGGCGTTATT | 240 |
| GATAGTGATT | ACAGAGGGGA | AATAGGTATC | GTGTTTATAA | ATAATGGATG | TAGTGATTTT | 300 |
| AACATAAAGG | TAGGTGATAG | GATAGCACAA | ATAATATTTG | AAAGAGTAGA | ATATCCTATA | 360 |

ATGGAAGAAG TAAAATGTTT GGAAGATACA GAACGTGGAA ATAGTGGTTT TGGGTCAAGT    420

GGTATGTAA    429

( 2 ) INFORMATION FOR SEQ ID NO:44:

( i ) SEQUENCE CHARACTERISTICS:
        ( A ) LENGTH: 504 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:44:

ATGTACAAGA AATATAACTC TAACGTATGC ATTAGGAATG TATTATATGT ATATCTAAAA    60

TATAATACTA TAAATAAACT TAGTAGATAT GAACGGATGA TATACACAAA GATAAAAAAT    120

CAATGTGAAG CGATAAAATA CAGATATTGT AATGATTTTA ATTCTGTTAC ATGTATTTTA    180

GAATACGATG AAAATAAGTA TATAGATAAC GTGCATAAAG AAGTTATTAG TATATTGTTA    240

TCAGATTCGC GACCTAGTAT CAAATTAGCT GCTATTTCGT TATTATCTAT AATAATAGAT    300

AAACTAATAT GTAGAAATAT TCGTATAGCT AAATATATAA TTGATGATAT AATAAATATT    360

ATATCAGAAG ACGGTATATA TATTATATTA TTTTTAGATG AATTTGATAA ATATACCGAT    420

ACCCGATGTA GGCGCCGTGG ATTAAGTATG ATGATAGCGA GCATTGTAAC TTACTACTGT    480

TTACGGTATG TATTAAAAAT ATAA    504

( 2 ) INFORMATION FOR SEQ ID NO:45:

( i ) SEQUENCE CHARACTERISTICS:
        ( A ) LENGTH: 405 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:45:

ATGAACCGTA ATATGTGGAT AGTGTTATCG TGTGTATTAT ATATGATTTA TATATGTAAC    60

GGACGAGATG TATTGTTATA TCCACCACAT AAGAAAACAA ATAAGGTTAT AGTAAAATGT    120

AACGGATATA CTAATTCTAC GTATAGTATC TTATATTGGA TGGTAGGTAA CAACAATACA    180

TTCGTAGAAC AACTAAATAG CGATCATTAT AAAGAGAAGA ATACAATAG TACTGAAAAA    240

AATGAGCATA TGTATAAGTT ACGTACCGAT CTTATTATAT ATAATATTAC GTCAGAAATG    300

GAGATGACAA AACTAACATG TGTATTATCA GATATATACA CACCTATCAA GGCATCTATA    360

ATATTAAATA ATTTATGGAG TTGTTTAAAT ACTACACAAG TATGA    405

( 2 ) INFORMATION FOR SEQ ID NO:46:

( i ) SEQUENCE CHARACTERISTICS:
        ( A ) LENGTH: 261 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:46:

ATGTCAACTA TGAATACGTT GGCATTTTGT TATGGATTAC CTAACATAAA TGATATCACG    60

CAAGGTATAA TTTTTGTTAG AAATAACATA TTTTACTCAT ATTAACAGA TTATGCAATG    120

| | | | | | |
|---|---|---|---|---|---|
| GAAGCGTGTA | TATTGAATTA | TATAAATATT | AGAGCCGATA | AAATAGAAGA | TCTAAAGAAA | 180
| TCATTAGTTG | GAAAAACTAT | TAGCGTGAGA | GTTATTAGAG | TTGATGTATT | AAAAGGATAT | 240
| ATAGATGTTT | CAATTGTATA | A | | | | 261

( 2 ) INFORMATION FOR SEQ ID NO:47:

( i ) SEQUENCE CHARACTERISTICS:
        ( A ) LENGTH: 468 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:47:

| | | | | | |
|---|---|---|---|---|---|
| ATGGATCCTG | TTTGTTGGAT | ATGTAAAGAT | GACTACAGTA | TTGAAAAGAA | TTATTGTAAC | 60
| TGTAAAAACG | AGTATAAAGT | TGTACACGAT | GAATGTATGA | AAAAGTGGAT | ACAATACTCA | 120
| AGGGAACGAT | CTTGTAAATT | ATGTAATAAA | GAATATAACA | TCATTAGTGT | TAGAAAACCA | 180
| TTCTCACAGT | GGGTATTCTC | CATTAAAGAT | TGCAAAAAGT | CAGCAATTTT | GTACGCTACT | 240
| CTATTCTTAT | GTACGTTTAT | TATATCGCTT | GTTTAACTA | GAATTAATAT | AACAAAAATA | 300
| ATAGATACAT | CAAAAAATGA | TGTTTCATTT | AAGCTGGTTA | CGATGATATT | CTACTTATTA | 360
| CCATTTGTCA | TAACTTGTAT | ATCGTTCATA | ACGCTGATAG | TTTATCTATA | TAAATATTGT | 420
| AAGATTTCCG | CTAAAAACAA | CACATACGAT | ACGATTTATG | AACTTTAA | | 468

( 2 ) INFORMATION FOR SEQ ID NO:48:

( i ) SEQUENCE CHARACTERISTICS:
        ( A ) LENGTH: 825 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:48:

| | | | | | |
|---|---|---|---|---|---|
| ATGCATTTCA | TATTCATTAT | ATTATCACTA | TCATTTGTAG | TAAATGCCGA | TGTATTTCCA | 60
| TCGTCGGTTA | CTTTATCATC | TAATGATTTT | GATACAATAA | TTAAATGGGA | TAATAATGTA | 120
| ATATCATACG | ATGTAGAATT | AATGCAGTAC | AGTCATGACG | AATGGAGAAC | CGTTTGTACT | 180
| AATTCTTTAG | GATACTGTAA | TTAACAAAT | TCTGATATCG | ACAATGATGA | TGAAACATGG | 240
| GTGAGGTTTA | AATATGAAAA | TAAGACATCT | AATGAACATA | ATATTGGCAG | AGTATGTGAG | 300
| ATTGTACAAA | TAACTTCACC | TATTGTTAAC | ATGACAAGAG | ATGGTTCAAT | TATACTATTA | 360
| GATATACATC | ATCCAATGAC | ATACGATAAT | CAGTATTATA | TATATAATAA | TATAACATTA | 420
| TGTGGATTTG | AATTTATTTA | CGAAGCTACA | TTTATTATTA | ATGATACAAT | TATACCATAT | 480
| AGTATAGACA | ATCAATATTG | TGATGATGTT | CATTGTTTAT | TTACTTTAT | ATCACAAGAA | 540
| CCCGTTTGTG | TGTATGTAAT | GGGTATGGAA | CAATATTATG | AATTTGGTCC | AAAAAAAACA | 600
| GATAATAGTA | CTAGAGTGTG | TGTAGATGGA | TTAATTCCAA | GAAAAATCGA | TACATATTTT | 660
| ATTAAAGATT | TCGATGATAT | AGATAGAGTT | AATAACAGAT | TATATAGAGT | TGTAAGTGAT | 720
| AAATATGAAT | CCAATATATC | GTCAAAGTTT | ATGCACTTAT | ATAATAATAT | ATTATCTTCG | 780
| TTTAAACTAA | TATTGCAAGA | ACTTATGGTA | AATACTGAAC | AGTAA | | 825

( 2 ) INFORMATION FOR SEQ ID NO:49:

( i ) SEQUENCE CHARACTERISTICS:

5,651,972

119

-continued

120

```
        ( A ) LENGTH: 711 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:49:
```

| | | | | | |
|---|---|---|---|---|---|
| ATGAATTCGT | ATATTGTAAT | AAAAAATTCA | TTACGTGATT | ATAGATCTGG | AAGAATTATA | 60 |
| AGAAAATACA | TAAGAAAATT | AATAAGGAT | GAGTATAAGC | ATTTTGTGC | TGTATTTAGA | 120 |
| TTAAATGTAG | ATTTTTCTCA | AGATGATAAA | AATCCATCTA | GAAAAGAAGT | AATAAGAATA | 180 |
| ATAGATGAGG | AATTCAATTT | TTGTGATCTT | AGACTATTTT | ATGATATCAT | GACCGTTGTA | 240 |
| CCTAATCATA | TGAATGTGGC | ATCTATTATT | TATAGCGAAT | ACGAATATCT | TTTAAAAAAA | 300 |
| TCAAATTATA | AAAATAAGAA | GATAAATTAT | ACTATATTAG | ATAAGATTAA | TAAATATCAT | 360 |
| AGTATAGATG | ATATTATATT | TATGTATCTT | CATTGGAGAA | AAAAATATAA | CAACACATGC | 420 |
| GCATGTGGTA | AGTTATTTAA | GGAACTCATG | AAATATGATA | TATTAGCTAC | AAAATATATA | 480 |
| TATAATGATA | TTATAAATAC | ATACAAGAG | GGAGATACTA | TATCCATTAA | CATACGTTTA | 540 |
| AAATGTAAAG | ATGATATAAT | TAAACATTGT | AAGTCTTCTA | TAGGTATGTT | TGCTATATTA | 600 |
| TCATCGAAAA | TAATCGACGT | AGATTTGAT | GTTATATTCT | TTTCACAAAT | AAGTATAAGA | 660 |
| TATAGACTAA | TATTCAAAAA | ATATCTCATA | CAATCATTAT | ACTTACAATA | A | 711 |

```
( 2 ) INFORMATION FOR SEQ ID NO:50:

( i ) SEQUENCE CHARACTERISTICS:
        ( A ) LENGTH: 1593 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:50:
```

| | | | | | |
|---|---|---|---|---|---|
| ATGAATTCAT | TATTATTACG | ATTACATGAT | TTTTTAAAC | ATGGAATTAT | GTGTGATATA | 60 |
| AAAATAGTAT | CCATAGAGAA | TAATAAAACC | ATTAGCGCAC | ATAGGTTAAT | ATTATCTATG | 120 |
| TACTCTAAGT | ACTTTTATAA | TATATTTAAT | TCAGATTTTA | TTGATAAAAA | TAATGATGAA | 180 |
| ATCTATATAT | GCGCCGATTA | TGATATATTG | TATATTATAT | TGGAATTTAT | GTACACCGGT | 240 |
| AATATAGTAC | TAACAAAGGA | TAATATAGAA | TTAGTAATAC | AAGTCTGTGA | TTATCTATGT | 300 |
| ATAGATTCTT | TAATAAAAAT | ATGTGAAGAA | TATATATGCG | GTATAATAGA | TGAAACAAAT | 360 |
| TGTATACATC | TCTTAAACTT | TTCAGATACT | TACAATCTAC | AACGATTACG | TGAAATGTCA | 420 |
| AAATGGTATT | TACCAAAAAT | AATAAATAAT | AACAAACTGG | TAGTAGAATT | AGATATAGAT | 480 |
| GATATGATAT | TAATTATAAA | AGAAATTAAA | TACATTGCAT | GTGAATATAT | AGTTAAAAAA | 540 |
| ATAATATTAA | ATTGGATCGT | TCATAAAGAT | GAACGAATTA | TTTATACTAA | AAAATTAATG | 600 |
| AAACATATCA | ATGATCAAGA | CCATTATACA | TCCTTATCGG | ATATTGAATT | GTACAATAAT | 660 |
| ATACGGGAAC | GAATATATGA | TAACAAAGAA | CACGATGTAG | ATATATCACA | TAACTTTATA | 720 |
| ATAATGGTAG | GAGGAAAAAA | GATATTTAAT | ATAACCGCAT | TCAATCCGTT | ATCGAATAAA | 780 |
| AAACATATTA | TAGACAGATA | CGATGATATG | TTTGGTTGTA | AAACTCATTT | TAGTGTTGTA | 840 |
| TACTTAAATA | GTATACTATA | TATTATCGGT | GGAAAGAAAC | GAGGATATTT | CACTAAAGAG | 900 |
| GTGTTGTCAT | ATAATATAAA | AAACAAATTA | TGGTGTTACG | AACCAGAATT | AAATTATTTT | 960 |
| AGATACGATA | CATCTGTATG | TGTATCAAAT | GGGATGATAT | ATTCAATTGG | TGGAAAAGAT | 1020 |

| | | | | | | |
|---|---|---|---|---|---|---|
| ACAAATGGAT | ATATGACAAA | CATCGTAGAA | TTTTGGAAAC | CTGAATGGAA | ATCATGGTAT | 1080 |
| GATGGTCAAC | ATTTGTGTTA | TCCTAGATGT | TATATGTCGT | TGGTAGACTA | TAATAATGAA | 1140 |
| GTATATACAA | TAGGTGGATT | AAAAACATCA | ATAACGGATG | AATTTAATAT | AGAAATGATT | 1200 |
| GTATCAGACG | ATGCCGTAGA | GAAACTGACC | GATCATTCAT | GGATGAAGTT | AAAACAATTT | 1260 |
| CCCATAGCAA | AGAGTGGTAT | ATCATCCATA | GTATATAACG | ATTTTATATA | CTGTATAGGT | 1320 |
| GGTCGTATAG | ATACACCACA | TATAAGTATA | GAACACACTA | ACGATGTTTA | TATATATTCT | 1380 |
| TCAAGAGATG | ATTGTTGGAA | ATATTTATCA | AATACAAATG | TAAAAGATC | ATTTTGTCTA | 1440 |
| TCGTGTGTTT | TTAATAATGA | ATTATATATA | ATAGGTGGAT | ATAATACAAA | CAGTGTAGAA | 1500 |
| AAGTACAATA | AATTAAAAAA | TACATGGAAG | CGTTTAAACG | ATATTCCTAA | GTTTGAAGAA | 1560 |
| TGTGTTAATG | AAGCATCGGC | AATATATTTG | TAG | | | 1593 |

(2) INFORMATION FOR SEQ ID NO:51:

(i) SEQUENCE CHARACTERISTICS:
        (A) LENGTH: 810 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:51:

| | | | | | | |
|---|---|---|---|---|---|---|
| ATGTCAGATT | GTATATTCGT | ATTTCAGATT | CCGTTCATTG | TGTATAGTAA | ACTCGATCAA | 60 |
| TGGATTTTTG | GGAATATACT | ATGTAAAATA | ATGTCCGTAT | TATACTACGT | AGGATTCTTT | 120 |
| AGTAATATGT | TTATAATAAC | ACTTATGAGT | ATAGATAGAT | ATTTGCGAT | CGTTCATCCT | 180 |
| ATAAAGCGAC | AACCGTATAG | GACGAAACGT | ATAGGTATCC | TTATGTGCTG | TTCCGCTTGG | 240 |
| TTATTATCCT | TGATATTATC | TAGTCCCGTA | TCTAAACTAT | ACGAGAATAT | TCCTCATATG | 300 |
| TCTAAAGATA | TATACCAATG | TACTCTGACG | AACGAGAATG | ACTCCATAAT | CGCATTCATA | 360 |
| AAAAGACTGA | TGCAAATAGA | GATCACTATA | TTGGGATTCC | TGATACCTAT | AATCATATTC | 420 |
| GTATATTGCT | ATTATAGAAT | TTTTTCTACA | GTGGTTAGAT | TAAGAAATAG | ACGAAAGTAT | 480 |
| AAATCTATAA | AAATTGTATT | AATGATTGTT | GTATGTTCTC | TAATATGTTG | GATTCCGCTC | 540 |
| TATATCGTTC | TAATGATAGC | GACGATTGTT | AGCTTATATA | CATCTAATAT | ATTTAGACAT | 600 |
| CTGTGCCTCT | ATCTAAACCT | GGCCTATGCG | ATCACCTTTT | CGGAGACTAT | CTCGTTAGCG | 660 |
| CGTTGTTGTA | TAAATCCAAT | AATATATACA | CTGATAGGTG | AACATGTTCG | ATCTCGTATA | 720 |
| TCTAGCATAT | GTTCGTGTAT | ATATAGAGAC | AATAGGATTA | GGAAAAAACT | CTTTTCACGA | 780 |
| AAATCTTCTA | GCAGTAGCAA | TATTATTTAG | | | | 810 |

(2) INFORMATION FOR SEQ ID NO:52:

(i) SEQUENCE CHARACTERISTICS:
        (A) LENGTH: 279 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:52:

| | | | | | | |
|---|---|---|---|---|---|---|
| ATGCTATCGT | ATATTATTAA | TCCTTGCTA | AGTATTGTAT | ACTTTATATT | AGGAAATGTA | 60 |
| TCTAAGCTGC | TTACATATAT | ACTTATGAAA | ATAATGATTT | TTTACTTCG | TGCGGTGAAT | 120 |
| CCATACTCTC | TGATATCTAA | CAGAGGTTGG | CTGTCGCTGG | ATAGTATAAA | TCCCTTTAAA | 180 |

| AAGGAAAAGC | GTAGGGAGTC | TTTTCTATCT | AGTCTAAATC | CGTTTAGAAA | AGAGGAAACA | 240 |
| AAGAAAAAAG | AAGGTTTCTT | TTCTGGTTGG | TTCGGATAA | | | 279 |

( 2 ) INFORMATION FOR SEQ ID NO:53:

( i ) SEQUENCE CHARACTERISTICS:
        ( A ) LENGTH: 1023 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:53:

| ATGATTACTA | AAGCGATTGT | GATATTGTCT | ATTATTACAG | CATATGTAGA | TGCTTCCGCA | 60 |
| TTCTTAGTAT | ACAATTATAC | ATATACTTTA | CAAGATGATA | ATCATCGATA | TGACTTCGAA | 120 |
| GTCACCGATT | ATTTTAATGA | TATACTAATA | AAACGTTTAA | AACTAAATAG | CGAGACAGGA | 180 |
| AGACCAGAAT | TAAGAAATGA | ACCACCAACA | TGGTTTAATG | AGACTAAGAT | TAGATATTAT | 240 |
| CCGAAAAATA | ATTATAATTT | TATGTTCTGG | CTAAATAGAA | TGAGTGAAAC | GCTAGATGAG | 300 |
| ATAAATAAAC | TTCCAGAAAC | GAGTAATCCT | TACAAGACTA | TGTCCTTGAC | AATTGGATGT | 360 |
| ACTGATCTAA | GACAACTTCA | AGTAAATTTC | GGTTATGTTA | CTGTAGGTGG | TAATATATGG | 420 |
| ACACGATTCG | ACCCCAAGAA | TAAACGCTTT | AGTAAAGTTA | GATCACGTAC | ATTTCCAAAG | 480 |
| GTAGGAATGT | TAACTGTTAA | ATCACAACAC | TGGGAACGTG | TTATGGAACA | TCTTGGATCA | 540 |
| ATGGTAACAT | TAACATGTCC | GTTTACAGCG | GATGATTATT | ATAAAATTTC | TAAGGGATAT | 600 |
| ATAGATAAGC | CAGTTAAGCC | TACTGTTACA | GTTACAGGAA | TTGAAAGAGG | AGATAATACT | 660 |
| ACATTGATAT | GCACATTTGA | TAATCATTAT | CCGTCGTCGG | TCGCTGTTAA | ATGGTATAAC | 720 |
| ATCGAGGACT | TTGCTCCGGA | CTATCGTTAT | GATCCGTACG | TAAATGAATT | GCTTCCTGAT | 780 |
| ACGGACTATC | TACCGGGTGA | ACCAGGATAT | CCGACTATAA | CTAGGAGATT | AGGTGATAAA | 840 |
| TATTTATTTA | CATCATCACC | TAGGGTTATG | GTACCAACTA | TCATGTCTAA | TAGAATAGCA | 900 |
| TGTGTTGGAT | TCATAGTAC | GTTAGAACCA | AGCATATATA | GATGTGTAAA | CTGCTCGGGA | 960 |
| CCTGAGCCTG | TTTTACAATA | CCAGGGAGAT | AGAAGGAATG | ACTTGGAGGA | TGAGGAGGAT | 1020 |
| TAA | | | | | | 1023 |

( 2 ) INFORMATION FOR SEQ ID NO:54:

( i ) SEQUENCE CHARACTERISTICS:
        ( A ) LENGTH: 221 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:54:

| ATGATGATTT | CTATCATATA | TCAACAGGAG | GTTATGGTAT | CGTATTTAAA | ATGGATAAAT | 60 |
| ACGTTGTTAA | ATTTGTTTAT | GAACCAAATA | AACAGTATAG | TCCCATTGAT | ACAACTGCCG | 120 |
| AGTATACAAT | ACCTAAATTT | TTATATAATA | ATCTTAAGGG | AGATGAGAAA | AAACTTATCG | 180 |
| TTTGTGCATG | GGCAATGGGT | TTAAATTATA | AATTAACATT | T | | 221 |

( 2 ) INFORMATION FOR SEQ ID NO:55:

( i ) SEQUENCE CHARACTERISTICS:
        ( A ) LENGTH: 675 base pairs
        ( B ) TYPE: nucleic acid ( C ) STRANDEDNESS: double
( D ) TOPOLOGY: unknown ( i i ) MOLECULE TYPE: DNA (genomic)

( x i ) SEQUENCE DESCRIPTION: SEQ ID NO:55:

| | | | | | | |
|---|---|---|---|---|---|---|
| ATGGAGAATC | CTGTTAGAAT | AAATACATTA | TATAACGTAT | TCGTAGAAAG | ATATATAGAG | 60 |
| AACTTATCAA | TATATTCTAT | ACCTATTAAT | TCAACATGTG | GTATACATAT | AGGAGAAATC | 120 |
| AAAGGAACGT | TCAAAAGATG | TTTTTTGAAA | ATACTCAATA | TGTGTATAAA | CGATAAAGAA | 180 |
| CTAAGTTTCA | ATATTCTTAT | AAAGACGCTT | AAAGATGTAA | CTAGTACGTT | ATCTCAGAAA | 240 |
| GAGAAAGAGG | AATTATCTAA | AGAAATTGGA | ATTGATATAT | TAAACAATGA | CCCTAAATAT | 300 |
| GTACCAGAAA | TAATACGAAA | CTGTTCATCA | TCCGCAGATG | TAACAAATAT | TATTGATATT | 360 |
| CAAACATTAG | ATGTTGGAAA | ATGCATAGCT | CCGTACGATA | AACAGATTCT | ATTACAGATT | 420 |
| GTTAATTCTG | GTACTGCAGA | AGCAAACTGT | GTGATGAATT | CTATCATGAA | TTCTATGAAT | 480 |
| AGAAGATATA | TTGACAATGC | TAATATATAT | AATTATTTGA | ATTAACAAA | TAGACCATGG | 540 |
| TTTATATTTA | GCATCATTAT | TATTGCTATC | ATATTTGTTA | TAGGAATATG | TTCTATAAAA | 600 |
| AGACGAATAG | GAATTAAATA | CAAATATGGT | ACATTTTTAT | ATGTCTAAAC | CGGGTTAAAA | 660 |
| ATGAAACATA | AATCA | | | | | 675 |

( 2 ) INFORMATION FOR SEQ ID NO:56:

( i ) SEQUENCE CHARACTERISTICS:
        ( A ) LENGTH: 260 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:56:

| | | | | | | |
|---|---|---|---|---|---|---|
| ATGGGCAGTT | GTGTATCTGT | AAAATCAATA | AGTATAAGTA | TGGATACAGT | GTCAATATCT | 60 |
| TCTATAGACG | ATGAATATTA | TTATAATATA | AAAAATAAGC | CAATATATGT | AAGAAGAAAA | 120 |
| AATAGTTGTA | GTAGTACACT | AGAATCGAGA | TATTCTACAT | ATAGTCTAGA | ATCGAGATAT | 180 |
| TCCACATATA | GTATTAAATC | AGTATATTTC | TAAATAAATA | ATAATGAATA | ATCGTAAGTA | 240 |
| TTCAATAAAT | AATGGTTTTA | | | | | 260 |

( 2 ) INFORMATION FOR SEQ ID NO:57:

( i ) SEQUENCE CHARACTERISTICS:
        ( A ) LENGTH: 1104 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 287..832

( x i ) SEQUENCE DESCRIPTION: SEQ ID NO:57:

| | | | | | | |
|---|---|---|---|---|---|---|
| CTATTGGTTA | TTTATACGAA | CCATTATCCG | AGGAGTATAG | ACGTGTTATC | GACTTTAGTG | 60 |
| ACATGAAGAA | TTTACGATCT | ATGTTTAACA | AATAACGAT | CACGTATCTG | ATAAATGCAT | 120 |
| ACAAGTTAAT | AAAGGATATT | TATCAGATTT | TGTAACATCA | TTAATACGAT | TAAGCGATGT | 180 |
| GATATAAATA | CCTATGATTC | GTTGATATT | ACTTATATAG | ATCCAAGAAG | ACATATAACT | 240 |
| TGGAATAATA | TTTTATCCAT | ATTGAAGAAA | AATAAATAAA | CACTTT ATG TAT ATA | | 295 |

```
                                                   Met  Tyr  Ile
                                                    1
ATA  ATG  TCA  TGT  GGA  TTT  ATT  CAT  CTT  ATA  TTA  GGA  CCT  ATG  TTC  TCT        343
Ile  Met  Ser  Cys  Gly  Phe  Ile  His  Leu  Ile  Leu  Gly  Pro  Met  Phe  Ser
      5                        10                      15

GGA  AAG  AGT  ACA  GAA  TTA  ATT  AGG  TTA  GTA  AAC  CGG  TAT  CAA  ATA  GCC        391
Gly  Lys  Ser  Thr  Glu  Leu  Ile  Arg  Leu  Val  Asn  Arg  Tyr  Gln  Ile  Ala
 20                       25                       30                       35

ACG  TAT  AAT  TGT  AGA  GTT  ATA  AAA  TAT  TCT  AAA  GAT  AAT  AGA  TAT  GGA        439
Thr  Tyr  Asn  Cys  Arg  Val  Ile  Lys  Tyr  Ser  Lys  Asp  Asn  Arg  Tyr  Gly
                40                       45                       50

AAT  GAT  GCG  GTA  TAT  ACA  CAC  GAT  AAA  TGT  TAT  ATA  TCG  GCT  GTA  TCT        487
Asn  Asp  Ala  Val  Tyr  Thr  His  Asp  Lys  Cys  Tyr  Ile  Ser  Ala  Val  Ser
                55                       60                       65

ACG  GAT  TCC  TTA  TTT  GAT  ATA  AAA  GAT  ACA  CTA  GAT  GAT  GTA  GAT  ATT        535
Thr  Asp  Ser  Leu  Phe  Asp  Ile  Lys  Asp  Thr  Leu  Asp  Asp  Val  Asp  Ile
           70                       75                       80

GTT  GGA  ATA  GAC  GAA  GGA  CAA  TTC  TTT  AAT  GAT  ATT  GTA  GAG  TTT  TGT        583
Val  Gly  Ile  Asp  Glu  Gly  Gln  Phe  Phe  Asn  Asp  Ile  Val  Glu  Phe  Cys
      85                       90                       95

GAA  TAT  ATA  GCA  AAT  AAA  GGA  AAA  ATT  GTT  ATC  GTT  GCT  GCA  TTA  GAT        631
Glu  Tyr  Ile  Ala  Asn  Lys  Gly  Lys  Ile  Val  Ile  Val  Ala  Ala  Leu  Asp
100                      105                      110                      115

GGA  ACA  TAT  GAA  CGT  AAA  CCA  TTT  GGT  AAT  ATT  CTT  AAT  CTT  ATA  CCA        679
Gly  Thr  Tyr  Glu  Arg  Lys  Pro  Phe  Gly  Asn  Ile  Leu  Asn  Leu  Ile  Pro
                    120                      125                      130

TTA  TCG  GAA  AAA  GTT  ACT  AAA  TTA  AAT  GCT  ATA  TGC  ATG  ATA  TGT  CAT        727
Leu  Ser  Glu  Lys  Val  Thr  Lys  Leu  Asn  Ala  Ile  Cys  Met  Ile  Cys  His
               135                      140                      145

CGT  GAT  GCA  TCT  TTT  TCA  AAG  AGA  TTA  AGC  GAC  GAG  AAA  GAA  ATA  GAA        775
Arg  Asp  Ala  Ser  Phe  Ser  Lys  Arg  Leu  Ser  Asp  Glu  Lys  Glu  Ile  Glu
          150                      155                      160

TTG  ATA  GGA  GGA  AAA  GAA  AAG  TAT  TTA  TCG  GTA  TGT  CGT  TCA  TGT  TAC        823
Leu  Ile  Gly  Gly  Lys  Glu  Lys  Tyr  Leu  Ser  Val  Cys  Arg  Ser  Cys  Tyr
     165                      170                      175

TTA  ACC  TGAAATATTG  AAAATATAAT  TAATATCTTA  GAGCTATTTA  ATTTATAGTT                  879
Leu  Thr
180

ATTACCATG  GGTATTACAC  ATGAATTAGA  TATCTTTCTG  GTTAGTGAAG  ACATTGCTAT                 939

GAAACATGTC  GAACTTCATA  AAGGTAATAG  TTATGGTTGT  GTATTAAACA  TTAAATCATC                999

TTGTAGGAAA  CAAATGAAAT  AATATTTGTG  TTAAAGCCTG  ATGGACCGAA  ATAGATGCAT                1059

TAAACCATAT  CAAATGGAAG  CAGATCGAAT  ATATATAGAC  GTGAC                                 1104
```

( 2 ) INFORMATION FOR SEQ ID NO:58:

( i ) SEQUENCE CHARACTERISTICS:
        ( A ) LENGTH: 181 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Met  Tyr  Ile  Ile  Met  Ser  Cys  Gly  Phe  Ile  His  Leu  Ile  Leu  Gly  Pro
 1                  5                       10                      15

Met  Phe  Ser  Gly  Lys  Ser  Thr  Glu  Leu  Ile  Arg  Leu  Val  Asn  Arg  Tyr
                20                       25                      30

Gln  Ile  Ala  Thr  Tyr  Asn  Cys  Arg  Val  Ile  Lys  Tyr  Ser  Lys  Asp  Asn
           35                       40                      45
```

-continued

| | | | | | | | | | | | | | | |
|---|---|---|---|---|---|---|---|---|---|---|---|---|---|---|
| Arg | Tyr<br>50 | Gly | Asn | Asp | Ala | Val<br>55 | Tyr | Thr | His | Asp | Lys<br>60 | Cys | Tyr | Ile | Ser |
| Ala<br>65 | Val | Ser | Thr | Asp | Ser<br>70 | Leu | Phe | Asp | Ile | Lys<br>75 | Asp | Thr | Leu | Asp | Asp<br>80 |
| Val | Asp | Ile | Val | Gly<br>85 | Ile | Asp | Glu | Gly | Gln<br>90 | Phe | Phe | Asn | Asp | Ile<br>95 | Val |
| Glu | Phe | Cys | Glu<br>100 | Tyr | Ile | Ala | Asn | Lys<br>105 | Gly | Lys | Ile | Val | Ile<br>110 | Val | Ala |
| Ala | Leu | Asp<br>115 | Gly | Thr | Tyr | Glu | Arg<br>120 | Lys | Pro | Phe | Gly | Asn<br>125 | Ile | Leu | Asn |
| Leu | Ile<br>130 | Pro | Leu | Ser | Glu | Lys<br>135 | Val | Thr | Lys | Leu | Asn<br>140 | Ala | Ile | Cys | Met |
| Ile<br>145 | Cys | His | Arg | Asp | Ala<br>150 | Ser | Phe | Ser | Lys | Arg<br>155 | Leu | Ser | Asp | Glu | Lys<br>160 |
| Glu | Ile | Glu | Leu | Ile<br>165 | Gly | Gly | Lys | Glu | Lys<br>170 | Tyr | Leu | Ser | Val | Cys<br>175 | Arg |
| Ser | Cys | Tyr | Leu<br>180 | Thr | | | | | | | | | | | |

( 2 ) INFORMATION FOR SEQ ID NO:59:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:59:

THGA Y GARGG NCARTT Y TT                                                                 1 9

( 2 ) INFORMATION FOR SEQ ID NO:60:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:60:

GGNCCNATGT T Y AG Y GGN                                                                  1 8

We claim:

1. A recombinant vector comprising a swine poxvirus comprising a heterologous nucleotide sequence inserted into, or replacing all or a portion of a swine poxvirus gene or nucleic acid sequence, which gene or nucleic acid sequence is not essential to replication of the virus in a host cell, wherein said non-essential gene or nucleic acid sequence is selected from a gene or nucleic acid sequence present in the HindIII C fragment.

2. The recombinant vector according to claim 1 wherein said HindIII C fragment has a sequence selected from SEQ ID NOS: 1 and 14.

3. The vector according to claim 1 wherein said heterologous nucleotide sequence encodes a protein from a selected pathogen.

4. The vector according to claim 3 wherein said pathogen is pseudorabies.

5. An immunogenic composition comprising the vector of claim 3 and a suitable carrier.

6. A method of immunizing swine against pseudorabies, comprising administering a composition comprising the vector of claim 4 and a suitable carrier by scarification or intramuscular injection.

7. A vaccine composition comprising the swine poxvirus vector of claim 1, wherein said heterologous nucleotide sequence encodes an antigen capable of eliciting a protective immune response to a pathogen.

8. The vaccine composition of claim 7, wherein the HindIII C fragment has the sequence represented by SEQ ID NO: 1 or 14.

9. The vaccine composition of claim 7, wherein the heterologous nucleotide sequence encodes pseudorabies gp50 and gp63 proteins.

10. A therapeutic composition comprising the swine poxvirus vector of claim 1, wherein said heterologous nucleotide sequence encodes a protein capable of alleviating the clinical symptoms of disease.

11. The composition according to claim 10, wherein the HindIII C fragment has the sequence represented by SEQ ID NO: 1 or 14.

12. A method of vaccinating an animal against a selected pathogen comprising administering to said animal the composition of claim 7.

13. The method according to claim 12, wherein the HindIII C fragment has the sequence represented by SEQ ID NO: 1 or 14.

14. The method according to claim 12, wherein the pathogen is pseudorabies, the heterologous nucleotide sequence encodes pseudorabies gp50 and gp63 proteins, and the administration is scarification or intramuscular injection.

15. A method of treating an animal infected with a selected pathogen comprising administering to said animal the composition of claim 10.

16. The method according to claim 15, wherein the HindIII C fragment has the sequence represented by SEQ ID NO: 1 or 14.

17. The vector according to claim 4 wherein said heterologous nucleotide sequence encodes the pseudorabies gp50 and gp63 proteins.

* * * * *

UNITED STATES PATENT AND TRADEMARK OFFICE
CERTIFICATE OF CORRECTION

PATENT NO. : 5,651,972

DATED : July 29, 1997

INVENTOR(S) : Richard W. Moyer, Eladio Viñuela, E.P.J. Gibbs

It is certified that error appears in the above-indentified patent and that said Letters Patent is hereby corrected as shown below:

Column 1, line 58: "Pictinc," should read --Piccine,--.

Column 3, line 31: "mount" should read --amount--.

Column 3, lines 60-67 through Column 4, lines 1-14: These lines were deleted per Column 4, line 15: "Figure 6" should read --Figure 2--; and Column 4, lines 22-24:

Column 4, line 25: "Figure 8" should read --Figure 3--.

Column 4, line 29: "The thick solid line" should read --The hatched box--;

Column 5, lines 8-9: "gII, gIII," should read --gII, gIII,--.

Column 5, line 40: Insert the following

--SEQ ID NO.: 1 provides the DNA sequence of the sense strand (5' to 3') of the *Hind*III C fragment of SPV and the putative amino acid sequences [SEQ ID NOS: 2-7] encoded thereby. Reading frame 1 encodes C24R and C23R. Reading frame 2 encodes C27R. Reading frame 3 encodes C26R, C25R and C22R.

UNITED STATES PATENT AND TRADEMARK OFFICE
CERTIFICATE OF CORRECTION

PATENT NO. : 5,651,972

DATED : July 29, 1997

INVENTOR(S) : Richard W. Moyer, Eladio Viñuela, E.P.J. Gibbs

It is certified that error appears in the above-indentified patent and that said Letters Patent is hereby corrected as shown below:

SEQ ID NO.: 14 provides the DNA sequence of the reverse complement strand (5'-3') of the 14,176 bp from the *Hin*dIII C fragment of SPV and the putative amino acid sequences [SEQ ID NOS: 17, 18, 23, 26, 28, 30, 31, 33, 34] encoded by reading frame 1.

SEQ ID NO.: 14 also provides the DNA sequence of the reverse complement strand (5' to 3') of the 14,176 bp from the *Hin*dIII C fragment of SPV and the amino acid sequences [SEQ ID NOS: 15, 20-22, 27, 32, 35] encoded by reading frame 2.

In addition, SEQ ID NO.: 14 provides the DNA sequence of the reverse complement strand (5' to 3') of the 14,176 bp from the *Hin*dIII C fragment of SPV and the amino acid sequences [SEQ ID NOS: 16, 19, 24, 25, 29] encoded by reading frame 3.

SEQ ID NO.: 57 provides the DNA sequence, and putative amino acid sequence [SEQ ID NO: 58], of the SPV TK gene.--

Column 5, line 47: "allclio" should read --allelic--.

Column 6, line 2: "antino" should read --amino--.

Column 6, line 32: "fight" should read --right--.

Column 7, line 20: "[SEQ I12 NO:57]" should read --[SEQ ID NO: 57]--.

UNITED STATES PATENT AND TRADEMARK OFFICE
CERTIFICATE OF CORRECTION

PATENT NO. : 5,651,972

DATED : July 29, 1997

INVENTOR(S) : Richard W. Moyer, Eladio Viñuela, E.P.J. Gibbs

It is certified that error appears in the above-indentified patent and that said Letters Patent is hereby corrected as shown below:

Column 8, line 40: "Bordetella," should read --Bordetella,--.

Column 8, line 43: "1 to 5 ml," should read --1 to 5 mL,--.

Column 10, line 15: "BamHi" should read --BamHI--.

Column 10, line 16: "SaII" should read --SalI--.

Column 11, line 1: "GGXCCXATGTF(" should read --GGXCCXATGTT(--.

Column 11, line 12: "The sequence of the TK gene [SEQ ID NO. 57] is shown in FIG. 7" should read --The sequence of the TK gene is shown in SEQ ID NO> 57,--.

Column 11, line 32: "(FIG. 3, 4, and 5). Figure 3 illustrates the DNA sequence [SEQ ID NO. 14]" should read --SEQ ID NO. 14 illustrates the DNA sequence--.

Column 12, line 7: "fight" should read --right--.

Column 12, line 8: "FIG. 4 also illustrates the DNA sequence [SEQ ID NO: 14]" should read --SEQ. ID NO. 14: Also illustrates the DNA sequence--.

UNITED STATES PATENT AND TRADEMARK OFFICE
CERTIFICATE OF CORRECTION

PATENT NO. : 5,651,972

DATED : July 29, 1997

INVENTOR(S) : Richard W. Moyer, Eladio Viñuela, E.P.J. Gibbs

It is certified that error appears in the above-indentified patent and that said Letters Patent is hereby corrected as shown below:

Column 12, line 15: "FIG. 5 illustrates the DNA sequence [SEQ ID NO: 14]" should read --SEQ ID NO. 14: illustrates the DNA sequence--.

Column 12, line 19: "FIG. 2 illustrates the DNA sequence of the same sense strand" should read --SEQ ID NO. 1: illustrates the DNA sequence of the sense strand--.

Column 12, line 25: "fight" should read --right--.

Column 13, line 30: "GertBank" should read --GenBank--.

Column 13, line 35: "homolog" should read --homology--.

Column 13, line 44: "[SEQ D NO.: 33]" should read --[SEQ ID NO: 33]--.

Column 13, line 47: "[SEQ D NO: 34]" should read --[SEQ ID NO: 34]--.

Column 13, line 52: "[SEQ D NO: 16]" should read --[SEQ ID NO: 16]--.

Column 14, line 30: "[SEQ D NO: 22]" should read --[SEQ ID NO: 22]--.

Column 15, line 21: "Thyroidine" should read --Thymidine--.

Column 15, line 29: "evaluated/n vitro" should read --evaluated in vitro--.

Column 15, line 49: "Fetal" should read --Fecal--.

UNITED STATES PATENT AND TRADEMARK OFFICE
CERTIFICATE OF CORRECTION

PATENT NO. : 5,651,972

DATED : July 29, 1997

INVENTOR(S) : Richard W. Moyer, Eladio Viñuela, E.P.J. Gibbs

It is certified that error appears in the above-indentified patent and that said Letters Patent is hereby corrected as shown below:

Column 17, line 1: "0.8 mi" should read --0.8 ml--.

Column 17, line 66: "tilers" should read --titers--.

Column 18, line 5: "Breek" should read --Breed--.

Column 18, line 58: "ad libiturn" should read --ad libitum--.

Column 20, line 44: "liter" should read --titer--.

Column 20, line 66: "Fetal" should read --Fecal--.

Column 23, line 19: "trial (Example 6)." should read --trial 2 (Example 6).--.

Column 130, line 59, (claim 8): "wherein the Hind1II C" should read --wherein the HindIII C--.

UNITED STATES PATENT AND TRADEMARK OFFICE
CERTIFICATE OF CORRECTION

PATENT NO. : 5,651,972

DATED : July 29, 1997

INVENTOR(S) : Richard W. Moyer, Eladio Viñuela, E.P.J. Gibbs

It is certified that error appears in the above-indentified patent and that said Letters Patent is hereby corrected as shown below:

Column 131, line 2, (claim 11): "wherein the Hind1II C" should read --wherein the HindIII C--.

Column 131, line 8, (claim 13): "wherein the Hind1II C" should read --wherein the HindIII C--.

Column 132, line 5, (claim 16): "wherein the Hind1II C" should read --wherein the HindIII C--.

Signed and Sealed this

Nineteenth Day of October, 1999

Attest:

Q. TODD DICKINSON

Attesting Officer

Acting Commissioner of Patents and Trademarks